US012272453B2

(12) United States Patent
Neihouser et al.

(10) Patent No.: US 12,272,453 B2
(45) Date of Patent: Apr. 8, 2025

(54) TOOL FOR CONFIGURING HEADWALL UNITS USED FOR PATIENT SUPPORT APPARATUS COMMUNICATION

(71) Applicant: Stryker Corporation, Kalamazoo, MI (US)

(72) Inventors: Kirby M. Neihouser, Portage, MI (US); Krishna Sandeep Bhimavarapu, Kalamazoo, MI (US); Nicholas S. Brajak, Portage, MI (US); Michael Harry Lau, Bristol, IN (US); Jerald A. Trepanier, Kalamazoo, MI (US)

(73) Assignee: Stryker Corporation, Portage, MI (US)

( * ) Notice: Subject to any disclaimer, the term of this patent is extended or adjusted under 35 U.S.C. 154(b) by 490 days.

(21) Appl. No.: 17/559,374

(22) Filed: Dec. 22, 2021

(65) Prior Publication Data

US 2022/0208368 A1    Jun. 30, 2022

Related U.S. Application Data

(60) Provisional application No. 63/131,508, filed on Dec. 29, 2020.

(51) Int. Cl.
*G06F 13/00* (2006.01)
*G06F 13/38* (2006.01)
(Continued)

(52) U.S. Cl.
CPC ........... *G16H 40/63* (2018.01); *G06F 13/382* (2013.01); *G06F 13/4282* (2013.01); *G06F 2213/0042* (2013.01)

(58) Field of Classification Search
None
See application file for complete search history.

(56) References Cited

U.S. PATENT DOCUMENTS 7,852,208 B2   12/2010   Collins, Jr. et al.
9,999,375 B2    6/2018   Hayes et al.
(Continued)

FOREIGN PATENT DOCUMENTS

WO         9427544         12/1994

OTHER PUBLICATIONS

PCT International Search Report completed Feb. 1, 2022, for International application No. PCT/US21/63565.

*Primary Examiner* — Henry Tsai
*Assistant Examiner* — Dean Phan
(74) *Attorney, Agent, or Firm* — Warner Norcross + Judd LLP

(57) ABSTRACT

A portable configuration tool for configuring a headwall unit that is adapted to be electrically coupled to an outlet on a headwall communicates with a room device positioned within a common room with the headwall unit. The tool includes a housing, a transceiver for communicating with a portable computer, IR and RF transceivers for communicating with the headwall unit, and a controller adapted to receive a command from the portable computer that instructs the controller to transmit an initial message to the headwall unit using the infrared transceiver, receive an identifier from the headwall unit via the infrared transceiver that uniquely identifies the headwall unit, establish a communication link between the RF transceiver and the headwall unit, receive a configuration setting from the portable computer via the transceiver, and transmit the configuration setting to the headwall unit via at least one of the infrared or RF transceivers.

15 Claims, 25 Drawing Sheets

(51) Int. Cl.
*G06F 13/42* (2006.01)
*G16H 40/63* (2018.01)

(56) References Cited

U.S. PATENT DOCUMENTS

| | | |
|---|---|---|
| 10,235,845 B2 | 3/2019 | Bhimavarapu et al. |
| 10,257,063 B2 | 4/2019 | Bhimavarapu et al. |
| 2002/0167417 A1 | 11/2002 | Welles, II et al. |
| 2006/0149504 A1* | 7/2006 | Hsieh .................... G08C 23/04 702/183 |
| 2007/0176788 A1 | 8/2007 | Mor et al. |
| 2011/0247139 A1* | 10/2011 | Tallent .................. A61G 7/018 5/613 |
| 2013/0297840 A1* | 11/2013 | Kagan .................... G06F 13/12 710/69 |
| 2015/0257952 A1 | 9/2015 | Zerhusen et al. |
| 2016/0038361 A1 | 2/2016 | Bhimavarapu et al. |
| 2016/0196400 A1 | 7/2016 | Hanning et al. |
| 2018/0338682 A1 | 11/2018 | Collins, Jr. et al. |
| 2018/0344254 A1* | 12/2018 | George ................. G16H 40/63 |
| 2019/0046379 A1 | 2/2019 | Constant et al. |
| 2019/0150737 A1 | 5/2019 | Bodurka et al. |
| 2019/0183705 A1* | 6/2019 | Bodurka ................ H04B 5/70 |
| 2019/0188992 A1* | 6/2019 | Bodurka ................ A61G 12/00 |

* cited by examiner

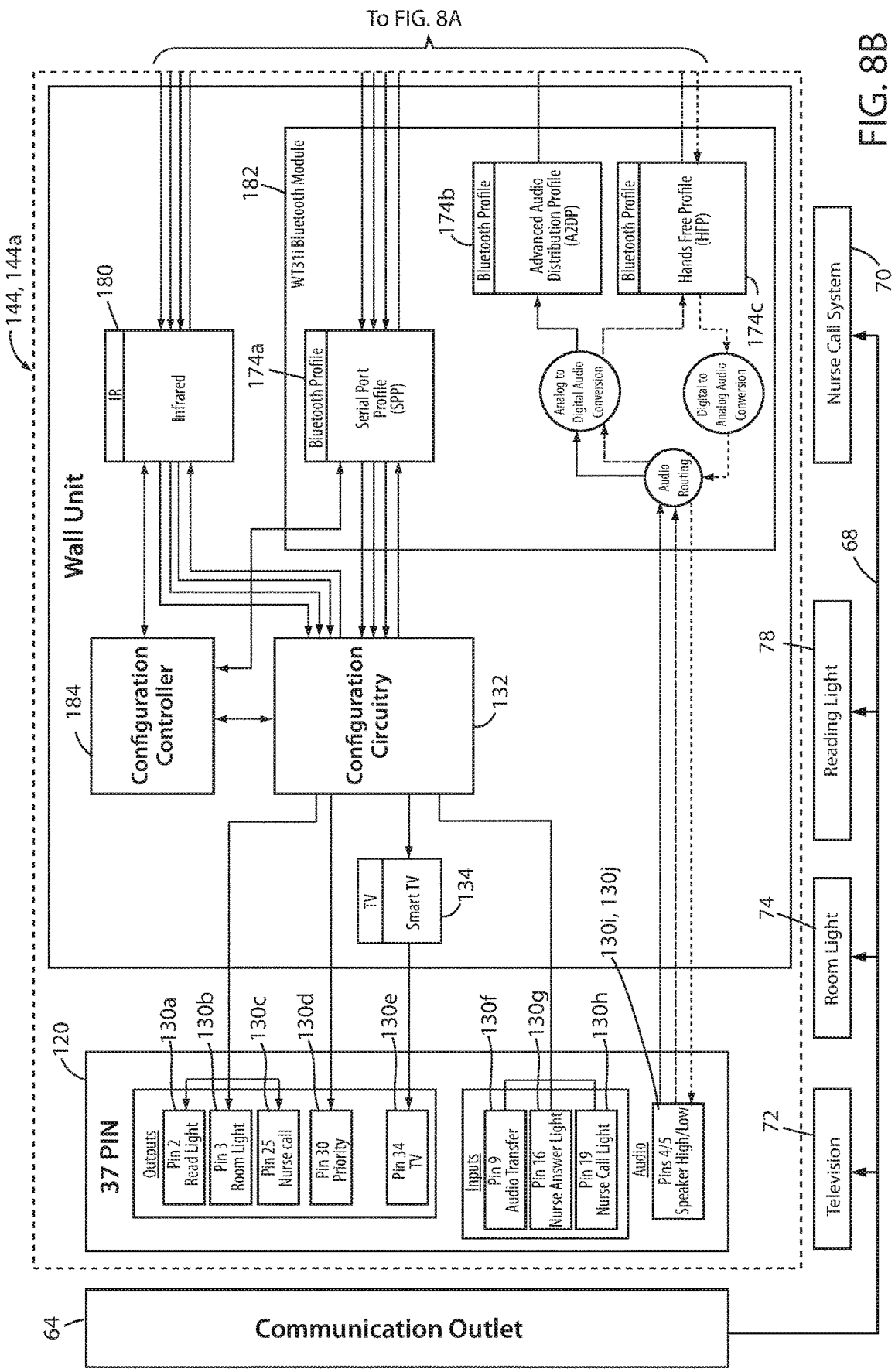

Pin 1    Bed Monitoring Status On
Pin 2    Read Light
Pin 3    Room Light
Pin 4    Speaker High
Pin 5    Potentiometer Wiper
Pin 6    Bed Exit Status On
Pin 7    Nurse Call Interlock
Pin 8    Audio Transfer -
Pin 9    Audio Transfer +
Pin 10   Interlock +
Pin 11   Interlock -
Pin 12   Bed Monitoring Fowler 30 deg. Alert
Pin 13   No Connect
Pin 14   Potentiometer Low Common
Pin 15   Potentiometer High Common (Std.) / Audio (STV)
Pin 16   Nurse Answer Light +
Pin 17   Bed Monitor Alert
Pin 18   Bed Monitoring Siderail Alert
Pin 19   Nurse Call Light +
Pin 20   No Connect
Pin 21   No Connect
Pin 22   No Connect
Pin 23   Brake Status On
Pin 24   No Connect
Pin 25   Nurse Call +
Pin 26   Nurse Call NO/NC
Pin 27   Room/Read Light Common
Pin 28   Nurse Call Light -
Pin 29   Nurse Answer Light -
Pin 30   Priority NO/NC
Pin 31   Priority Common
Pin 32   Bed Monitoring Low Height Alert
Pin 33   TV - (Std.) / Data (STV)
Pin 34   TV + (Std.) / Common (STV)
Pin 35   Speaker Low Common
Pin 36   Audio Shield
Pin 37   Bed Monitoring Common FIG. 32
(Prior Art)

TOOL FOR CONFIGURING HEADWALL UNITS USED FOR PATIENT SUPPORT APPARATUS COMMUNICATION

CROSS-REFERENCE TO RELATED APPLICATIONS

This application claims priority to U.S. provisional patent application Ser. No. 63/131,508 filed Dec. 29, 2020, by inventors Kirby Neihouser et al. and entitled TOOL FOR CONFIGURING HEADWALL UNITS, the complete disclosure of which is incorporated herein by reference.

BACKGROUND

The present disclosure relates to patient support apparatuses, such as beds, cots, stretchers, recliners, or the like, that are adapted to communicate with an existing nurse call system and/or one or more room devices using a headwall unit. More specifically, the present disclosure relates to a tool for configuring the headwall unit so that the patient support apparatuses can use it to properly communicate with the nurse call system and/or room devices.

Existing hospital beds often include an exit detection system that detects when the patient leaves the bed and notifies a nurse call system that the patient has left the bed. Existing hospital beds also often include a nurse call button and speaker that allow the patient to communicate with a remote nurse using the nurse call system. Still other signals of the bed may also be communicated to and/or through the nurse call system, and/or to a room interface that routes the signals to one or more room devices. Such room devices may include a television, one or more lights, a thermostat, etc., and the signals communicated from the bed may include commands to change one or features of these devices (e.g. a volume or channel of the television, an on/off state of the television, a room temperature, etc.)

In some situations, the hospital beds communicate with the nurse call system and/or the room devices using a headwall unit as a communication intermediary. In such situations, the patient support apparatuses may communicate wirelessly with the headwall unit, and the headwall units need to be properly configured to match the particular nurse call system and/or room devices that are installed in a particular healthcare facility. This is because different manufacturers of nurse call systems and room devices handle communications in different manners. Further, different healthcare facilities may have different types of communication outlets mounted in the headwalls of their rooms, and the headwall units need to be able to be configured to match the different constructions and/or different configurations of the communications outlets.

SUMMARY

According to various embodiments, the present disclosure provides an improved tool for easily configuring one or more headwall units that are used as communication intermediaries between patient support apparatuses and the existing communication infrastructure of the healthcare facility (e.g. the existing nurse call system and the room devices, such as televisions, room lights, etc.). The tool enables a technician or other authorized individual to configure headwall units so that they are compatible with the specific nurse call system and/or room devices that are installed in a particular healthcare facility. By configuring the headwall units to match the existing communication infrastructure of a healthcare facility, the individual patient support apparatuses do not need to be individually configured. Instead, the patient support apparatuses may all be uniformly manufactured to communicate with the headwall units in the same manner. The role of ensuring communications to and from the patient support apparatuses are compatible with the healthcare facilities communication infrastructure is thereby able to be offloaded to the headwall units, and the tool of the present disclosure makes the configuration process for the headwall units easier and more efficient. These and other features of the present disclosure will be apparent to one of ordinary skill in light of the accompanying drawings and the following written description.

According to a first embodiment of the present disclosure, a portable configuration tool is provided for configuring a headwall unit that is attached to a headwall of a healthcare facility, wherein the headwall unit is adapted to be electrically coupled to an outlet on the headwall that is in electrical communication with a room device and/or a nurse call system. The configuration tool includes a housing a transceiver, a first infrared transceiver, a first RF transceiver, and a controller. The transceiver is adapted to allow the tool to communicate with a portable computer. The first infrared transceiver is adapted to communicate with a second infrared transceiver incorporated into the headwall unit. The first RF transceiver adapted to communicate with a second RF transceiver incorporated into the headwall unit. The controller is adapted to perform the following: (a) receive a command from the portable computer via the transceiver wherein the command instructs the controller to transmit an initial message to the headwall unit using the first infrared transceiver; (b) receive an identifier from the headwall unit via the first infrared transceiver wherein the identifier uniquely identifies the headwall unit; (c) establish a communication link between the first RF transceiver and the second RF transceiver; (d) receive a configuration setting from the headwall unit via the first RF transceiver; and (e) transmit the configuration setting to the portable computer via the transceiver.

According to another embodiment of the present disclosure, a portable configuration tool is provided for configuring a headwall unit that is attached to a headwall of a healthcare facility, wherein the headwall unit is adapted to be electrically coupled to an outlet on the headwall that is in electrical communication with a room device and/or a nurse call system. The configuration tool includes a housing a transceiver, a first infrared transceiver, a first RF transceiver, and a controller. The transceiver is adapted to allow the tool to communicate with a portable computer. The first infrared transceiver is adapted to communicate with a second infrared transceiver incorporated into the headwall unit. The first RF transceiver adapted to communicate with a second RF transceiver incorporated into the headwall unit. The controller is adapted to perform the following: (a) receive a command from the portable computer via the transceiver wherein the command instructs the controller to transmit an initial message to the headwall unit using the first infrared transceiver; (b) receive an identifier from the headwall unit via the first infrared transceiver wherein the identifier uniquely identifies the headwall unit; (c) establish a communication link between the first RF transceiver and the second RF transceiver; (d) receive a configuration setting from the portable computer via the transceiver; and (e) transmit the configuration setting to the headwall unit via at least one of the first infrared transceiver or the first RF transceiver.

According to still another embodiment of the present disclosure, a portable configuration tool is provided for configuring a headwall unit that is attached to a headwall of a healthcare facility, wherein the headwall unit is adapted to be electrically coupled to an outlet on the headwall that is in electrical communication with a room device and/or a nurse call system. The configuration tool includes a housing a transceiver, a first infrared transceiver, a first RF transceiver, and a controller. The transceiver is adapted to allow the tool to communicate with a portable computer. The first infrared transceiver is adapted to communicate with a second infrared transceiver incorporated into the headwall unit. The first RF transceiver adapted to communicate with a second RF transceiver incorporated into the headwall unit. The controller is adapted to perform the following: (a) receive a command from the portable computer via the transceiver wherein the command instructs the controller to transmit an initial message to the headwall unit using the first infrared transceiver; (b) receive an identifier from the headwall unit via the first infrared transceiver wherein the identifier uniquely identifies the headwall unit; (c) establish a communication link between the first RF transceiver and the second RF transceiver; (d) receive a test command from the portable computer via the transceiver; and (e) transmit a test message to the headwall unit via at least one of the first infrared transceiver or the first RF transceiver in response to receiving the test command, wherein the test message instructs the headwall unit to take a particular action.

According to other aspects, the transceiver may be a wired Universal Serial Bus (USB) transceiver and the controller may be adapted to receive electrical power from the portable computer.

In some embodiments, the first and second RF transceivers are Bluetooth transceivers.

The portable computer, in some embodiments, is one of a laptop or a smart phone.

In some embodiments, the outlet is in electrical communication with both a nurse call system installed in the healthcare facility and one or more room devices.

The room device, in some embodiments, is a television positioned within the room. In such embodiments, the outlet includes at least one pin in electrical communication with the television, and the configuration setting includes voltage data specifying a voltage level the headwall unit is to apply to the pin in order to control the television. In some such embodiments, the configuration setting may further include sequence data specifying a first sequence of voltage levels the headwall unit is to apply to the pin to cause the television to change channels and a second sequence of voltage levels the headwall unit is to apply to the pin to cause the television to change volume.

In some embodiments, the headwall unit is further adapted to use the second infrared transceiver to communicate with a third infrared transceiver positioned onboard a patient support apparatus, and to use the second RF transceiver to communicate with a third RF transceiver positioned onboard the patient support apparatus.

The controller, in some embodiments, is further adapted to receive a new configuration setting from the portable computer, transmit the new configuration setting to the headwall unit, and to instruct the headwall unit to replace the configuration setting with the new configuration setting.

The outlet, in some embodiments, includes a plurality of pins in communication with the nurse call system. In such embodiments, the configuration setting may include a nurse call configuration setting specifying which one of the plurality of pins is to be used to communicate an exit alert from a patient support apparatus to the nurse call system.

In those embodiments where the controller is further adapted to receive a test command from the portable computer and to transmit a test message to the headwall unit instructing the headwall unit to take a particular action, the particular action may be to transmit a command to the television to change a channel of the television. Alternatively or additionally, the particular action may be to transmit a command to the room light to turn on and/or off. Still further, the particular action may be to transmit a command to the nurse call system indicating that a patient has exited from a patient support apparatus.

In some embodiments, the controller is further adapted to perform the following: (a) monitor a first set of heartbeat messages exchanged between the first infrared transceiver and the second infrared transceiver; (b) monitor a second set of heartbeat messages exchanged between the first RF transceiver and the second RF transceiver; and (c) transmit first and second error data regarding the first and second sets of heartbeat messages, respectively, to the portable computer via the transceiver.

In some embodiments, the controller is further adapted to transmit one or more configuration settings to the headwall unit via both the first infrared transceiver and the first RF transceiver.

In some embodiments, the controller is further adapted to read a stored configuration setting stored in the headwall unit and to transmit the stored configuration setting to the portable computer via the transceiver.

The controller, in some embodiments, is adapted to receive a plurality of additional configuration settings from the portable computer via the transceiver and to transmit the plurality of additional configuration settings to the headwall unit via at least one of the first infrared transceiver or the first RF transceiver.

The headwall unit, in some embodiments, is adapted to use its RF and IR transceivers to establish communication links with a patient support apparatus wherein the patient support apparatus is one of a bed, a stretcher, a chair, a recliner, or a cot.

Before the various embodiments disclosed herein are explained in detail, it is to be understood that the claims are not to be limited to the details of operation or to the details of construction and the arrangement of the components set forth in the following description or illustrated in the drawings. The embodiments described herein are capable of being practiced or being carried out in alternative ways not expressly disclosed herein. Also, it is to be understood that the phraseology and terminology used herein are for the purpose of description and should not be regarded as limiting. The use of "including" and "comprising" and variations thereof is meant to encompass the items listed thereafter and equivalents thereof as well as additional items and equivalents thereof. Further, enumeration may be used in the description of various embodiments. Unless otherwise expressly stated, the use of enumeration should not be construed as limiting the claims to any specific order or number of components. Nor should the use of enumeration be construed as excluding from the scope of the claims any additional steps or components that might be combined with or into the enumerated steps or components.

BRIEF DESCRIPTION OF THE DRAWINGS

FIG. 8B is a second portion of the control system of the patient support apparatus of FIG. 7;

FIG. 32 is a chart of a prior art example of the functions of the pins of a 37-pin cable often used in existing healthcare facilities.

DETAILED DESCRIPTION OF THE EMBODIMENTS

Figure 1:
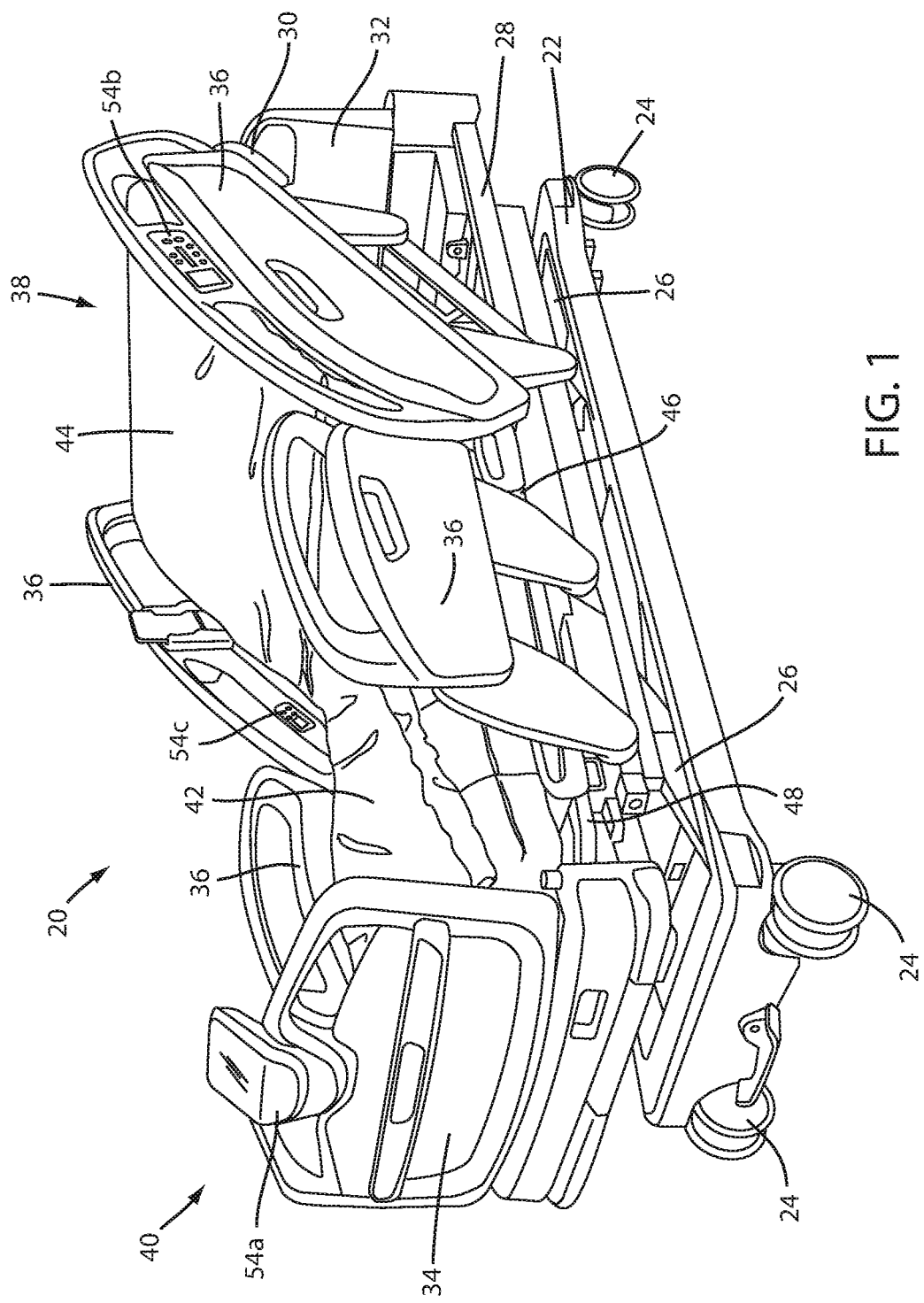
FIG. 1 is a perspective view of a patient support apparatus according to a first embodiment of the present disclosure.

An illustrative patient support apparatus 20 according to a first embodiment of the present disclosure is shown in FIG. 1. Although the particular form of patient support apparatus 20 illustrated in FIG. 1 is a bed adapted for use in a hospital or other medical setting, it will be understood that patient support apparatus 20 could, in different embodiments, be a cot, a stretcher, a recliner, or any other structure capable of supporting a patient in a healthcare environment.

In general, patient support apparatus 20 includes a base 22 having a plurality of wheels 24, a pair of lifts 26 supported on the base 22, a litter frame 28 supported on the lifts 26, and a support deck 30 supported on the litter frame 28. Patient support apparatus 20 further includes a headboard 32, a footboard 34 and a plurality of siderails 36. Siderails 36 are all shown in a raised position in FIG. 1 but are each individually movable to a lower position in which ingress into, and egress out of, patient support apparatus 20 is not obstructed by the lowered siderails 36.

Lifts 26 are adapted to raise and lower litter frame 28 with respect to base 22. Lifts 26 may be hydraulic actuators, electric actuators, or any other suitable device for raising and lowering litter frame 28 with respect to base 22. In the illustrated embodiment, lifts 26 are operable independently so that the tilting of litter frame 28 with respect to base 22 can also be adjusted, to place the litter frame 28 in a flat or horizontal orientation, a Trendelenburg orientation, or a reverse Trendelenburg orientation. That is, litter frame 28 includes a head end 38 and a foot end 40, each of whose height can be independently adjusted by the nearest lift 26. Patient support apparatus 20 is designed so that when an occupant lies thereon, his or her head will be positioned adjacent head end 38 and his or her feet will be positioned adjacent foot end 40.

Litter frame 28 provides a structure for supporting support deck 30, the headboard 32, footboard 34, and siderails 36. Support deck 30 provides a support surface for a mattress 42, or other soft cushion, so that a person may lie and/or sit thereon. The top surface of the mattress 42 or other cushion forms a support surface for the occupant.

Support deck 30 is made of a plurality of sections, some of which are pivotable about generally horizontal pivot axes. In the embodiment shown in FIG. 1, support deck 30 includes at least a head section 44, a thigh section 46, and a foot section 48, all of which are positioned underneath mattress 42 and which generally form flat surfaces for supporting mattress 42. Head section 44, which is also sometimes referred to as a Fowler section, is pivotable about a generally horizontal pivot axis between a generally horizontal orientation (not shown in FIG. 1) and a plurality of raised positions (one of which is shown in FIG. 1). Thigh section 46 and foot section 48 may also be pivotable about generally horizontal pivot axes.

In some embodiments, patient support apparatus 20 may be modified from what is shown to include one or more components adapted to allow the user to extend the width of patient support deck 30, thereby allowing patient support apparatus 20 to accommodate patients of varying sizes. When so modified, the width of deck 30 may be adjusted sideways in any increments, for example between a first or minimum width, a second or intermediate width, and a third or expanded/maximum width.

As used herein, the term "longitudinal" refers to a direction parallel to an axis between the head end 38 and the foot end 40. The terms "transverse" or "lateral" refer to a direction perpendicular to the longitudinal direction and parallel to a surface on which the patient support apparatus 20 rests.

It will be understood by those skilled in the art that patient support apparatus 20 can be designed with other types of mechanical constructions, such as, but not limited to, that described in commonly assigned, U.S. Pat. No. 10,130,536 to Roussy et al., entitled PATIENT SUPPORT USABLE WITH BARIATRIC PATIENTS, the complete disclosure of which is incorporated herein by reference. In another embodiment, the mechanical construction of patient support apparatus 20 may be the same as, or nearly the same as, the mechanical construction of the Model 3002 S3 bed manufactured and sold by Stryker Corporation of Kalamazoo, Michigan. This mechanical construction is described in greater detail in the Stryker Maintenance Manual for the MedSurg Bed, Model 3002 S3, published in 2010 by Stryker Corporation of Kalamazoo, Michigan, the complete disclosure of which is incorporated herein by reference. It will be understood by those skilled in the art that patient support apparatus 20 can be designed with still other types of mechanical constructions, such as, but not limited to, those described in commonly assigned, U.S. Pat. No. 7,690,059 issued to Lemire et al., and entitled HOSPITAL BED; and/or commonly assigned U.S. Pat. publication No. 2007/0163045 filed by Becker et al. and entitled PATIENT HANDLING DEVICE INCLUDING LOCAL STATUS INDICATION, ONE-TOUCH FOWLER ANGLE ADJUSTMENT, AND POWER-ON ALARM CONFIGURATION, the complete disclosures of both of which are also hereby incorporated herein by reference. The mechanical construction of patient support apparatus 20 may also take on still other forms different from what is disclosed in the aforementioned references.

Figure 2:
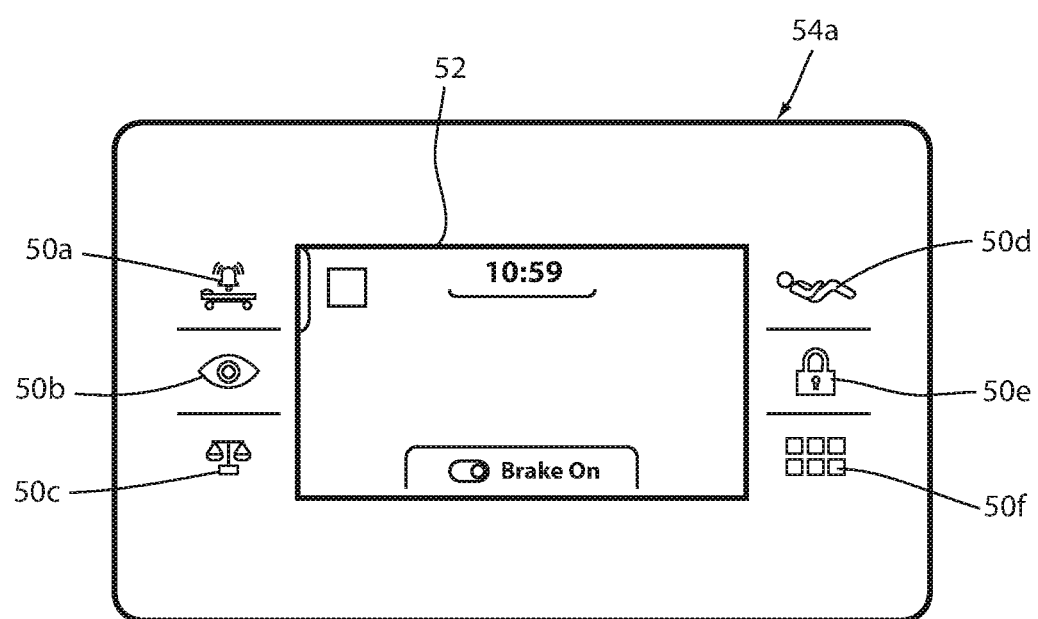
FIG. 2 is a plan view of an illustrative caregiver control panel of the patient support apparatus of FIG. 1.

Patient support apparatus 20 further includes a plurality of control panels 54 that enable a user of patient support apparatus 20, such as a patient and/or an associated caregiver, to control one or more aspects of patient support apparatus 20. In the embodiment shown in FIG. 1, patient support apparatus 20 includes a footboard control panel 54a, a pair of outer siderail control panels 54b (only one of which is visible), and a pair of inner siderail control panels 54c (only one of which is visible). Footboard control panel 54a and outer siderail control panels 54b are intended to be used by caregivers, or other authorized personnel, while inner siderail control panels 54c are intended to be used by the patient associated with patient support apparatus 20. Each of the control panels 54 includes a plurality of controls 50 (see, e.g. FIGS. 2-3), although each control panel 54 does not necessarily include the same controls and/or functionality.

Among other functions, controls 50 of control panel 54a allow a user to control one or more of the following: change a height of support deck 30, raise or lower head section 44, activate and deactivate a brake for wheels 24, arm and disarm an exit detection system and, as will be explained in greater detail below, communicate with the particular IT infrastructure installed in the healthcare facility in which patient support apparatus 20 is positioned. One or both of the inner siderail control panels 54c also include at least one control that enables a patient to call a remotely located nurse (or other caregiver). In addition to the nurse call control, one or both of the inner siderail control panels 54c also include one or more controls for controlling one or more features of one or more room devices positioned within the same room as the patient support apparatus 20. As will be described in more detail below, such room devices include, but are not necessarily limited to, a television, a reading light, and a room light. With respect to the television, the features that may be controllable by one or more controls 50 on control panel 54c include, but are not limited to, the volume, the channel, the closed-captioning, and/or the power state of the television. With respect to the room and/or night lights, the features that may be controlled by one or more controls 50 on control panel 54c include the on/off state and/or the brightness level of these lights.

Control panel 54a includes a display 52 (FIG. 2) configured to display a plurality of different screens thereon. Surrounding display 52 are a plurality of navigation controls 50a-f that, when activated, cause the display 52 to display different screens on display 52. More specifically, when a user presses navigation control 50a, control panel 54a displays an exit detection control screen on display 52 that includes one or more icons that, when touched, control an onboard exit detection system. The exit detection system is as adapted to issue an alert when a patient exit from patient support apparatus 20. Such an exit detection system may include any of the features and functions as, and/or may be constructed in any of the same manners as, the exit detection system disclosed in commonly assigned U.S. patent application 62/889,254 filed Aug. 20, 2019, by inventors Sujay Sukumaran et al. and entitled PERSON SUPPORT APPARATUS WITH ADJUSTABLE EXIT DETECTION ZONES, the complete disclosure of which is incorporated herein by reference.

When a user pressed navigation control 50b (FIG. 2), control panel 54 displays a monitoring control screen that includes a plurality of control icons that, when touched, control an onboard monitoring system built into patient support apparatus 20. Further details of one type of monitoring system that may be built into patient support apparatus 20 are disclosed in commonly assigned U.S. patent application Ser. No. 62/864,638 filed Jun. 21, 2019, by inventors Kurosh Nahavandi et al. and entitled PATIENT SUPPORT APPARATUS WITH CAREGIVER REMINDERS, as well as commonly assigned U.S. patent application Ser. No. 16/721,133 filed Dec. 19, 2019, by inventors Kurosh Nahavandi et al. and entitled PATIENT SUPPORT APPARATUSES WITH MOTION CUSTOMIZATION, the complete disclosures of both of which are incorporated herein by reference.

When a user presses navigation control 50c, control panel 54a displays a scale control screen that includes a plurality of control icons that, when touched, control the scale system of patient support apparatus 20. Such a scale system may include any of the features and functions as, and/or may be constructed in any of the same manners as, the scale systems disclosed in commonly assigned U.S. patent application 62/889,254 filed Aug. 20, 2019, by inventors Sujay Sukumaran et al. and entitled PERSON SUPPORT APPARATUS WITH ADJUSTABLE EXIT DETECTION ZONES, and U.S. patent application Ser. No. 62/885,954 filed Aug. 13, 2019, by inventors Kurosh Nahavandi et al. and entitled PATIENT SUPPORT APPARATUS WITH EQUIPMENT WEIGHT LOG, the complete disclosures of both of which are incorporated herein by reference.

When a user presses navigation control 50d, control panel 54 displays a motion control screen that includes a plurality of control icons that, when touched, control the movement of various components of patient support apparatus 20, such as, but not limited to, the height of litter frame 28 and the pivoting of head section 44. In some embodiments, the motion control screen displayed on display 52 in response to pressing control 50d may be the same as, or similar to, the position control screen 216 disclosed in commonly assigned U.S. patent application Ser. No. 62/885,953 filed Aug. 13, 2019, by inventors Kurosh Nahavandi et al. and entitled PATIENT SUPPORT APPARATUS WITH TOUCHSCREEN, the complete disclosure of which is incorporated herein by reference.

When a user presses navigation control 50e, control panel 54a displays a motion lock control screen that includes a plurality of control icons that, when touched, control one or more motion lockout functions of patient support apparatus 20. Such a motion lockout screen may include any of the features and functions as, and/or may be constructed in any of the same manners as, the motion lockout features, functions, and constructions disclosed in commonly assigned U.S. patent application Ser. No. 16/721,133 filed Dec. 19, 2019, by inventors Kurosh Nahavandi et al. and entitled PATIENT SUPPORT APPARATUSES WITH MOTION CUSTOMIZATION, the complete disclosures of both of which are incorporated herein by reference.

When a user presses on navigation control 50f, control panel 54a displays a menu screen that includes a plurality of menu icons that, when touched, bring up one or more additional screens for controlling and/or viewing one or more other aspects of patient support apparatus 20. Such other aspects include, but are not limited to, diagnostic and/or service information for patient support apparatus 20, mattress control and/or status information, configuration settings, and other settings and/or information. One example of a suitable menu screen is the menu screen 100 disclosed in commonly assigned U.S. patent application Ser. No. 62/885,953 filed Aug. 13, 2019, by inventors Kurosh Nahavandi et al. and entitled PATIENT SUPPORT APPARATUS WITH TOUCHSCREEN, the complete disclosure of which is incorporated herein by reference.

For all of the navigation controls 50a-f (FIG. 2), screens other than the ones specifically mentioned above may be displayed on display 52 in other embodiments of patient support apparatus 20 in response to a user pressing these controls. Thus, it will be understood that the specific screens mentioned above are merely representative of the types of screens that are displayable on display 52 in response to a user pressing on one or more of navigation controls 50a-f. It will also be understood that, although navigation controls 50a-f have all been illustrated in the accompanying drawings as dedicated controls that are positioned adjacent display 52, any one or more of these controls 50a-f controls alternatively be touchscreen controls that are displayed at one or more locations on display 52. Still further, although controls 50a-f have been shown herein as buttons, it will be understood that any of controls 50a-f could also, or alternatively, be switches, dials, or other types of non-button controls.

Figure 3:
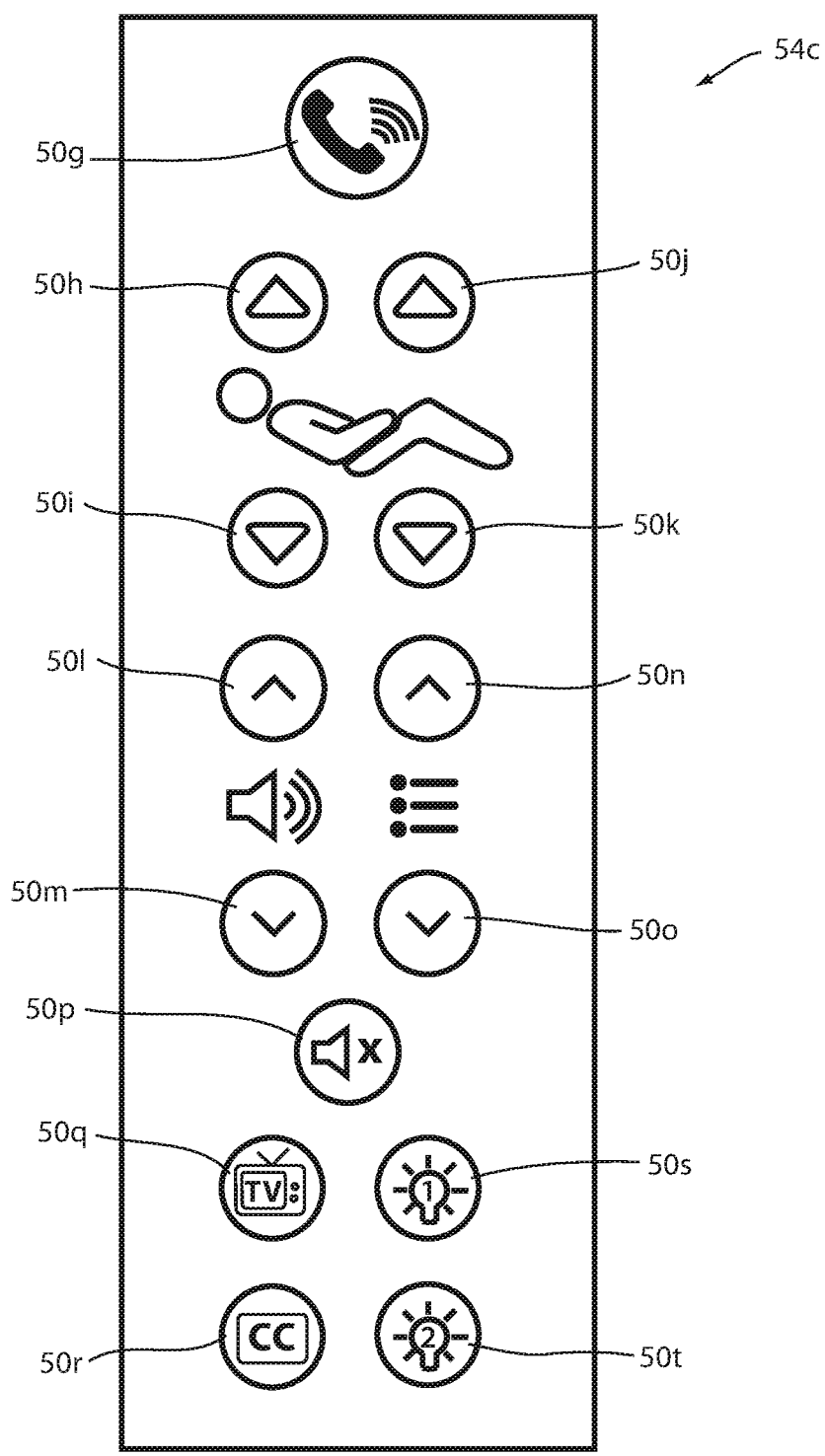
FIG. 3 is a plan view of an illustrative patient control panel of the patient support apparatus of FIG. 1.

FIG. 3 illustrates one example of a patient control panel 54c that may be incorporated into patient support apparatus 20 and positioned at a location on patient support apparatus 20 that is convenient for a patient to access while supported on support deck 30, such as on an interior side of one of the siderails 36. Control panel 54c includes a plurality of controls 50g-t that are intended to be operated by a patient. A nurse call control 50g, when pressed by the patient, sends a signal to a nurse call system requesting that a remotely positioned nurse talk to the patient. A Fowler-up control 50h, when pressed by the patient, causes a motorized actuator onboard patient support apparatus 20 to raise Fowler section 44 upwardly. A Fowler-down control 50i, when pressed by the patient, causes the motorized actuator to lower Fowler section 44 downwardly. A gatch-up control 50j, when pressed by the patient, causes another motorized actuator to raise a knee section of support deck 30, while a gatch-down control 50k causes the motorized actuator to lower the knee section of support deck 30.

A volume-up control 50l, when pressed by the patient, causes patient support apparatus 20 to send a signal to an in-room television instructing it to increase its volume, while a volume down control 50m, when pressed, causes patient support apparatus 20 to send a signal to the television instructing it to decrease its volume. A channel-up control 50n, when pressed by the patient, causes patient support apparatus 20 to send a signal to the television instructing it to increase the channel number, while a channel-down control 50o, when pressed, causes patient support apparatus 20 to send a signal to the television instructing it to decrease the channel number.

A mute control 50p, when pressed, causes patient support apparatus 20 to send a signal to the television instructing it to either mute itself or unmute itself, depending upon whether the television is currently muted or unmuted. In other words, mute control 50p is a toggle control that alternatingly sends mute and unmute commands to the television when it is pressed.

Power control 50q is a toggle control that, when pressed, sends a signal to the television to either turn on or turn off, depending upon the television's current power status. Closed-captioning control 50r is another toggle control that, when pressed, sends a signal to the television to either turn on its closed-captioning feature or to turn off its closed captioning feature, depending upon whether the closed-captioning feature is currently on or off.

Control 50s is a toggle control that, when pressed, sends a signal to a first light to either turn on or turn off, depending upon the current state of that first light. Control 50t is another toggle control that, when pressed, sends a signal to a second light to either turn on or turn off, depending upon the current state of that second light. In some embodiments, the first light is a reading light and the second light is a room light, both of which are positioned off-board the patient support apparatus 20.

It will be understood that not only the number of controls 50 on control panel 54c, but also the functions of the controls 50 on control panel 54c, the layout of the controls 50 on control panel 54c, and/or other aspects of control panel 54c may be modified from what is shown in FIG. 3. In some embodiments, control panel 54c is implemented on a pendant controller that includes a cable that is plugged into a port on patient support apparatus 20. Still other manners of implementing control panel 54c are also possible.

Figure 4:
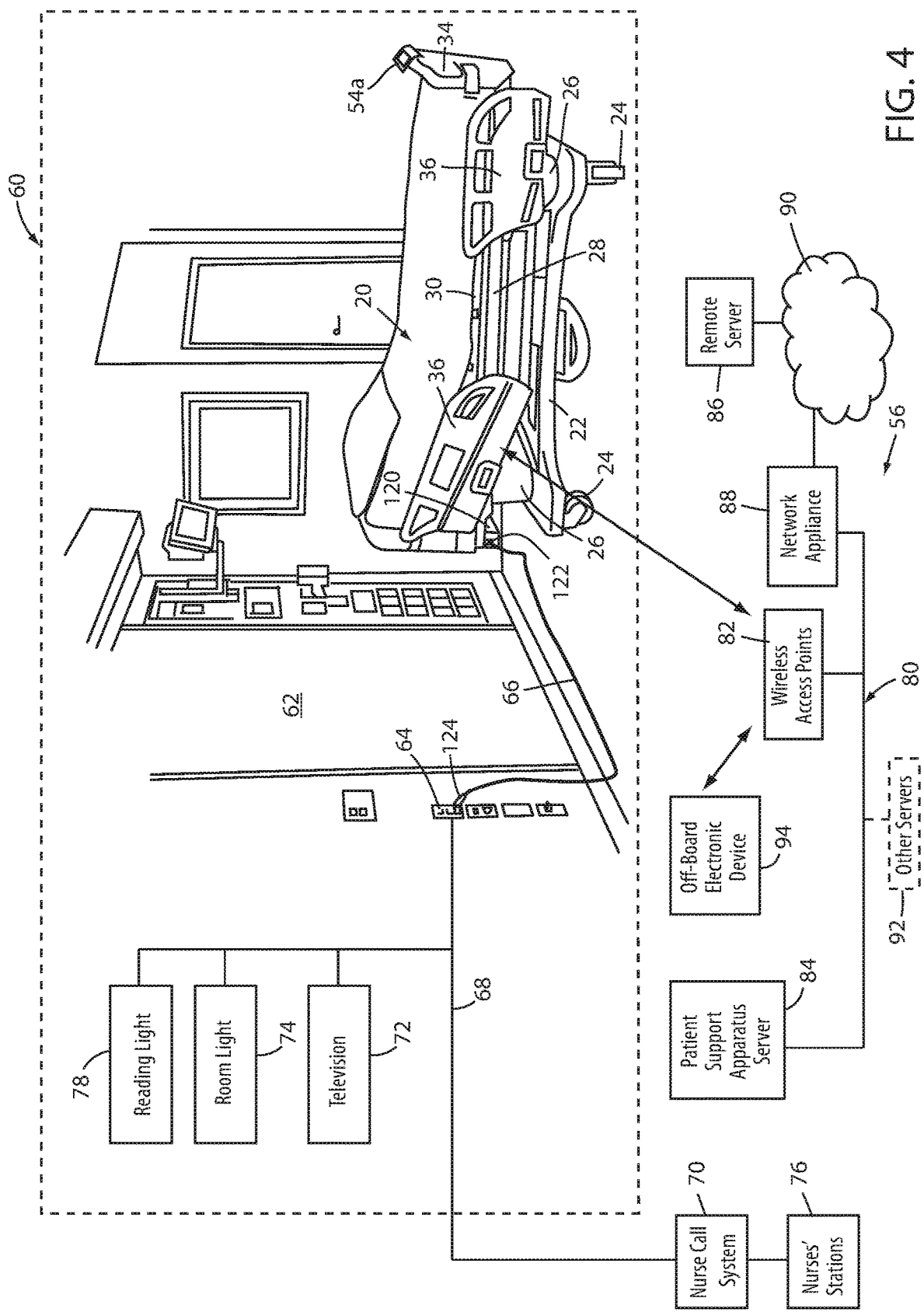
FIG. 4 is a diagram of the patient support apparatus of FIG. 1 shown coupled to the IT infrastructure of a healthcare facility in a first manner.

FIG. 4 illustrates patient support apparatus 20 positioned in a typical room 60 of a conventional healthcare facility 56. As shown therein, room 60 includes a headwall 62 into which a conventional communications outlet 64 is physically integrated. Communications outlet 64 is adapted to receive a nurse call cable 66 that physically connects at its other end to patient support apparatus 20. As will be discussed in greater detail below, nurse call cable 66 allows patient support apparatus 20 to communicate with a nurse call system, and one or more room devices positioned within room 60.

Communication outlet 64 is electrically coupled to one or more cables or other conductors 68 that electrically couple the communication outlet 64 to a nurse call system 70 and one or more room devices, such as a television 72, a room light 74, and/or a reading light 78. Conductors 68 are typically located behind headwall 62 and not visible. In some healthcare facilities, conductors 68 may first couple to a room interface circuit board that includes one or more conductors 68 for electrically coupling the room interface circuit board to room devices 72, 74, 78 and/or nurse call system 70. Still other communicative arrangements for coupling communication outlet 64 to nurse call system 70 and/or one or more room devices 72, 74, 78 are possible.

Room devices 72, 74, 78 are conventional room devices that are typically present in a conventional hospital room. In most cases, the particular brand and model of the television 72 and/or lights 74, 78 will vary from healthcare facility to healthcare facility, and may vary from room to room within the same healthcare facility. The different models and/or brands of televisions 72, room lights 74, and/or reading lights 78 are often controlled in different manners. For example, the signals that are input into a first brand of television in order to change a channel may require a first voltage level, while the signals that are input into a second brand of television in order to change the channel may require a second voltage level. Still further, apart from differences in voltage levels, the sequence of bits and/or other information that is sent to a television to change the channel, for example, may vary from brand to brand, or from model to model. Still other aspects of the control of the television 72 and/or lights 74, 78 may vary from brand to brand and/or from model to model. Thus, in order for a patient to properly control the television 72 and/or lights 74, 78 using one of the patient control panels 54c, patient support apparatus 20 and/or another device in communication with patient support apparatus 20 need to be properly configured to match the particular television 72 and/or lights 74, 78 that are positioned in the same room as the patient support apparatus 20. As will be discussed in greater detail below, this configuration data is stored, in at least one embodiment, in off-board headwall units, and patient support apparatus 20 may be configured to both allow a user to use patient support apparatus 20 as a conduit for changing the configuration data stored in the off-board headwall unit, and/or patient support apparatus 20 may be used as a conduit for allowing a remotely positioned person (e.g. a caregiver) to remotely control television 72, room light 74, and/or reading light 78 through patient support apparatus 20 and its associated off-board headwall unit.

Returning to FIG. 4, nurse call cable 66 enables patient support apparatus 20 to communicate with nurse call system 70 and/or room devices 72, 74, 78. A patient supported on patient support apparatus 20 who activates a nurse call control (e.g. 50g; see FIG. 3) on patient support apparatus 20 causes a signal to be conveyed via nurse call cable 66 to the nurse call system 70, which forwards the signal to a one or more remotely located nurses (e.g. nurses at one or more nurses' stations 76). If the patient activates one or more room device controls (e.g. controls 50l-t; see FIG. 3), one or more signals are conveyed via nurse call cable 66 to the room devices 72, 74, 78 that changes one or more features of these devices (e.g. the volume, channel, on/off state, etc.).

As is also shown in FIG. 4, patient support apparatus 20 is further configured to communicate with a local area network 80 of the healthcare facility 56. In the embodiment shown in FIG. 4, patient support apparatus 20 includes a wireless network transceiver 126 that communicates wirelessly with local area network 80. It will be understood, however, that in some embodiments, patient support apparatus 20 is adapted to communicate with network 80 via a wired connection, such as an Ethernet cable that plugs into an Ethernet port (e.g. an RJ-45 style port, an 8P8C port, etc.) built into patient support apparatus 20. In other embodiments, patient support apparatus 20 includes a wireless network transceiver, such as, but not limited to, a WiFi transceiver (e.g. IEEE 802.11) that wirelessly communicates with one or more wireless access points 82 of local area network 80. In still other embodiments, patient support apparatus 20 includes both a wired port for communicating with network 80 via a wired connection and a wireless connection for communicating with network 80.

Patient support apparatus 20 is configured to communicate with one or more servers on local area network 80 of healthcare facility 56. One such server is a patient support apparatus server 84. Patient support apparatus server 84 is adapted, in at least one embodiment, to receive status information from patient support apparatuses 20 positioned within healthcare facility 56 and distribute this status information to caregivers, other servers, and/or other software applications. In some embodiments, patient support apparatus server 84 is configured to communicate at least some of the status data received from patient support apparatuses 20 to a remote server 86 that is positioned geographically remotely from healthcare facility 56. Such communication may take place via a network appliance 88, such as, but not limited to, a router and/or a gateway, that is coupled to the Internet 90. The remote server 86, in turn, is also coupled to the Internet 90, and patient support apparatus server 84 is provided with the URL and/or other information necessary to communicate with remote server 86 via the Internet connection between network 80 and server 86.

It will be understood that the architecture and content of local area network 80 will vary from healthcare facility to healthcare facility, and that the example shown in FIG. 4 is merely one example of the type of network a healthcare facility may be employ. Typically, additional servers 92 will be hosted on network 80 and one or more of them may be adapted to communicate with patient support apparatus server 84. For example, an electronic health record server will typically be present in any healthcare facility, and in some cases may be in communication with patient support apparatus server 84 in order to receive patient data that is to be recorded in a patient's health record (e.g. weight readings taken from the scales built into patient support apparatuses 20; therapies provided to patients using a power mattress 42 onboard patient support apparatuses 20, etc.). Local area network 80 will also typically allow one or more electronic devices 94 to access the local area network 80 via wireless access points 82. Such electronic devices 94 include, but are not limited to, smart phones, tablet computers, portable laptops, desktop computers, and other types of electronic devices that include a WiFi capability and that are provided with the proper credentials (e.g. SSID, password, etc.) to access network 80.

In at least one embodiment, patient support apparatus server 84 is configured to communicate with one or more electronic devices 94 in order to allow such devices 94 to control one or more of the room devices 72, 74, 78 using one or more patient support apparatuses 20 as communication intermediaries. Thus, for example, if a user of an electronic device 94 wishes to turn off a television 72 positioned with a particular room, he or she can access patient support apparatus server 84 using electronic device 94 and its connection to local area network 80 via wireless access point 82. Patient support apparatus sever 84 executes an application that presents an authorized user of electronic device 94 with a set of menu options for controlling room devices 72, 74, 78 in at least one room 60, if not many or all, of the rooms 60 contained within healthcare facility 56. The user of electronic device 94 can then select the desired menu option on the screen of their electronic device 94 to turn on a room or reading light 74, 78, turn off a room or reading light 74, 78, turn on/off television 72, change the channel and/or volume of television 72, and/or change another aspect of television 72 (e.g. turn on/off closed captioning). The menu includes a selection of not only which rooms within healthcare facility 56 to control room devices 72, 74, 78 but also which bays within those rooms that include multiple bays (e.g. those rooms that are intended to house multiple patient support apparatuses 20) to control the corresponding room devices 72, 74, 78. The operation of this remote control of room devices via electronic device(s) 94 is described in more detail below with respect to FIG. 5.

Figure 5:
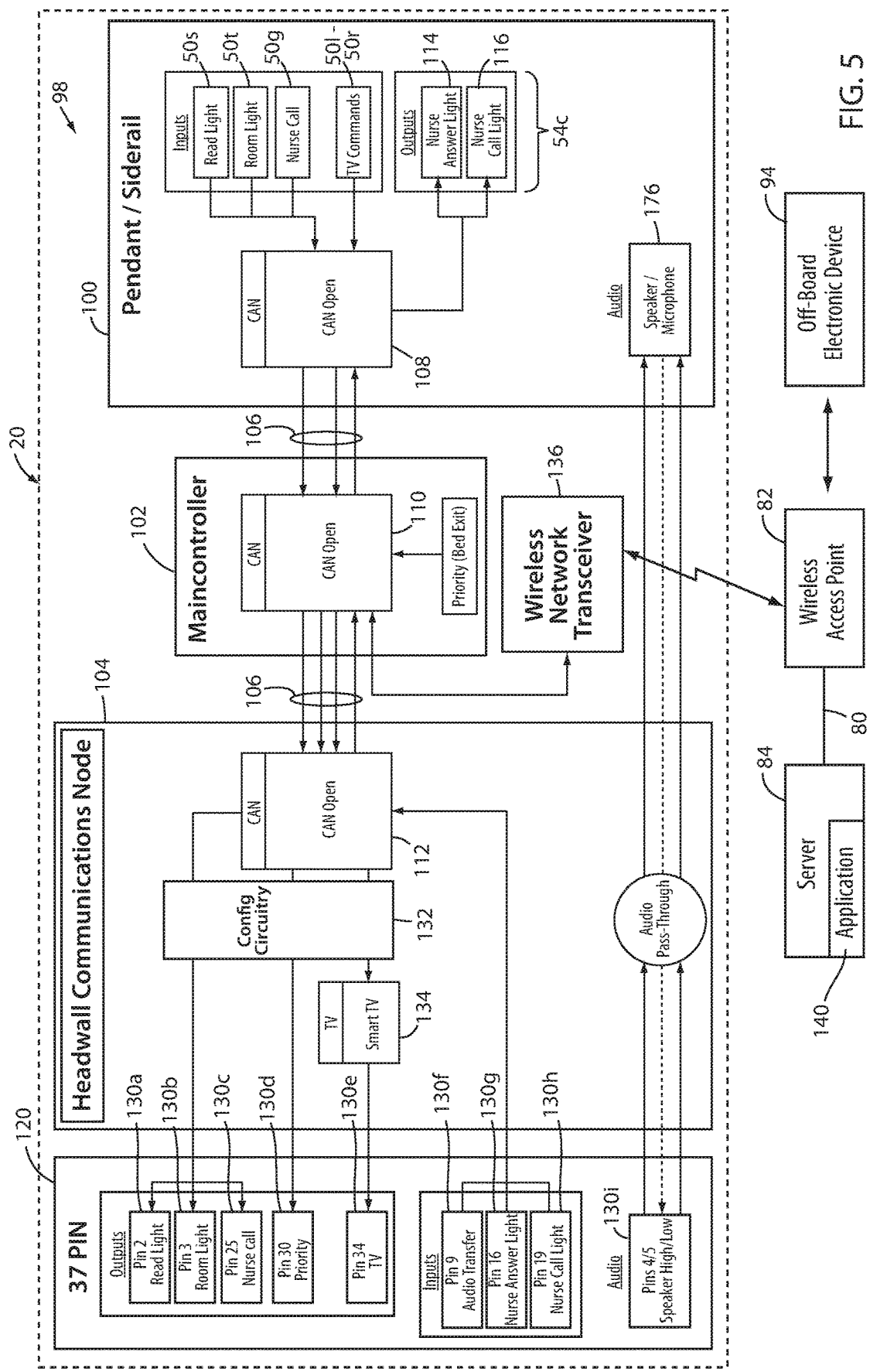
FIG. 5 is a diagram of the control system of the patient support apparatus of FIG. 1.

FIG. 5 depicts in more detail a control system 98 onboard patient support apparatus 20. Control system 98 includes a pendant/siderail node 100, a main node 102, and a headwall communication node 104. Each of nodes 100, 102, and 104 are part of an onboard embedded communications network 106. That is, each node 100-104 is communicatively coupled to each other via an onboard communication network 106, which, in the illustrated embodiment, is a Controller Area Network (CAN). It will be understood that other types of communication may be used in other embodiments (e.g. one or more of the following: an I-Squared-C bus, a Local Interconnect Network (LIN) bus, Firewire, RS-232, RS-485, a Universal Serial Bus (USB), Ethernet, and/or a Serial Peripheral Interface (SPI) bus, as well as non-bus communication). In still other embodiments, control system 98 may be implemented with fewer or greater numbers of nodes (including only a single node). Still other modifications are possible for control system 98, including, but not limited to, the elimination and/or replacement of onboard network 106.

Pendant/siderail node 100 includes pendant/siderail controller 108; main node 102 includes a main controller 110, and headwall communications node 104 includes a headwall communications controller 112. Each of controllers 108, 110, and 112 may take on a variety of different forms. In the illustrated embodiment, each of controllers 108, 110, and 112 is implemented as a conventional microcontroller. However, controllers 108, 110, and 112 may be modified to use a variety of other types of circuits—either alone or in combination with one or more microcontrollers—such as, but not limited to, any one or more microprocessors, field programmable gate arrays, systems on a chip, volatile or nonvolatile memory, discrete circuitry, and/or other hardware, software, or firmware that is capable of carrying out the functions described herein, as would be known to one of ordinary skill in the art. Such components can be physically configured in any suitable manner, such as by mounting them to one or more circuit boards, or arranging them in other manners, whether combined into a single unit or distributed across multiple units. The instructions followed by controllers 108, 110, and 112 when carrying out the functions described herein, as well as the data necessary for carrying out these functions, are stored in a corresponding memory (not shown) that is accessible to that particular controller 108, 110, and 112.

In some embodiments of patient support apparatus 20, siderail/pendant node 100 is physically positioned inside one or both of the head end siderails 36 of patient support apparatus 20 and includes patient control panel 54*c*. In other embodiments, pendant/siderail node 100 is physically positioned inside of a pendant that is coupled, typically via a cable, to patient support apparatus 20. In still other embodiments, patient support apparatus 20 may be configured with one or more pendant/siderail nodes 100 positioned inside of siderails 36 and also a pendant controller that is plugged into a pendant port on patient support apparatus 20 (and in communication with embedded network 106).

Control panel 54*c* of pendant/siderail node 100 includes a plurality of controls 50. Although FIG. 5 only illustrates controls 50*g* and 50*l* through 50*r*, it will be understood that pendant/siderail node 100 may include any or all of the controls 50 shown in FIG. 3. Pendant/siderail node 100 may also include additional controls 50 beyond what is shown in FIGS. 3 and/or 5, and/or it may include a selection of controls 50 that is different from the sets of controls 50 shown in FIGS. 3 and/or 5.

As shown in FIG. 5, pendant/siderail node 100 includes a nurse answer light 114 and a nurse call light 116. Pendant/siderail controller 108 is configured to light up nurse call light 116 when the user presses nurse call control 50*g* and receives an acknowledgement from the nurse call system 70 that a nurse call request has been successfully communicated to the nurse call system. Controller 108 is configured to light up nurse answer light 114 when a nurse actually responds to the nurse call placed by the user pressing on nurse call control 50*g*.

When a user presses on, or otherwise activates, any of controls 50 on control panel 54*c*, the pressing of those controls is detected by pendant/siderail controller 108. In response thereto, controller 108 sends a message on network 106 to headwall communication node 104 indicating which control(s) 50 were pressed. In some embodiments, the message is addressed (or otherwise identified) as being intended for headwall communication node 104 so that main node 102 does not need to act as a communications intermediary between node 100 and node 104. In other embodiments, controller 108 may send the message to node 104 via one or more intermediary nodes, such as main node 102. However the message travels to node 104, headwall communication controller 112 is programmed to receive the message and convey it in the appropriate manner to a headwall interface 120 incorporated into patient support apparatus 20.

Headwall interface 120 (FIG. 5) is an interface into which a conventional 37-pin nurse call cable, such as nurse call cable 66, is adapted to plug. That is, interface 120 is adapted to receive a 37-pin connector coupled to one end of a conventional nurse call cable 66. Nurse call cable 66 includes a first end having a first connector 122 (FIG. 4) and a second end having a second connector 124 (FIG. 4). First connector 122 is adapted to be plugged into headwall interface 120 positioned on patient support apparatus 20. Second connector 124 is adapted to be plugged into communication outlet 64. In many healthcare facilities 56, communication outlet 64 is configured as a 37-pin receptacle, although it will be understood that the principles of the present disclosure may be applied to communication outlets 64 and/or cables 66 having different numbers of pins.

Figure 16:
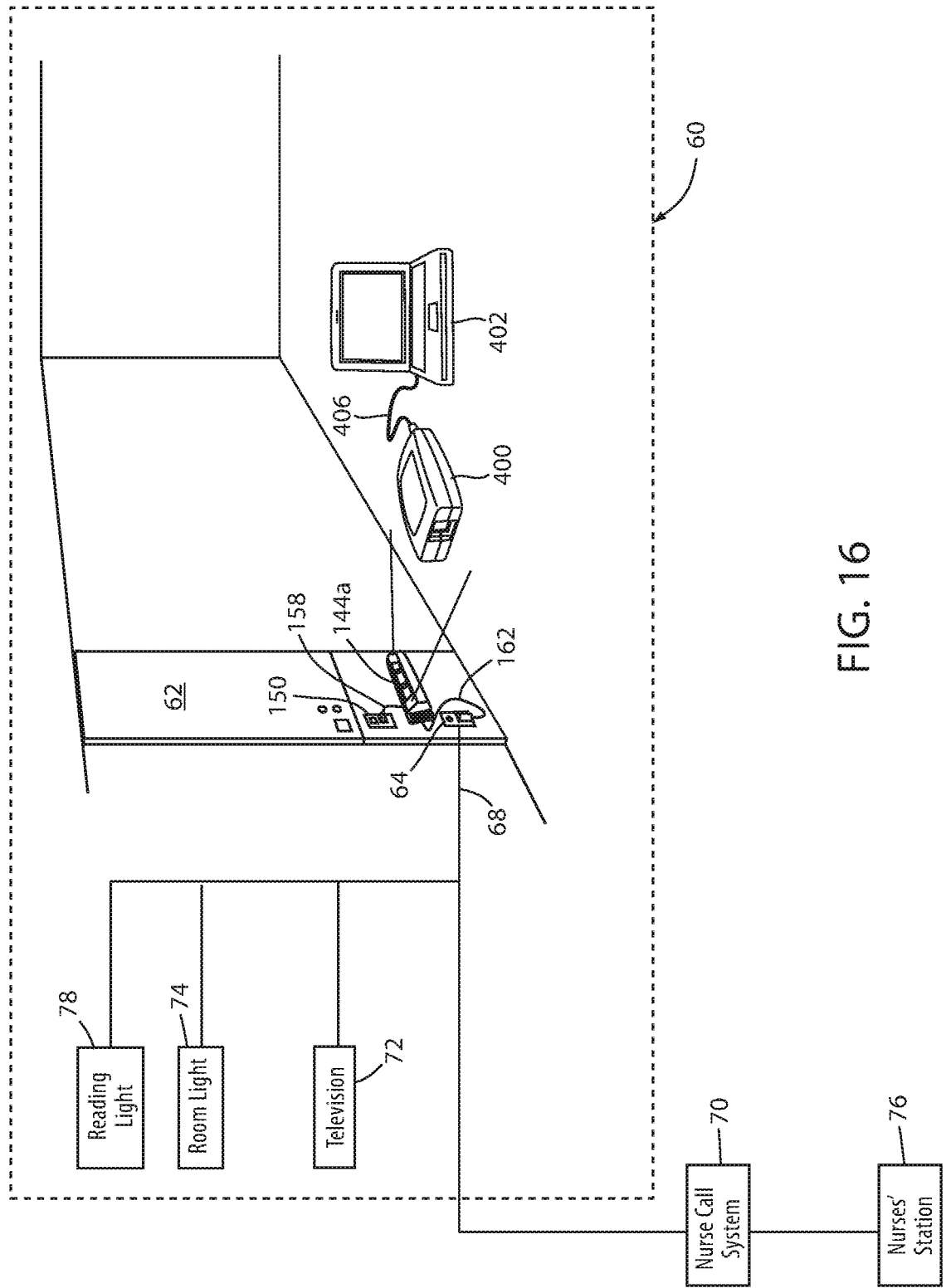
FIG. 16 is a diagram of a portable configuration tool shown in communication with a headwall unit that is coupled to the IT infrastructure of a healthcare facility.
Figure 17:
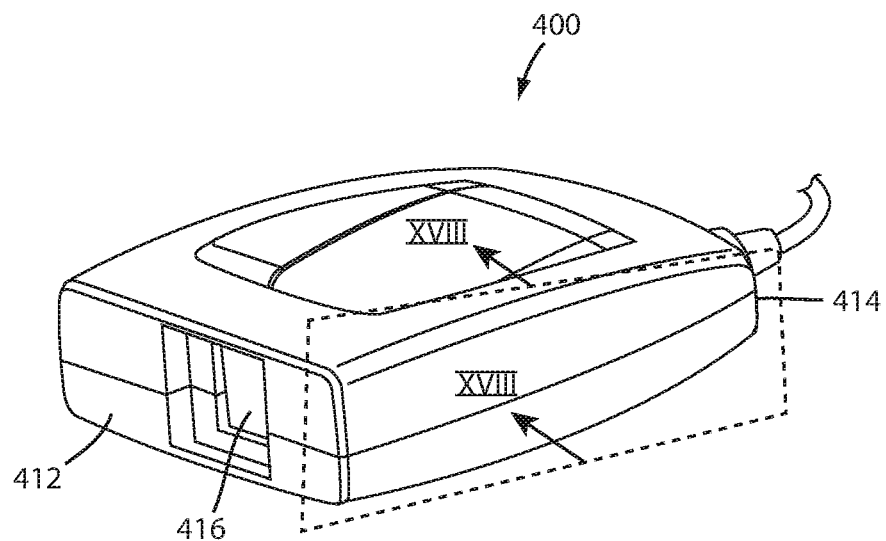
FIG. 17 is a perspective view of the configuration tool of FIG. 16.
Figure 30:
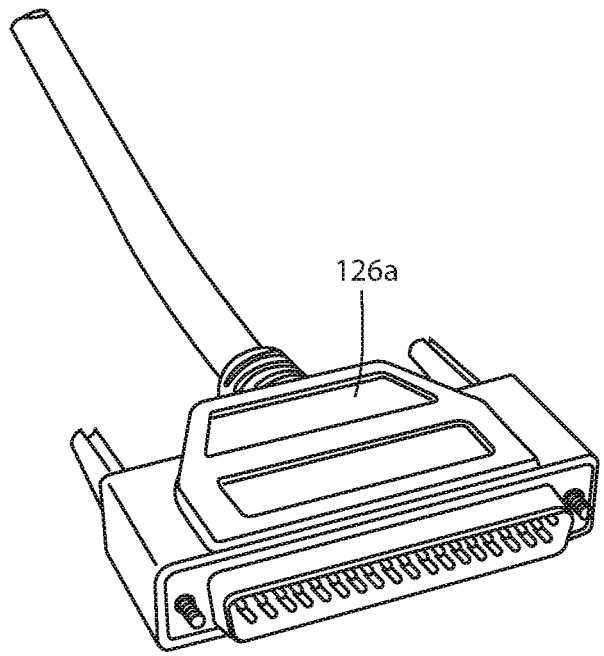
FIG. 30 is a perspective view of a prior art 37-pin male cable connector.
Figure 31:
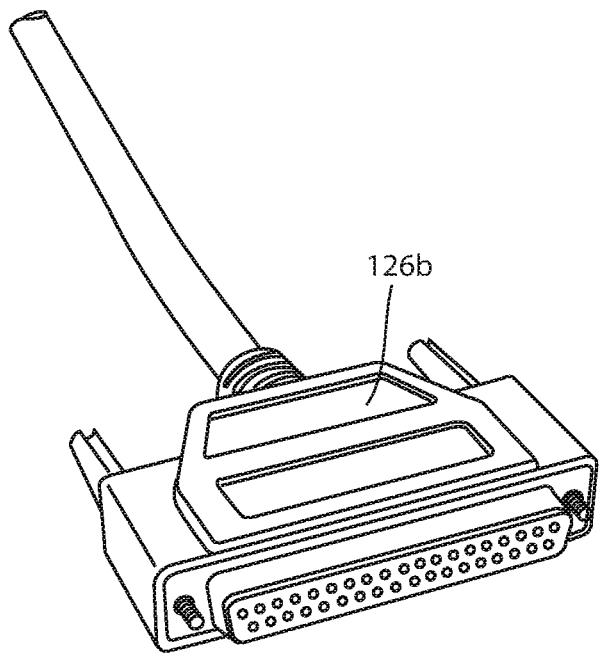
FIG. 31 is a perspective view of a prior art 37-pin female cable connector.

One example of a male 37-pin connector 126a that may be used as first or second connector 122 or 124 is shown in FIG. 30. One example of a female 37-pin connector 126b that may be used as first or second connector 122 or 124 is shown in FIG. 31. Other types of 37-pin connectors may also be used, depending upon the configuration of communication outlet 64. Still further, in some healthcare environments, communication outlet 64 includes fewer pins and/or has an arrangement of pins that is shaped differently from what is shown in FIGS. 16 and 17. Patient support apparatus 20 may be adapted to communicate with all of these different types of communication outlets 64 via an appropriately selected cable (e.g. one with the proper connectors 122, 124 on its ends).

Headwall interface 120 (FIG. 5) includes a plurality of pins 130 that are adapted to electrically communicate with corresponding pins on nurse call cable 66. In some embodiments, pins 130 of headwall interface 120 may comprise female receptacles adapted to electrically couple to pins of cable 66 when cable 66 includes a male connector 122, or they may be pins 130 adapted to electrically couple to female receptacles when cable 66 includes a female connector 122. Pins 130 may alternatively be implemented as any type of metal, or electrically conductive, contact for establishing electrical communication between patient support apparatus 20 and nurse call cable 66.

Each pin 130 of headwall interface is adapted to convey certain information from patient support apparatus 20 to nurse call system 70 and/or room devices 72, 74, or vice versa. FIG. 32 shows one illustrative pin assignment for a conventional 37-pin connector. As can be seen in FIG. 32, each pin conveys different information. For example, pin 3 is used to convey information to room light 74 indicating that the occupant of patient support apparatus 20 has pressed a control (e.g. 50t) on patient support apparatus 20 to turn on or turn off the room light 74 in the particular room in which patient support apparatus 20 is located. In many instances, pin 3 is electrically tied to pin 27 and patient support apparatus 20 sends commands to room light 74 to turn on or turn off based on whether the electrical connection between pins 3 and 27 is open or closed. For some room lights 74, an open circuit between pins 3 and 27 indicates that the room lights should be turned off and a closed circuit between pins 3 and 27 indicates that the room light 74 should be turned on. For other room controls, the opposite may be true. That is, for some other room lights 74, an open circuit between pins 3 and 27 indicates the room light 74 should be turned on and a closed circuit between pins 3 and 27 indicates the room light 74 should be turned off.

As another example, pin 2 (FIG. 32) is commonly used to control a reading light 78. When the occupant of patient support apparatus 20 presses a control (e.g. 50s) on control panel 54c of patient support apparatus 20, controller 108 sends a message to headwall communications controller 112, and controller 112 reacts to the message by changing a voltage and/or by changing an open or closed state of an electrical circuit between pins 2 and 27 of headwall interface 120. For some reading lights 78, an open circuit between pins 2 and 27 indicates that the reading light 78 should be turned off and a closed circuit between pins 2 and 27 indicates that the reading light 78 should be turned on. For other reading lights 78, the opposite may be true.

When an occupant of patient support apparatus 20 presses on any of television controls 50l-r on control panel 54c, pendant/siderail controller 100 sends a corresponding message over communication network 106 to headwall communications node 104 (FIG. 5). In response to receiving this message, headwall communication controller 112 outputs a corresponding signal on pins 33 and 34 of headwall interface 120. Because these pins are electrically coupled to the television 72 within room 60 via nurse call cable 66, communications outlet 64, and conductors 68, the television reacts appropriately in response to the commands entered by the occupant using controls 50l-r.

In order for headwall communications controller 112 to determine how to properly respond to the messages it receives from pendant/siderail controller 108 in response to a user pressing on one or more of the controls 50 used to control television 72, room light 74, and/or reading light 78, controller 112 utilizes configuration circuitry 132 (FIG. 5). Configuration circuitry 132 is set up to maintain the pins 130 in their appropriate neutral state until a user presses on a corresponding control 50, as well as to apply the proper voltage to each of pins 130 in response to the user pressing the corresponding control 50. In some embodiments, configuration circuitry 132 includes one or more dip switches, or other devices, that are configurable to match the room device 72, 74, 78, and nurse call system 70 of the healthcare facility 56 in which the patient support apparatus 20 is installed. In other embodiments, configuration circuitry 132 may include onboard non-volatile memory that stores the necessary configuration data, along with appropriate circuitry to utilize this stored data to implement the necessary state changes in pins 130. In at least one embodiment, configuration circuitry 132 is implemented in any of the manners disclosed in commonly assigned U.S. patent publication 2018/0293849 published on Oct. 11, 2018, entitled PATIENT SUPPORT APPARATUSES WITH RECONFIGURABLE COMMUNICATION, the complete disclosure of which is incorporated herein by reference. Still other manners of implementing configuration circuitry 132 may also or alternatively be implemented according to the present disclosure.

Configuration circuitry 132 may, in some embodiments, include smart television control circuitry 134 (FIG. 5) that stores the sequence of signals that are to be sent for each brand (or a plurality of brands) of televisions that are necessary to control that television's channel, volume, mute, closed captioning, power state, HDMI input, etc. In such cases, either headwall communications controller 112 and/or configuration circuitry 132 informs smart TV control circuit 134 which brand of television (and, in some cases, which model) is in room 60, and smart TV control circuit 134 thereafter determines the correct signals to send in response to commands received from headwall communications controller 112 (which, in turn, receives the commands from control panel 54c, or as discussed in greater detail below, from off-board electronic device 94). The knowledge of which brand of television 72 is present in the room is conveyed to configuration circuitry and/or headwall communications controller 112 either by setting one or more dipswitches that are part of configuration circuitry 132, or by entering this information via one of the control panels (e.g. control panel 54a). In the latter case, the control panel 54 forwards the television brand information to headwall communications controller 112 over network 106.

In addition to room devices 72, 74, 78, the various pins 130 of headwall interface 120 also communicate information to nurse call system 70. This information is likewise often communicated by opening or closing the electrical connection between two pins. For example, when a patient presses a nurse call control, such as nurse call control 50g (FIG. 3), the electrical connection between pins 19 and 28 is typically changed by headwall communications controller 112 and configuration circuitry 132. These pins indicate to the nurse call system 70 that a nurse call request has been initiated by the occupant of patient support apparatus 20. Depending upon the particular nurse call system 70, it responds by illuminating one or more lights (e.g. a light in the hallway of the healthcare facility and/or a light at one or more of the nurses' stations 76). For some nurse call systems, the neutral state of the electrical connection between pins 19 and 28 should be open, while in other nurse call systems, the neutral state should be closed. Accordingly, configuration circuitry 132 is configured to properly match the particular nurse call system 70 with which it is going to communicate.

The term "neutral state" used herein refers to the state of the electrical connection between two pins 130 when no condition has been detected, or no desired action has been requested by the patient, caregiver, or patient support apparatus 20 itself. Thus, for example, for the pin that communicates a nurse call signal to the nurse call system (e.g. pin 30), the neutral state of that pin refers to its state when no nurse call control (e.g. 50g) has been pressed. In some nurse call systems, this neutral state will be closed with respect to a ground pin (e.g. common pin 31), while for other nurse call systems, this neutral state may be open with respect to the ground (e.g. common pin 31). As another example, for the pin that communicates a change to room light 74, the neutral state of pin 3 may refer to the electrical state of pin 3 relative to pin 27 (e.g. open or closed) when no change in room light 72 is being requested by a user (e.g. the patient has not pressed, or otherwise activated, control 50t).

Control system 98 also includes a wireless network transceiver 136 adapted to wirelessly communicate with one or more of the wireless access points 82 of the local area network 80 of the healthcare facility 56. As was noted, in some embodiments, transceiver 136 may be a conventional WiFi transceiver, although other types of wireless transceivers may be used. As was also noted previously, patient support apparatus 20 may also, or alternatively, include a wired transceiver (not shown) for communicating with network 80 via a wired connection.

Main controller 110 is adapted to receive commands from wireless network transceiver 136 that are intended to control one or more of room devices 72, 74, and/or 78. In response to those commands, main controller 110 executes the same or similar actions as does pendant/siderail controller 108 when it receives commands from controls 50. That is, main controller 110 forwards one or messages addressed to headwall communications controller 112 instructing it to control the corresponding pin(s) 130 in a manner corresponding to the received message. Thus, for example, if a remote user sends a command to turn on room light 74 to patient support apparatus, wireless network transceiver 136 forwards the command to main controller 110 which, in turn forwards it to headwall communication controller 112. Headwall communication controller 112, in turn, instructs configuration circuitry 132 to change the voltage and/or state of pin 3 such that the room light 74, which is in electrical communication with pin 3, turns on. In this manner, patient support apparatus 20 acts as a communication conduit to allow a remotely positioned person to remotely control any of room devices 72, 74, and/or 78.

In at least one embodiment, in order for a remotely positioned person to send a command to control any of room devices 72, 74, and/or 76 to patient support apparatus 20, the remotely positioned person must first log into a remote control application 140 that is executed by patient support apparatus server 84. The remotely positioned user is able to log into this remote control application 140 by using any off-board electronic device 94 that is able to access local area network 80 and server 84 (and that provides the necessary logon credentials to remote control application 140). Once logged on, remote control application 140 provides one or more screens that are displayed on the user's associated electronic device 94 that include controls for controlling room devices 72, 74, and/or 78. These remote controls, in some cases, are graphic icons that looks the same as, or similar to, the way controls 50 of control panel 54c look, thereby providing the remote user with the same visual image that a local user of control panel 54c would see. These remote controls may be the same set of controls 50 that are present on control panel 54c, a subset of those controls 50, a mix of some of the same controls and some different controls, or still other variations.

The remote controls that are presented to an authorized user of remote control application 140 may be visual controls displayed on a screen of electronic device 94 that must be touched by the user to remotely control room devices 72, 74, or 78 (if electronic device 94) includes a touch screen, or they may be visual controls that are displayed on a screen of electronic device 94 that are activated in a different manner (e.g. by selecting the control with a mouse and then mouse-clicking on the selected control, by pressing one or more keys on a keyboard or keypad, etc.). However presented, the activation of a selected control by the user of electronic device 94 causes electronic device 94 to send a signal to server 84 and remote control application 140. If off-board electronic device 94 is wirelessly coupled to network 80, this is signal is sent by electronic device 94 to wireless access point 82, which then forwards it to server 84 and application 140 over network 80. If off-board electronic device 94 is coupled to network 80 via a wired connection, this signal is routed to server 84 and application 140 directly over network 80.

In response to receiving this remote control signal from electronic device 94, application 140 sends a corresponding command to patient support apparatus 20 via network 80, wireless access point 82 (in the example shown in FIG. 5) and network transceiver 136. As noted above, wireless network transceiver 136 forwards this command to controller 110, which in turn forwards it to headwall communication controller 112. Headwall communication controller 112 then instructs configuration circuitry 132 (and/or smart television control circuitry 134) to change the electrical state of, and/or place the necessary signals on, the corresponding pins 130 that will carry out the command received from remote control application 140. These state changes and/or signals are conveyed from the pins of headwall interface 120 to the pins of nurse call cable 66, which in turn transfers the state changes and/or signals to headwall communication outlet 64. Headwall communication outlet 64 then forwards these state changes and/or signals to the room device(s) 72, 74, and/or 78 via conductors 68.

For example, if a user of remote control application 140 activates a remote control to increase the channel on television 72 in, say, room 402 of healthcare facility 56, the electronic device 94 that the user is using sends a signal to remote control application 140 informing application 140 that the user has requested that television 72 in room 402 increase its channel. In response, application 140 sends a message to the patient support apparatus 20 in room 402 instructing it to increase the channel of the television 72 in that room. This is communicated to that patient support apparatus 20 via network transceiver 136, which in turn forwards it to main controller 110. Main controller 110 then forwards it to headwall communications controller 112. Headwall communications controller 112 instructs configuration circuitry 132 and/or smart television control circuitry 134 to output the correct voltage signals on pin 34 that will cause the particular brand of television in room 402 to increase its channel. Those voltage signals are conveyed via pin 34 to nurse call cable 66 which, in turn, conveys them to television 72 via communications outlet 64 and conductors 68. Television 72 then increases its channel.

In some embodiments, remote control application 140 is incorporated into a larger software application that performs additional functions beyond merely allowing a user to remotely control room devices 72, 74, and/or 78. For example, in some embodiments, remote control application 140 is incorporated into a caregiver assistance application that operates on server 84 and that receives status updates from patient support apparatuses 20 and/or that assists the caregiver in performing one or more other tasks, such as performing rounding duties, managing a patient's bed sore risk, managing a patient's fall risk, and/or other activities. One example of such a caregiver assistance application into which the functions of remote control application 140 may be incorporated is the caregiver assistance application 124 disclosed in commonly assigned U.S. patent application Ser. No. 62/868,947 filed Jun. 30, 2019, by inventors Thomas Durlach et al. and entitled CAREGIVER ASSISTANCE SYSTEM, the complete disclosure of which is incorporated herein by reference.

Another type of software application that remote control application 140 may be incorporated into is a diagnostic and/or service application that is wholly or partially executed by server 84 and that is used to manage the servicing of, and/or perform diagnostic checks on, patient support apparatuses 20. One example of such a diagnostic and/or service application that remote control application 140 may be incorporated into is the equipment management service (e.g. local management server 34) disclosed in commonly assigned PCT patent application serial number PCT/US2017/041681 filed Jul. 12, 2017, by inventors David Becker et al. and entitled EQUIPMENT MANAGEMENT SYSTEM, the complete disclosure of which is incorporated herein by reference.

In alternative embodiments, it will be understood that, instead of, or in addition to, remote control application 140 executed on server 84, one or more of electronic devices 94 may be configured to include their own software application that communicates commands to patient support apparatus 20 for controlling room devices 72, 74, and/or 78. In such embodiments, electronic device 94 may communicate directly with patient support apparatuses 20 (e.g. bypass server 84), and/or they may communicate first with server 84 which then forwards their commands to patient support apparatuses 20.

In some embodiments, remote control application 140 is configured to allow a user to set up one or more schedules for one or more rooms 60 in order to control one or more of room devices 72, 74, and/or 78 according to one or more time-based and/or event-based schedules. Such schedules include, for example, the turning off of one or more room lights 74 at a certain time of day, the muting and activation of the closed captioning feature of television 72 at a certain time of day, the turning on of room light 74 at a certain time of day, the changing of a television channel to a specific channel in response to a specific event (e.g. a patient being newly assigned to a patient support apparatus 20), the turning off of room light 74, reading light 78, and/or television 72 when a patient has exited from patient support apparatus 20 for more than a predetermined time, and the turning on of room light 74, reading light 78, and/or television 72 when the patient returns to patient support apparatus 20 (and/or when the current time is within a user-designated window, such as evening hours). Still other examples are possible.

For those schedules that are based on time, patient support apparatus 20 may be configured to include an onboard clock that is used to determine when to implement the schedule. In some such embodiments, patient support apparatus 20 may utilize any of the clock functions disclosed in commonly assigned U.S. patent application Ser. No. 15/642,621 filed Jul. 6, 2017, by inventors Anuj Sidhu et al. and entitled PATIENT SUPPORT APPARATUSES WITH CLOCKS, the complete disclosures of which are incorporated herein by reference.

In those examples where the schedule is based partially or wholly on an event, the event may be determined, either wholly or partially, by one or more sensors onboard patient support apparatus 20 (e.g. an exit detection system and/or scale system), and/or by input from one or more other servers 92 on local area network 80 (e.g. an electronic health records server that informs patient support apparatus server 84 when a patient has had a medical treatment or therapy performed, an Admission, Discharge and Tracking (ADT) server that informs server 84 when a new patient has been assigned to a patient support apparatus 20, etc.). Still other devices that are in communication with patient support apparatus 20 (e.g. electronic device 94, patient support apparatus server 84, etc.) may also automatically trigger one or more changes to room devices 72, 74, and/or 78 based on one or more schedules that are input into patient support apparatus server 84.

In some embodiments, any schedule that a user sets up for one or more patient support apparatuses 20 is stored in patient support apparatus server 84 and patient support apparatus server 84 automatically sends corresponding commands to the patient support apparatuses 20 to change room devices 72, 74, and/or 78 at the appropriate time(s) (if the schedule is partially or wholly time-based), or in response to one or more detected events (if the schedule is partially or wholly event-based). In such embodiments, patient support apparatuses 20 need not include any data stored onboard regarding the schedule. In another embodiment, the schedule is forwarded to patient support apparatuses 20 and main controller 110 (or another controller, such as headwall communications controller 112) automatically makes the requisite changes to pins 130 in accordance with the schedule. In these latter embodiments, patient support apparatus server 84 need not retain any data concerning the schedule in its own memory after sending it to the appropriate patient support apparatuses 20. In still other embodiments, one or more schedules may be partially carried out by a controller onboard patient support apparatus 20 and partially carried out by patient support apparatus server 84.

In alternative embodiments of patient support apparatus 20, patient support apparatus 20 may be configured to wirelessly communicate with headwall communications outlet 64, instead of using a nurse call cable 66. One example of such a modified patient support apparatus 20a is shown and described below with respect to FIGS. 7, 8A and 8B. Unless otherwise stated herein, patient support apparatus 20a includes all of the same features and/or functionality as patient support apparatus 20, and may be modified in any of the same manners discussed herein with respect to patient support apparatus 20.

Figure 6:
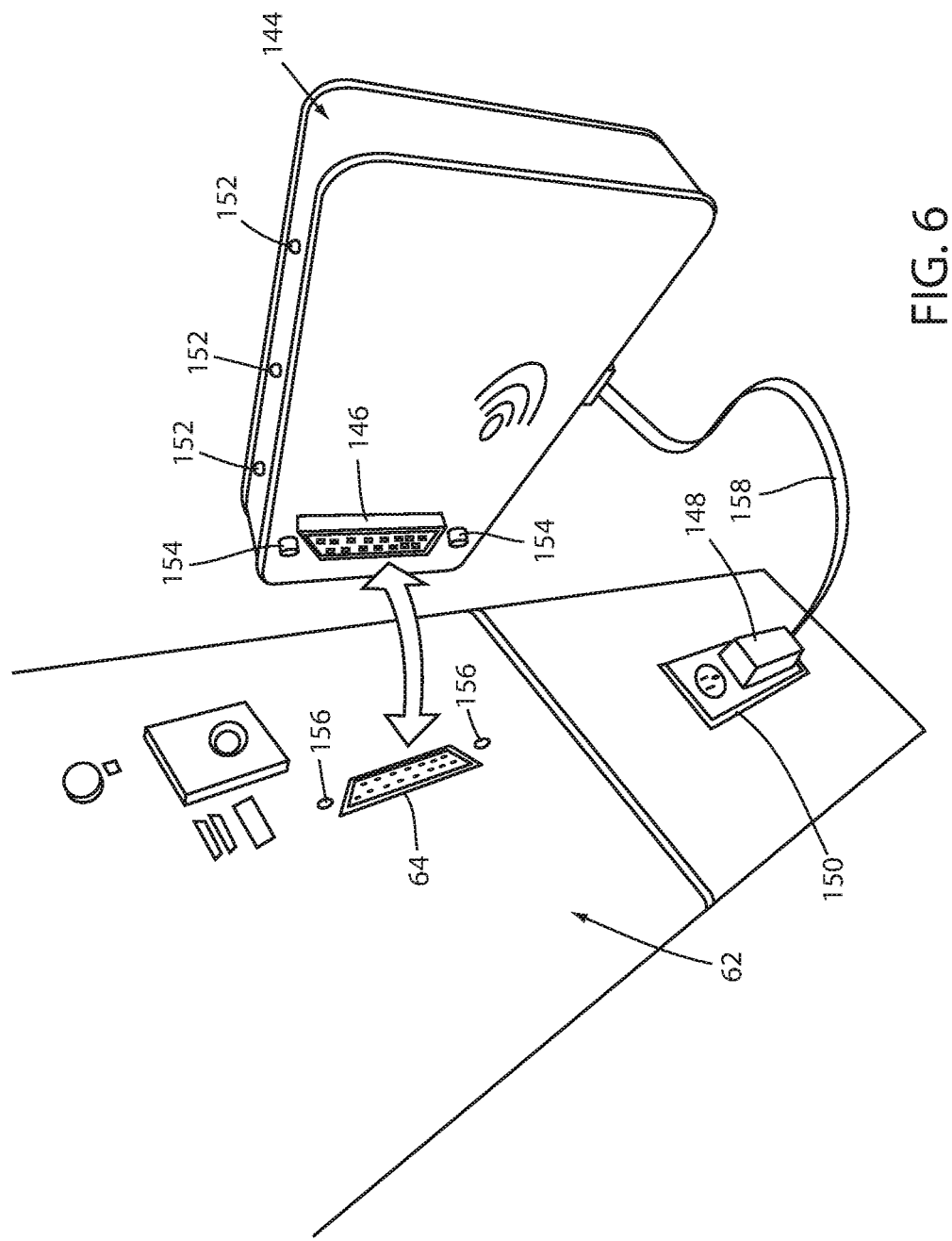
FIG. 6 is a perspective view of a first embodiment of a headwall unit adapted to physically couple to an outlet in a headwall of a healthcare facility
Figure 7:
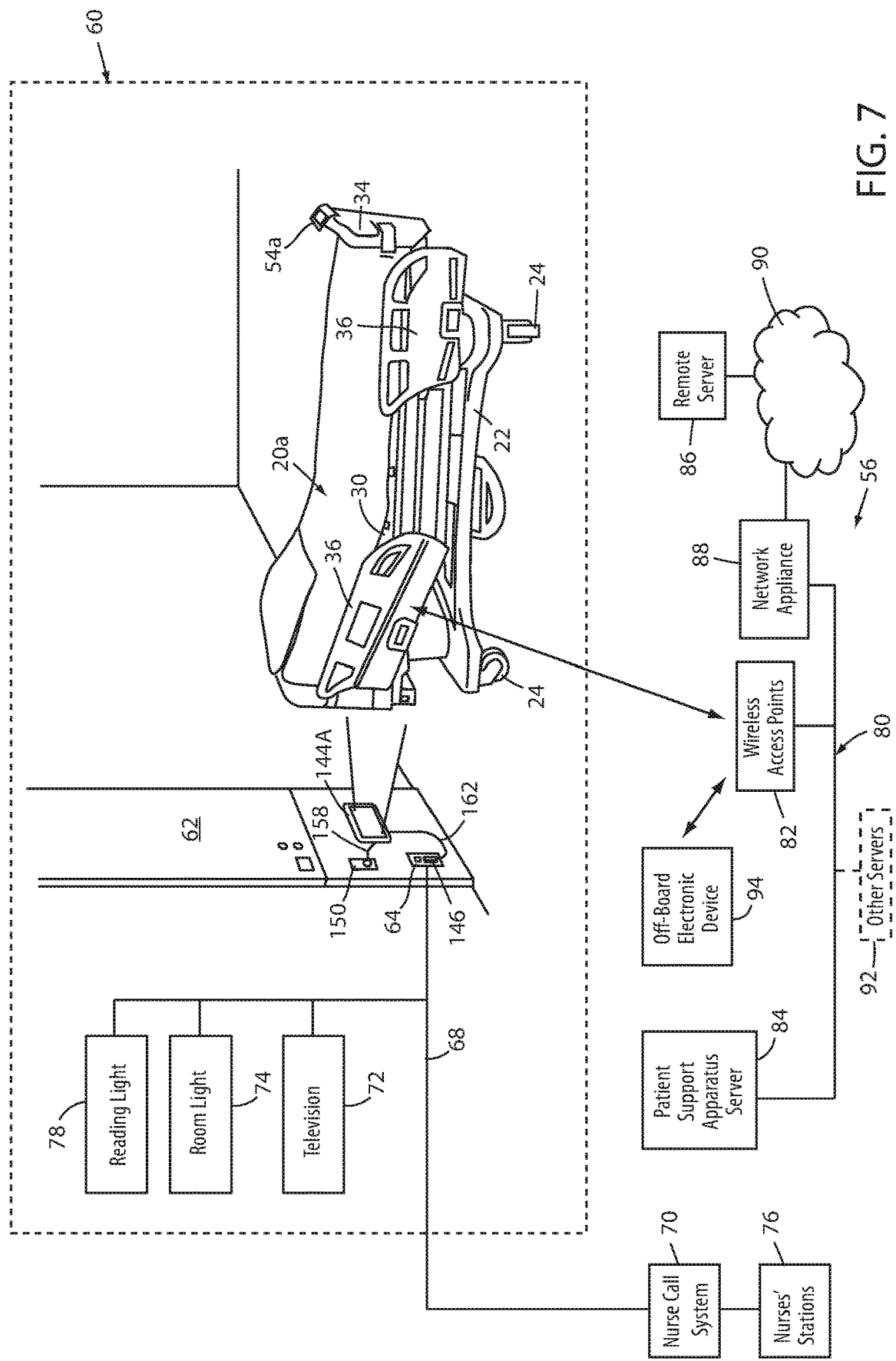
FIG. 7 is a diagram of an alternative patient support apparatus shown coupled to the IT infrastructure of a healthcare facility in a second manner.

In order for patient support apparatus 20a to wirelessly communicate with headwall communications outlet 64, it utilizes a headwall unit, such as a headwall unit 144 (FIG. 6) or a headwall unit 144a (FIGS. 7-8B). Headwall units 144, 144a are adapted to wirelessly receive signals from patient support apparatus 20a and deliver the signals to communications outlet 64 in a manner that matches the way the signals would otherwise be delivered to communications outlet 64 if a conventional nurse call cable 66 were connected between patient support apparatus 20a and communications outlet 64. In other words, patient support apparatus 20a and headwall unit 144, 144a cooperate to provide signals to communications outlet 64 in a manner that is transparent to communications outlet 64 such that outlet 64 cannot detect whether it is in communication with patient support apparatus 20 via a wired connection or it is in communication with patient support apparatus 20a via a wireless communication. In this manner, a healthcare facility can utilize the wireless communication abilities of one or more patient support apparatuses 20a without having to make any changes to their existing communication outlets 64.

In addition to sending signals received from patient support apparatus 20a to communications outlet 64, headwall units 144, 144a (FIGS. 6-8B) are also adapted to forward signals received from communications outlet 64 to patient support apparatus 20a. Headwall units 144, 144a are therefore adapted to provide bidirectional communication between patient support apparatus 20a and communications outlet 64. Such communication includes, but is not limited to, communicating command signals from any of controls 50 and/or from any of electronic device 94 to corresponding room devices 72, 74, and/or 78. Such communication also includes communicating audio signals between a person supported on patient support apparatus 20a and a caregiver positioned remotely from patient support apparatus 20a. The audio signals received by headwall units 144, 144a from a microphone on patient support apparatus 20a are forwarded to communications outlet 64, and the audio signals received from communications outlet 64 are forwarded to a speaker onboard patient support apparatus 20a.

Figure 8A:
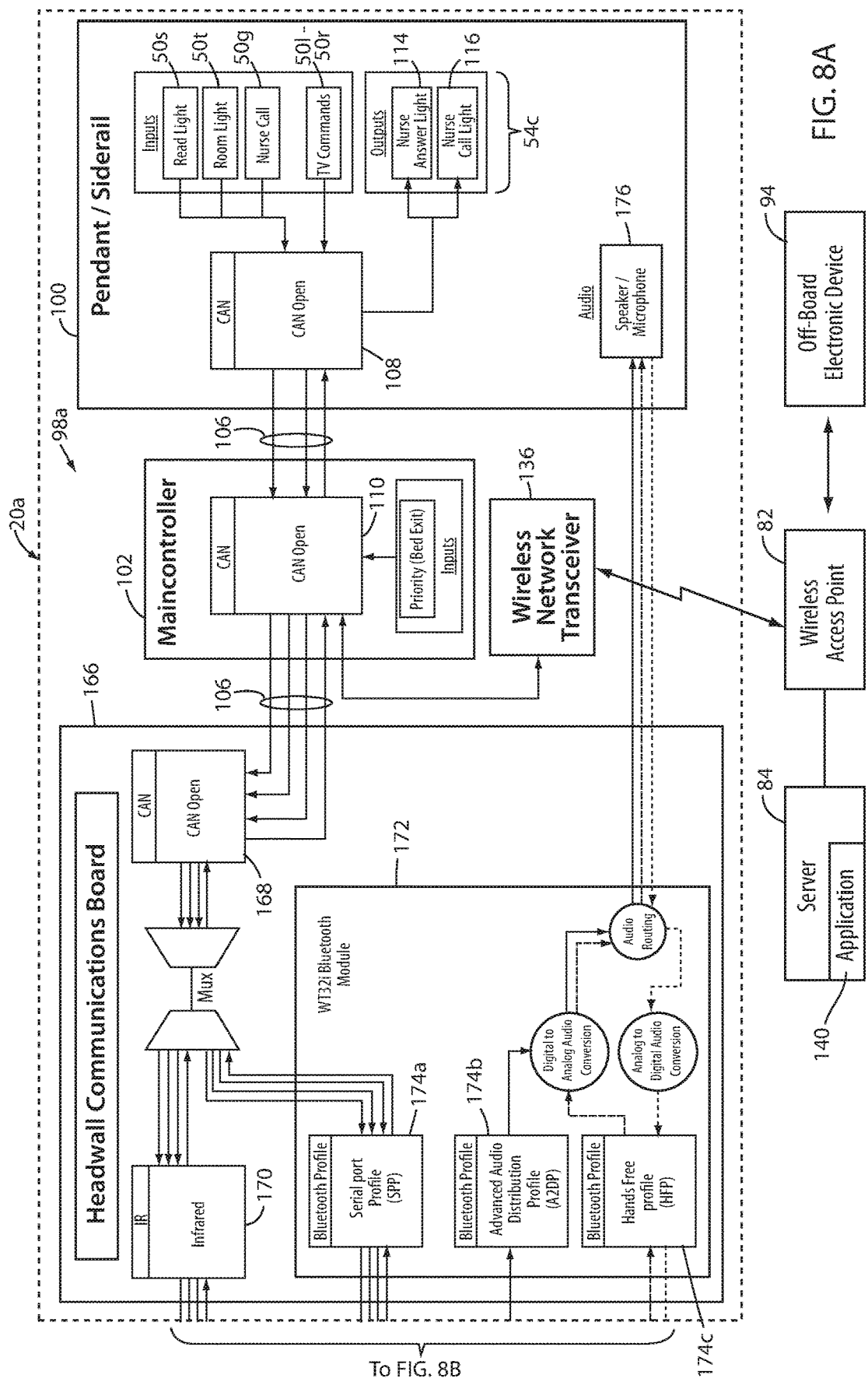
FIG. 8A is a first portion of a control system of the patient support apparatus of FIG. 7.

Headwall units 144, 144a communicate the data and signals it wirelessly receives from patient support apparatus 20a to communications outlet 64 by utilizing headwall interface 120 (FIG. 8A). Headwall interface 120 of headwall unit 144, 144a is adapted to electrically couple to communications outlet 64 and operate in the same manner as headwall interface 120 of patient support apparatus 20. That is, headwall interface 120 of headwall unit 144, 144a is adapted to change the voltages and/or states of a plurality of pins 130 that are electrically coupled to corresponding pins inside of communications outlet 64 when headwall units 144, 144a are physically coupled to communications outlet 64.

Headwall unit 144 (FIG. 5) includes a connector 146 that is adapted to be physically inserted into headwall communications outlet 64. Connector 146 is a 37 pin connector that includes 37 pins adapted to be inserted into 37 mating sockets of communications outlet 64. As was described above with respect to nurse call cable 66, such 37 pin connections are one of the most common types of connectors found on existing headwalls of medical facilities for making connections to the nurse call system 70 and room devices 72, 74, and 78. Connector 146 is therefore configured to mate with one of the most common type of communication outlets 64 used in medical facilities. Such 37 pin connectors, however, are not the only type of connectors, and it will be understood that headwall unit 144 can utilize different types of connectors 146 that are adapted to electrically couple to different types of communication outlets 64. One example of such an alternative communications outlet 64 and cable is disclosed in commonly assigned U.S. patent application Ser. No. 14/819,844 filed Aug. 6, 2015 by inventors Krishna Bhimavarapu et al. and entitled PATIENT SUPPORT APPARATUSES WITH WIRELESS HEADWALL COMMUNICATION, the complete disclosure of which is incorporated herein by reference. Still other types of communication outlets 64 and corresponding connectors 146 may be utilized.

Headwall unit 144 also includes an electrical plug 148 positioned at an end of an electrical cord 158. Plug 148 is adapted to be inserted into a conventional electrical outlet 150. Electrical plug 148 and cord 158 enable headwall unit 144 to receive power from the mains electrical supply via outlet 150. It will be appreciated that, in some embodiments, headwall unit 144 is battery operated and plug 148 may be omitted. In still other embodiments, headwall unit 144 may be both battery operated and include plug 148 so that in the event of a power failure, battery power supplies power to headwall unit 144, and/or in the event of a battery failure, electrical power is received through outlet 150.

The embodiment of headwall unit 144 shown in FIG. 6 also includes a plurality of status lights 152. Status lights 152 provide visual indications about one or more aspects of headwall unit 144. For example, in some embodiments, the illumination of one of status lights 152 indicates that headwall unit 144 is in successful communication with nurse call system 70 and/or patient support apparatus 20a. The illumination of one or more additional status lights 152 may also or alternatively indicate that power is being supplied to headwall unit 144 and/or the status of a battery included within headwall unit 144.

Headwall unit 144 also includes a set of connection plugs 154 that are sized, shaped, and positioned to be able to be inserted into corresponding receptacles 156 adjacent communication outlet 64. When plugs 154 are inserted into receptacles 156, the pins of connector 146 will be aligned with the pins of communications outlet 64. Further, plugs 154 and receptacles 156 are configured to help ensure that connector 146 remains frictionally retained within communications outlet 64 after connector 146 is inserted into outlet 64. Plugs 154 and receptacles 156, in some embodiments, may be replaced with mounting screws and screw holes, respectively, in some embodiments.

Headwall unit 144a of FIG. 7 differs from headwall unit 144 of FIG. 6 in that headwall unit 144a includes a connector cable 162 that extends between the body of headwall unit 144 and connector 146. In other words, instead of connector 146 being mounted directly to the body of the headwall unit, as connector 146 is with headwall unit 144, connector 146 of headwall unit 144*a* is mounted at the end of connector cable 162. Connector cable 162 therefore allows headwall unit 144*a* to be mounted to headwall 62 at a location that is offset from communications outlet 64.

Headwall units 144 and 144*a*, as noted, control the wireless communication between patient support apparatus 20*a* and communications outlet 64. In addition to communicating the signals used to control room devices 72, 74, and/or 78, headwall unit 144, 144*a* may also communicate the following information between patient support apparatus 20*a* and communications outlet 64: messages indicating the current status of one or more siderails 36 of patient support apparatus 20*a* (e.g. whether the side rails are up or down, or have changed position); messages indicating the current status of a brake on patient support apparatus 20*a*; messages indicating the current status of the height of support deck 30 relative to base 22 (e.g. such as whether support deck 30 is at its lowest height or not); messages indicating the current angle of head section 44; messages indicating the current status of an exit detection system (e.g. whether the exit detection system is armed or not); messages indicating the current charging status of one or more batteries on patient support apparatus 20*a*; messages indicating the current status of an alternating current (NC) power cable on patient support apparatus 20*a* (e.g. whether it is plugged in or not); diagnostic information about patient support apparatus 20*a*; messages containing patient data gathered from one or more sensors on board patient support apparatus 20*a*; message containing patient data gathered from one or more medical devices that are separate from patient support apparatus 20*a* but which communicate such data to patient support apparatus 20*a*; and/or any other messages containing information about patient support apparatus 20, the patient supported thereon, and/or a caregiver associated with the patient.

In addition to communicating the aforementioned data between patient support apparatus 20*a* and communications outlet 64, headwall units 144, 144*a* may also communicate location data to patient support apparatus 20*a* that enables patient support apparatus 20*a* and/or patient support apparatus server 84 to determine the location of patient support apparatus 20*a* within healthcare facility 56. Such location determination may be carried out in any of the manner disclosed in commonly assigned U.S. Pat. No. 9,999,375 issued Jun. 19, 2018, to inventors Michael Hayes et al. and entitled LOCATION DETECTION SYSTEMS AND METHODS, the complete disclosure of which is incorporated herein by reference.

Headwall units 144, 144*a* may also perform additional functions. In some embodiments, headwall units 144, 144*a* may perform any of the functions performed by the headwall units 76 disclosed in commonly assigned U.S. patent application Ser. No. 16/215,911 filed Dec. 11, 2018, by inventors Alexander Bodurka et al. and entitled HOSPITAL HEADWALL COMMUNICATION SYSTEM, the complete disclosure of which is incorporated herein by reference. In some embodiments, headwall units 144, 144*a* may also, or alternatively, perform any of the same functions performed by the headwall interfaces 72 disclosed in commonly assigned U.S. patent application Ser. No. 16/193,150 filed Nov. 16, 2018, by inventors Alexander Bodurka et al. and entitled PATIENT SUPPORT APPARATUSES WITH LOCATION/MOVEMENT DETECTION, the complete disclosure of which is also incorporated herein by reference. In still other embodiments, headwall units 144, 144*a* may also, or alternatively, perform any of the same functions performed by the headwall units 66 disclosed in commonly assigned U.S. patent application Ser. No. 16/217,203 filed Dec. 12, 2018, by inventor Alexander Bodurka et al. and entitled SMART HOSPITAL HEADWALL SYSTEM, the complete disclosure of which is incorporated herein by reference.

Patient support apparatus 20*a* is shown in FIG. 7 communicatively coupled to communications outlet 64 by way of headwall unit 144*a*. Patient support apparatus 20*a* is also shown communicatively coupled to a wireless access point 82 of local area network 80. Patient support apparatus 20*a* operates in the same way as that described above with respect to patient support apparatus 20 with the sole exception of communicating wirelessly with communications outlet 64, instead of communicating with outlet 64 via nurse call cable 66. Thus, patient support apparatus 20*a* is able to send commands to room devices 72, 74, and/or 78 by sending a wireless signal to headwall unit 144*a*, which in turn relays those commands to the appropriate room device 72, 74, and/or 78 via its electrical connection to outlet 64. Further, patient support apparatus 20*a* is able to receive commands for controlling room devices 72, 74, and/or 78 from an off-board electronic device 94 (either directly or via patient support apparatus server 84), and to forward those commands to the corresponding room device 72, 74, and/or 78 using headwall unit 144*a*.

FIGS. 8A and 8B illustrate a control system 98*a* included within patient support apparatus 20*a*. Those components of control system 98*a* that are the same as, and operate in the same manner as, the components of control system 98 (FIG. 5) of patient support apparatus 20 are labeled herein with the same reference numbers as control system 98. Those components of control system 98*a* that are different from control system 98 have been provided with a new reference number.

Control system 98*a* (FIG. 8A) differs structurally from control system 98 in two primary ways: control system 98*a* does not include headwall interface 120, and control system 98*a* includes a headwall communications board 166 that is adapted to wirelessly communicate with headwall unit 144, 144*a*. Pendant/siderail node 100, main node 102, and wireless network transceiver 136 operate in the same manner as they do in control system 98, and their will not be repeated herein.

Headwall communications board 166 (FIG. 8A) includes a headwall board controller 168 that may take on any of the same physical forms as any of controllers 108, 110, and/or 112, which were previously described. Headwall communications board 166 also includes an infrared transceiver 170 and a Bluetooth transceiver 172. Transceivers 170 and 172 are adapted to wirelessly communicate with headwall unit 144, 144*a*, and headwall communications board 166 controls the operation of transceivers 170 and 172. In some embodiments, the signals that are sent from patient support apparatus 20 to headwall unit 144, 144*a* are sent over both transceiver 170 and 172 in order to provide redundancy to these communications. In other embodiments, these signals are sent over only one of the transceivers 170, 172, while in still other embodiments, some data is sent via both transceivers 170, 172, while other data is only sent via one of these two transceivers 170, 172.

Headwall board controller 168 is adapted to forward commands received from any of controls 50 (whether incorporated into the physical control panel 54*c* or a virtual control panel displayed on the screen of electronic device 94) to headwall unit 144, 144*a*. Thus, for example, if a user of electronic device 94 sends a command to shut off television 72 to patient support apparatus 20 via wireless access point 82, network transceiver 136 receives this command and forwards it to headwall board controller 168 (either directly, or via main node 102). Headwall board controller 168, in turn, sends a signal to headwall unit 144, 144a indicating that the television 72 is to be turned off. As noted, the signal may be sent via transceiver 170 or transceiver 172, or via both. As will be discussed in greater detail below, headwall unit 144, 144a receives this signal and then adjusts the electrical characteristic of pin 34 (e.g. applies a sequence of voltages) of its headwall interface 120 in such a way so as to cause television 72 to be turned off.

As shown in FIG. 8A, Bluetooth transceiver 172 of headwall communications board 166 may utilize a plurality of different Bluetooth profiles 174a-c when communicating with headwall unit 144, 144a. These include a serial port profile 174a, an advanced audio distribution profile 174b, and a hand free profile 174c. In the illustrated embodiment, Bluetooth transceiver 172 uses the serial port profile for communicating the commands to room devices 72, 74, and 78. Bluetooth transceiver 172 uses the other profiles 174b and 174c for transmitting the voice signals between patient support apparatus 20 and communications outlet 64 that arise when the patient onboard patient support apparatus 20a is talking to a remotely positioned nurse via nurse call system 70. The patient's voice signals are detected onboard patient support apparatus 20a via a microphone 176 and sent to headwall unit 144, 144a using transceiver 172. The nurse's voice signals are received from headwall unit 144, 144a and forwarded to a speaker 176 onboard patient support apparatus 20a. In some embodiments, the speaker and microphone are the same device, such as shown by microphone/speaker 176 in FIG. 8A, while in other embodiments, the speaker and microphone may be separate devices. Further, in some embodiments, the management of Bluetooth transceiver 172 in communicating audio signals between headwall unit 144, 144a and the speaker, microphone, and/or speaker/microphone is carried out in any of the manners disclosed in commonly assigned U.S. patent application Ser. No. 16/847,753 filed Apr. 14, 2020, by inventors Alexander Bodurka et al. and entitled PATIENT SUPPORT APPARATUSES WITH NURSE CALL AUDIO MANAGEMENT, the complete disclosure of which is incorporated herein by reference.

Headwall unit 144, 144a (FIG. 8B) includes an infrared transceiver 180, a Bluetooth transceiver 182, a headwall unit controller 184, configuration circuitry 132, and, in at least some embodiments, smart television control circuitry 134. Infrared transceiver 180 is adapted to communicate with infrared transceiver 170 of patient support apparatus 20a using infrared waves. Bluetooth transceiver 182 if adapted to communicate with Bluetooth transceiver 172 of patient support apparatus 20a using RF waves in accordance with the conventional Bluetooth standard (e.g. IEEE 802.14.1 and/or the standard maintained by the Bluetooth Special Interest Group (SIG) of Kirkland, Washington, USA. Headwall unit controller 184 is adapted to control the operation of transceivers 180, 182, and configuration circuitry 132, and headwall unit controller 184 may be implemented as one or more microcontrollers, and/or in any of the same manners as controllers 108, 110, and/or 112, as discussed previously. Configuration circuitry 132 may be the same as the configuration circuitry 132 of patient support apparatus 20, and headwall interface 120 may be the same as headwall interface 120 of patient support apparatus 20.

When headwall unit 144, 144a receives a command to change a feature of one of the room devices 72, 74, and/or 78 from one, or both, of transceivers 180, 182, headwall unit controller 184 interprets the command so as to control configuration circuitry 132 in a manner that leads to the correct electrical change on the correct pins 130 of headwall interface 120. For example, if headwall unit 144, 144a receives a command from patient support apparatus 20 for turning off reading light 78, headwall unit controller 184 controls configuration circuitry 132 such that the electrical state of pin 2 (a.k.a. pin 130a) is changed. As noted previously, this change in state may vary, depending upon the model and/or implementation of the reading light 78. In some embodiments, headwall interface 120 may open the connection between pin 2 and pin 27 to turn off reading light 78; in other embodiments, it may close this connection; while in still other embodiments, it may change the voltage on pin 2 and/or perform some other electrical change.

Similarly, headwall unit controller 184 and configuration circuitry 132 are configured to change the electrical characteristic of pin 3 (a.k.a. pin 130b) when a command is received from patient support apparatus 20a to change a status of room light 74. Headwall unit controller 184 and configuration circuitry 132 are also configured to change the electrical characteristic of pin 25 (a.k.a. pin 130c) when a patient onboard patient support apparatus 20a places a call to a remotely positioned nurse (e.g. presses no nurse call control 50g). Still further, headwall unit controller 184 and configuration circuitry 132 are also configured to perform the following: (a) change the electrical characteristic of pin 30 (a.k.a. pin 130d) when an exit detection system onboard patient support apparatus 20a detects a patient exit; (b) change the electrical characteristic of pin 34 (a.k.a. pin 130) when a command is received from patient support apparatus 20a to change a feature of television 72; (c) change the electrical characteristic of pin 9 (a.k.a. pin 130f) when the patient is speaking and patient support apparatus 20a is attempting to send audio signals to the remote nurse via headwall unit 144, 144a; (d) read the current electrical state of pin 16 (a.k.a. pin 130g) to determine when a remotely positioned nurse has answered a patient call and to then send a command to patient support apparatus 20a to illuminate nurse answer light 114; (e) read the current electrical state of pin 19 (a.k.a. pin 130h) to determine when a remotely positioned nurse has placed a call to the patient and to send a command to patient support apparatus 20a and to illuminate nurse call light 116; and (f) transfer audio signals between patient support apparatus 20a and nurse call system 70 using pins 4 and 5 (a.k.a. pins 130i and 130j).

Although patient support apparatus 20 has been described herein as communicating with communication outlet 64 via cable 66 and patient support apparatus 20a has been described herein as communicating with outlet 64 via wireless communication through headwall unit 144, 144a, it will be understood by those skilled in the art that either or both of patient support apparatuses 20 or 20a can be modified to include the circuitry of both control systems 98 and 98a such that they are able to communicate with outlet 64 both via wire and wirelessly. Such embodiments allow patient support apparatuses to communicate with outlet 64 in rooms where no headwall unit 144, 144a is present, as well as to communicate with outlet 64 in rooms where no cable 66 is present and/or it is otherwise desired to communicate without a cable 66.

In addition to being able to control room devices 72, 74, and/or 78 in response to the activation of controls 50 and/or in response to commands received from electronic devices 94, patient support apparatus 20a, in some embodiments, is also configured to modify configuration circuitry 132 in response to inputs from one or more of control panels 54, as well as from electronic devices 94. In such embodiments, a user can change the configuration circuitry to make the communications to and from patient support apparatus 20a compatible with the particular nurse call system 70 and/or room devices 72, 74, and/or 78 that are present in a particular room. These configuration changes are discussed in more detail below with respect to FIGS. 9-15.

FIGS. 9-15 depict screens that are displayable on any of the displays of patient support apparatuses 20, of patient support apparatuses 20a, and/or of electronic devices 94. These screens allow a user positioned at patient support apparatus 20, 20a, or a user positioned at electronic device 94, to change the configuration circuitry 132 of either patient support apparatuses 20, 20a or headwall units 144, 144a so that the patient support apparatuses 20, 20a are able to properly communicate with the nurse call system 70 and the room devices 72, 74, and 78. The screens shown in FIGS. 9-15 are therefore displayed on display 52 of patient support apparatuses 20, 20a under the control of main controller 110 (or another controller responsible for overseeing the operation of display 52), or they are displayed on a screen of an electronic device 94 under the control of remote control application 140 (or otherwise interacting with remote control application 140).

Figure 9:
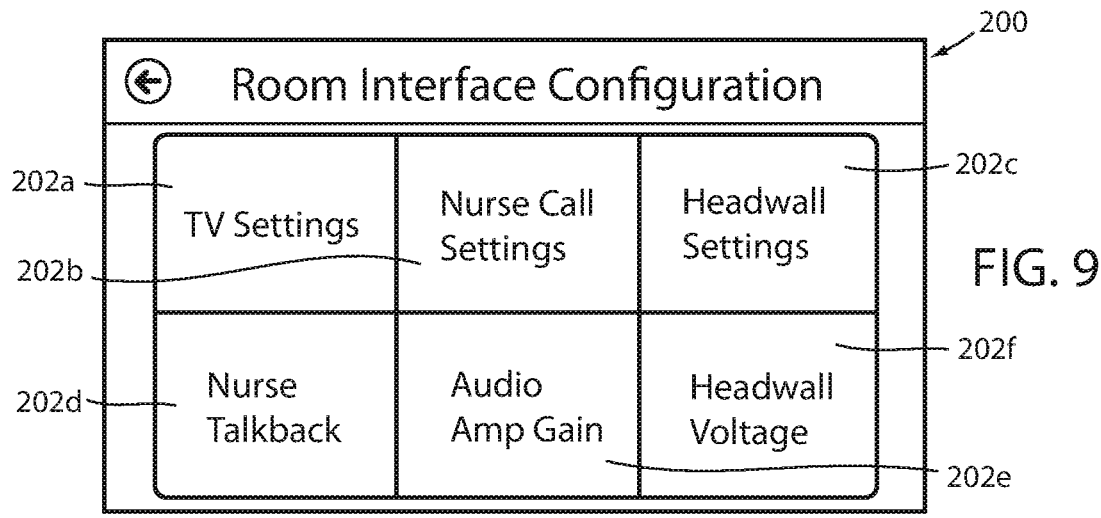
FIG. 9 is an illustrative master configuration control screen displayable on the display of any of the patient support apparatuses disclosed herein or a display of any of the off-board electronic devices disclosed herein.

FIG. 9 illustrates one example of a master configuration control screen 200 that, as noted, is displayable on display 52 of control panel 54a and/or on a display of any of electronic devices 94 that are executing, or in communication with, remote control application 140. Master configuration control screen 200 includes six configuration options 202a-f that, when selected, bring the user to the six screens shown in FIGS. 10-15, respectively. These six screens allow the user to change and control various configuration settings that are used by patient support apparatus 20, 20a when communicating with communications outlet 64, whether via cable 66 or wirelessly using headwall unit 144, 144a. These six screens will be discussed in more detail below with respect to display 52 of patient support apparatus 20, 20a, but it will be understood that this discussion applies equally to the displays of electronic devices 94 that are executing, or in communication with, remote control application 140.

Figure 10:
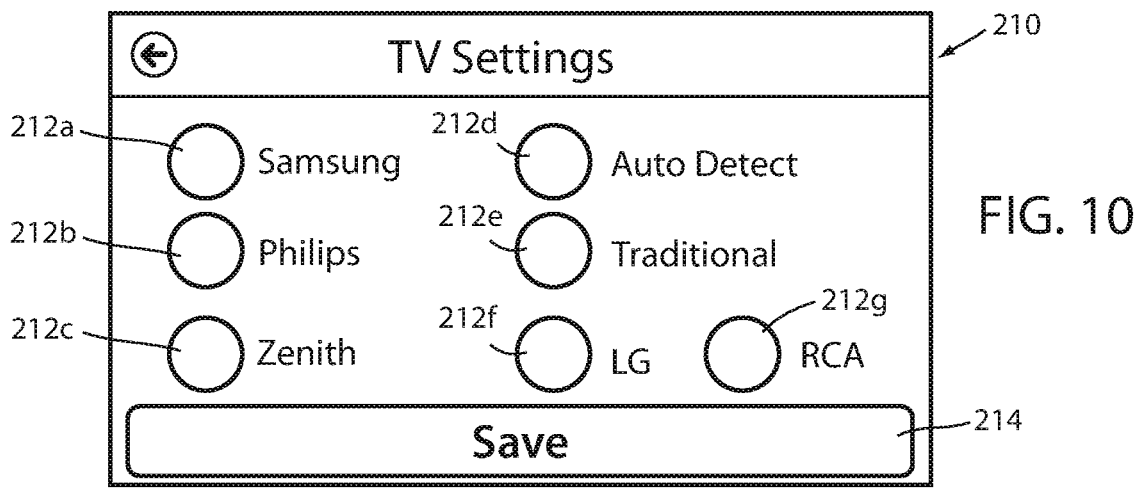
FIG. 10 is an illustrative TV settings control screen displayable on the display of any of the patient support apparatuses disclosed herein or a display of any of the off-board electronic devices disclosed herein.

If a user selects TV settings option 202a of master configuration control screen 200 (FIG. 9), display 52 of control panel 54a displays a TV settings control screen 210, such as shown in FIG. 10. TV settings control screen 210 includes a plurality of TV options 202a-g. Each option 202a-g corresponds to a different set of signals that are sent to television 72 when a user presses on controls 50l-50r of control panel 54c. Most options correspond to a particular brand of TV because most TV manufacturers program all of their models of televisions to respond to the same set of signals for implementing the same changes. In other words, for example, all Samsung televisions 72 will typically increase their channel in response to a first sequence of signals, decrease their channel in response to a second sequence of signals, increase their volume in response to a third sequence of signals, and perform the other functions controlled by controls 50l-50r in response to still other sequences of signals, and the set of sequences for controlling all of these functions is the same for all Samsung brand televisions. However, other manufacturers of televisions may program their televisions to change channels, for example, in response to a different sequence of signals than what the Samsung televisions use. Accordingly, TV settings control screen 210 allows a user to select which brand of television is present in the room 60 in which patient support apparatus 20, 20a is located, and this information is then communicated to smart TV control circuitry 134. As noted smart TV control circuitry 134 stores in its memory all of the signal sequences that are used by all, or substantially all, television manufacturers and selects which set of sequences to use to control television 72 based on the user's selection on screen 210.

In addition to listing a plurality of specific brands, TV settings control screen 210 (FIG. 10) also includes an auto-detect option 212d. If the user selects the auto-detection option 212d, headwall communication controller 112 (for patient support apparatuses 20) or headwall unit controller 184 (for patient support apparatuses 20a) measures the voltage across pins 33 and 34 (see FIG. 32) of communications outlet 64 (which is electrically coupled to headwall interface 120). Controller 112 and/or 184 attempts to determine the television brand based on the measured voltage and the fact that different television brands output different voltages on their remote control lines. Based on the detected voltage, controller 112 and/or 184 makes a conclusion about the brand of television and implements the corresponding configurations settings for that brand. If controller 112 and/or 184 are unable to determine the brand based on the measured voltage, a message may be shown on display 52 indicating that the television brand could not be determined.

In an alternative embodiment, headwall communication controller 112 is adapted to automatically detect a television brand (or model) by automatically sending a series of test commands to the television 72 and analyzing its response (as measured through changes in the audio signals received from the television 72). From this information, controller 112 is able to determine what set of controls to use with television 72. The series of test commands include, but are not necessarily limited to, commands that change the audio output of television 72, such as commands to increase the volume, decrease the volume, mute the television 72, turn off the television 72 (in which case audio signals will cease completely), and turn on the television. By sending these test commands and determining which test commands lead to the expected behavior of the television's audio response, and which ones don't, headwall communications controller 112 (or headwall unit controller 184) is typically able to determine the brand of television 72. When so determined, it informs smart television control circuit 134, which then uses the appropriate set of commands for controlling television 72. If controllers 112 and/or 184 are unable to determine the brand of television, a message may be shown on display 52 indicating that the television brand could not be determined. Other types of auto-detection algorithms may also or alternatively be used.

TV settings control screen 210 (FIG. 10) also includes a traditional option 212e. This option corresponds to older televisions that only respond to remote control signals by increasing the channel until the maximum channel is reached, then turning off, then turning on at the lowest channel, and then repeating this cycle. Such televisions are not able to follow commands to decrease their channel, turn on/off muting and/or closed captioning, or change their volume. In response to a user selecting traditional option 212e, headwall communications controller 112 (for patient support apparatuses 20) and headwall communications board 166 (for patient support apparatuses 20a) send the same signal to communications outlet 64 regardless of which television control 50l-50r the user activates because the television 72 is not able to be remotely controlled in any other manner than the aforementioned cycle, and this same signal prompts the television 72 through this cycle. In some embodiments, control panel 54c and/or another control panel displays a message to the patient when he or she attempts to control such a standard television 72. The message informs the patient that the standard television will only respond to the patient's activation of controls 50*l-r* by progressing through the aforementioned cycle, or otherwise informs the patient that controls 50*l*-50*r* are not defective, but instead are operating as intended for the standard television 72.

Figure 11:
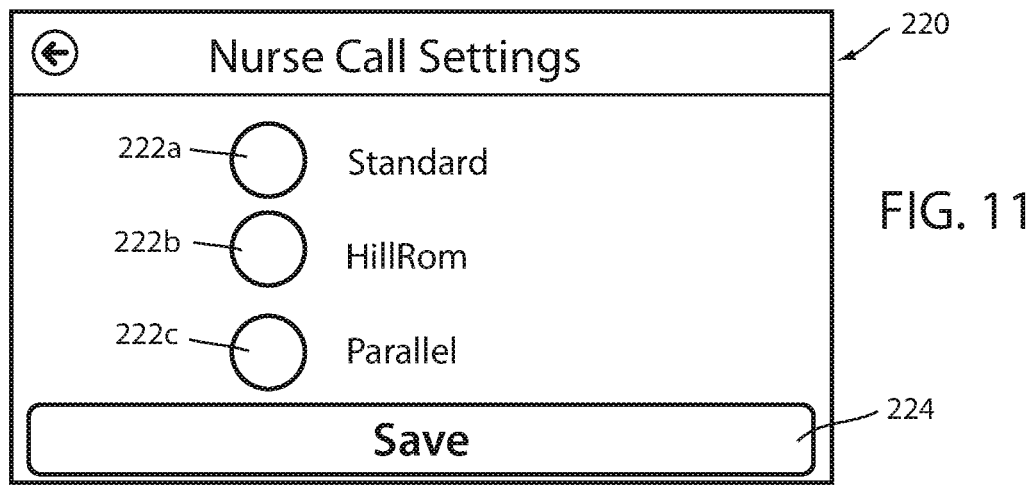
FIG. 11 is an illustrative nurse call settings screen displayable on the display of any of the patient support apparatuses disclosed herein or a display of any of the off-board electronic devices disclosed herein.

If a user selects nurse call settings option 202*b* of master configuration control screen 200 (FIG. 9), display 52 of control panel 54*a* displays a nurse call settings control screen 220, such as shown in FIG. 11. Nurse call settings control screen 220 includes a plurality of nurse call setting options 222*a-c*. Each of the options 222*a-c* corresponds to different manners in which nurse call systems communicate with patient support apparatus 20, 20*a*, and vice versa. More specifically, for a first type of nurse call system, a first set of pins are electrically shorted; for a second type of nurse call system, a second set of pins are electrically shorted; and for a third type of nurse call system, both the first and second sets of pins are electrically shorted. In the example shown in FIG. 11, these three types of nurse call systems are labeled as "standard," "Hill-Rom," and "parallel."

If the user selects the standard option 222*a* (FIG. 11), controller 112 (for patient support apparatuses 20) or controller 184 (for patient support apparatuses 20*a*) is adapted to change configuration circuitry 132 such that it will electrically short together pins 30 and 31 in response to an exit detection alert (as detected by an exit detection system onboard patient support apparatus 20, 20*a*) and it will electrically short together pins 25 and 26 in response to a nurse call placed by the patient on patient support apparatus 20, 20*a*.

If the user selects the Hill-Rom option 222*b* (FIG. 11), controller 112 (for patient support apparatuses 20) or controller 184 (for patient support apparatuses 20*a*) is adapted to change configuration circuitry 132 such that it will electrically short together pins 25 and 26, as well as pins 30 and 31, in response to an exit detection alert (as detected by the exit detection system onboard patient support apparatus 20, 20*a*). Additionally if the user selects the Hill-Rom option 222*b* (FIG. 11), controller 112 (for patient support apparatuses 20) or controller 184 (for patient support apparatuses 20*a*) is adapted to change configuration circuitry 132 such that it will electrically short together pins 25 and 26 in response to a nurse call placed by the patient on patient support apparatus 20, 20*a*.

If the user selects the parallel option 222*c* (FIG. 11), controller 112 (for patient support apparatuses 20) or controller 184 (for patient support apparatuses 20*a*) is adapted to change configuration circuitry 132 such that it will electrically short together pins 25 and 26, as well as pins 30 and 31, in response to an exit detection alert (as detected by the exit detection system onboard patient support apparatus 20, 20*a*). Additionally if the user selects the parallel option 222*c* (FIG. 11), controller 112 (for patient support apparatuses 20) or controller 184 (for patient support apparatuses 20*a*) is adapted to change configuration circuitry 132 such that it will perform the same electrical shorting in response to a nurse call placed by the patient on patient support apparatus 20, 20*a* (i.e. shorting together pin 25 with pin 26, and shorting together pin 30 with pin 31).

Figure 12:
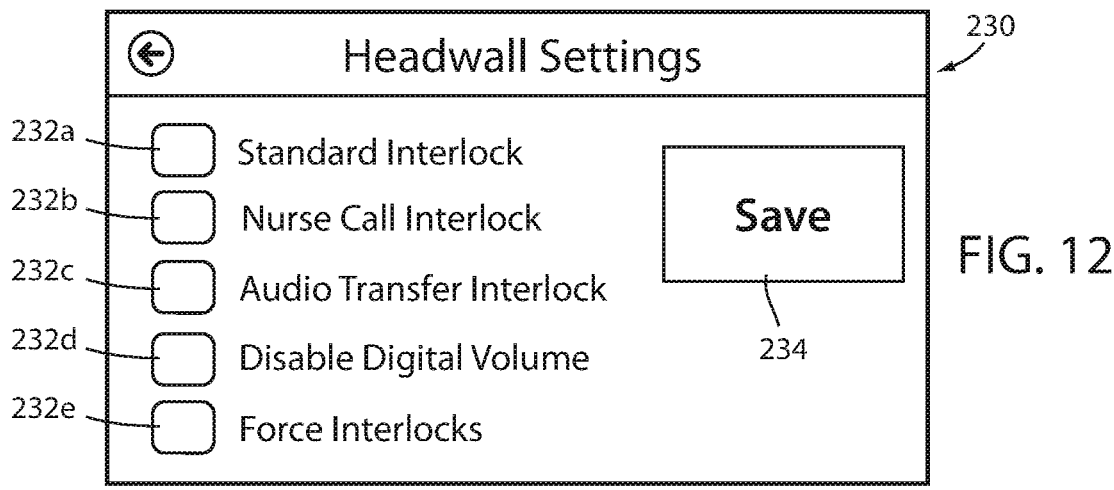
FIG. 12 is an illustrative headwall settings screen displayable on the display of any of the patient support apparatuses disclosed herein or a display of any of the off-board electronic devices disclosed herein.

If a user selects headwall settings option 202*c* of master configuration control screen 200 (FIG. 9), display 52 of control panel 54*a* displays a headwall settings control screen 230, such as shown in FIG. 12. Headwall settings control screen 230 includes a plurality of headwall setting options 232*a-e*. Generally speaking, four of these settings relate to how the nurse call system 70 determines that a patient support apparatus 20, 20*a* is currently connected or disconnected to communications outlet 64, and one of these settings relates to controlling the volume of television 72. More specifically, each of the options 232*a-c* and 232*e* corresponds to different manners in which patient support apparatus 20, 20*a* communicates to the nurse call system 70 that it is present and communicatively coupled to the nurse call system via communication outlet 64, and option 232*d* corresponds to how patient support apparatus 20, 20*a* changes the volume of the television audio signals that are output from speaker 176.

Options 232*a-c* and 232*e* specify different types of interlocks, which refers to which pins 130 are electrically shorted together by headwall interface 120 when headwall interface 120 is plugged into outlet 64. The coupling together of these pins is detected by the nurse call system 70, such as by sending a signal to one of the two pins that are coupled together and looking for the signal to return on the other one of the two pins 130 that are coupled together. If the return signal is detected, nurse call system 70 is able to confirm that patient support apparatus 20, 20*a* is communicatively coupled to itself. If the nurse call system 70 does not detect the return signal, it concludes patient support apparatus 20, 20*a* is not coupled to nurse call system 70 and issues what is known as a cord-out alert, which is an alert communicated to caregivers that the patient support apparatus 20, 20*a* in a particular room is no longer communicatively coupled to the nurse call system 70 (and the patient associated with that patient support apparatus is therefore unable to communicate with nurse call system 70). Because different nurse call systems 70 use different pairs of pins to detect the presence of a patient support apparatus, patient support apparatuses 20, 20*a* need to be properly configured to match the system used by a particular healthcare facility. Headwall settings control screen 230 allows the user to make this selection.

In at least one embodiment, controller 112 (for patient support apparatuses 20) or controller 184 (for patient support apparatuses 20*a*) is configured, by default, to not couple together any of the interlock pins until controller 112 (or 184) detects a voltage across an expected set of pins applied by the nurse call system 70, or the user manually selects a "force interlocks" option (discussed in more detail below). In this manner, the interlock configurations are not implemented until controller 112 (or 184) verifies that it is coupled to the communications outlet 64 and nurse call system 70. This default configuration setting helps to ensure that neither patient support apparatus 20 nor headwall unit 144, 144*a* electrically short together any interlock pins prior to coupling to the nurse call system 70 and ensuring that the correct interlock pins are coupled together. This helps avoid damage that may otherwise occur for some nurse call systems 70 if the wrong interlock pins are coupled together.

If the user selects standard interlock option 232*a* (FIG. 12), controller 112 (for patient support apparatuses 20) or controller 184 (for patient support apparatuses 20*a*) is adapted to change configuration circuitry 132 such that pins 10 and 11 (FIG. 32) are electrically coupled together. In other words, headwall interface 120 is configured to implement an electrical jumper between pins 10 and 11 such that any signals sent to interface 120 from the nurse call system 70 on pin 10 are returned on pin 11, and vice versa.

If the user selects nurse call interlock option 232*b* (FIG. 12), controller 112 (for patient support apparatuses 20) or controller 184 (for patient support apparatuses 20*a*) is adapted to change configuration circuitry 132 such that pins 7 and 25 are electrically coupled together.

If the user selects audio transfer interlock option 232c (FIG. 12), controller 112 (for patient support apparatuses 20) or controller 184 (for patient support apparatuses 20a) is adapted to change configuration circuitry 132 such that pins 8 and 9 are electrically coupled together.

If the user selects any of the transfer interlock options 232a-c, configuration circuitry 132 is configured to only implement the electrical shorting of the aforementioned pins together in response to detecting one or more voltages between selected pins of the communications outlet 64. Such pins include, but are not limited to, pins 25 and 26, as well as pins 30 and 31. If controller 112 or controller 184 does not detect a voltage between either or both of these sets of pins (as sensed by configuration circuitry 132 and/or other sensors in headwall interface 120), it is configured, in some embodiments, to not implement any of the headwall setting options 232a-c. This is done for safety purposes as some nurse call systems can be damaged by shorting the pins of options 232a-c together.

In some nurse call systems, the voltages that the nurse call system 70 applies between pins 25 and 26 and/or between pins 30 and 31 are not sent applied by the nurse call system 70 until a patient support apparatus 20, 20a is coupled to communications outlet 64. In such systems, there is the possibility of a stalemate situation where patient support apparatus 20, 20a might not be shorting together any of the pins of options 232a-c because it is waiting for a voltage to be applied between pins 25 and 26 and/or between pins 30 and 31, yet the nurse call system is not applying any voltage between pins 25 and 26 or between pins 30 and 31 because it is waiting for patient support apparatus 20, 20a to implement its configuration settings. In such a situation, it is possible that patient support apparatus 20, 20a does not implement configuration option 232a-c and that nurse call system 70 does not detect the presence of patient support apparatus 20, 20a. In order to avoid such a situation, patient support apparatus 20a includes option 232e.

If the user selects the force interlocks option 232e (FIG. 12), controller 112 (for patient support apparatuses 20) or controller 184 (for patient support apparatuses 20a) is adapted to change configuration circuitry 132 without waiting to detect any voltage between pins of communication outlet 64. Instead, when option 232e is selected (along with one of options 232a-c), controller 112, 184 automatically electrically shorts together the pins identified in options 232a, 232b, or 232c without waiting to detect any voltage from the nurse call system 70. This avoids the stalemate situation mentioned above where patient support apparatus 20, 20a may be waiting to detect voltage from the nurse call system 70 before it applies its configuration settings while the nurse call system 70 may be waiting for the patient support apparatus 20, 20a to apply it configuration settings before it applies a voltage to communication outlet 64.

Figure 13:
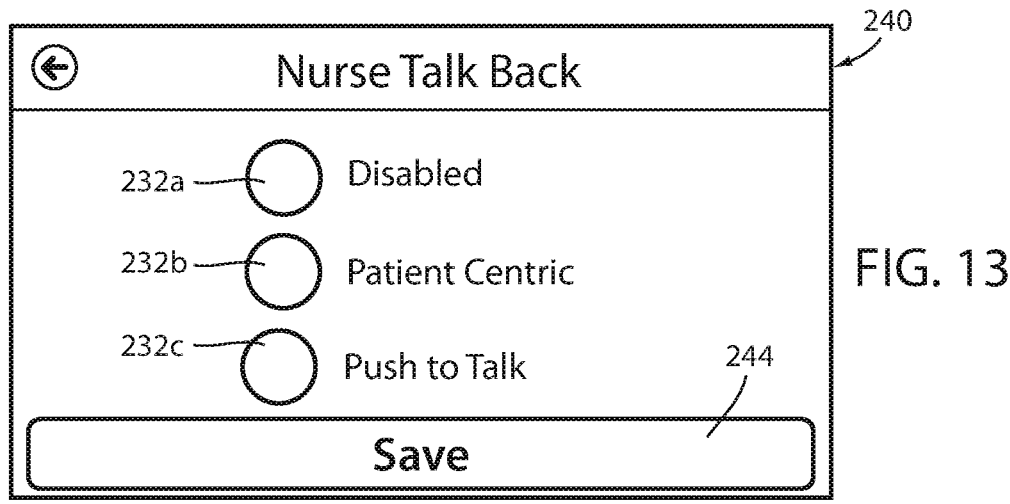
FIG. 13 is an illustrative nurse talk back screen displayable on the display of any of the patient support apparatuses disclosed herein or a display of any of the off-board electronic devices disclosed herein.

If the user selects the "disable digital volume" option 232d (FIG. 12), controller 112 (for patient support apparatuses 20) or controller 184 (for patient support apparatuses 20a) is adapted to not send a signal to television 72 to change its volume in response to a user activating control 50l or 50m (FIG. 3). Instead, patient support apparatus 20, 20a changes the amplification of its own onboard amplifier in response to the user activating control 50l or 50m. If the user does not select the "disable digital volume" option 232d, patient support apparatus 20, 20a sends a command to television 72 requesting it to increase or decrease its volume in response to a user activing controls 50l and/or 50m If a user selects nurse talk back option 202d of master configuration control screen 200 (FIG. 9), display 52 of control panel 54a displays a nurse talk back control screen 240, such as shown in FIG. 13. Nurse talk back control screen 240 includes a plurality of setting options 242a-c that are useful for managing the audio communications between the remote nurse and the patient. For many nurse call systems, the audio communication between the patient and the nurse takes place over a half-duplex communication channel. In such systems, only one person is able to speak at a time. For still other nurse call systems, no audio communications are able to take place, but the patient is able to send an electronic request to the nurse call system requesting that a nurse come and visit.

For those systems that utilize half-duplex communications, the audio signals from the patient's or the nurse's voice are sent over a single channel (e.g. pins 8 and pin 9), and the nurse call system typically determines whether the channel is being used to transmit audio signals from the nurse to the patient, or when the single channel is being used to transmit audio signals from the patient to the nurse.

If the user selects the "disabled" option 242a (FIG. 13), controller 112 (for patient support apparatuses 20) or controller 184 (for patient support apparatuses 20a) is adapted to not send any audio signals of the patient's voice to the nurse call system 70. Instead, headwall interface 120 sends a request for a nurse in response to the patient pressing control 50g. Any audio signals of the patient that are detected by microphone 176 are not forwarded by headwall interface 120 to communications outlet 64.

If the user selects the patient centric option 242b, controller 112 (for patient support apparatuses 20) or controller 184 (for patient support apparatuses 20a) is adapted to apply audio signals to the half-duplex communication channel (e.g. pins 8 and 9) whenever patient support apparatus 20, 20a detects that the patient is speaking into microphone 176. If the user selects the push to talk option 242c, controller 112 (for patient support apparatuses 20) or controller 184 (for patient support apparatuses 20a) is adapted to apply audio signals to the half-duplex communication channel only when the patient physically activates a control (not shown) on patient support apparatus 20, 20a necessary for him/her to communicate with the remote nurse. The control may be a button, switch, dial, or the like, that, when pressed, causes the patient's audio signals to be electrically applied to the half-duplex communication channel. The manner in which control system 98, 98a does or does not transfer audio signals of the patient's voice from microphone 176 to the communication channel is therefore dictated by the nurse talk back settings 242a-c of FIG. 13.

Figure 14:
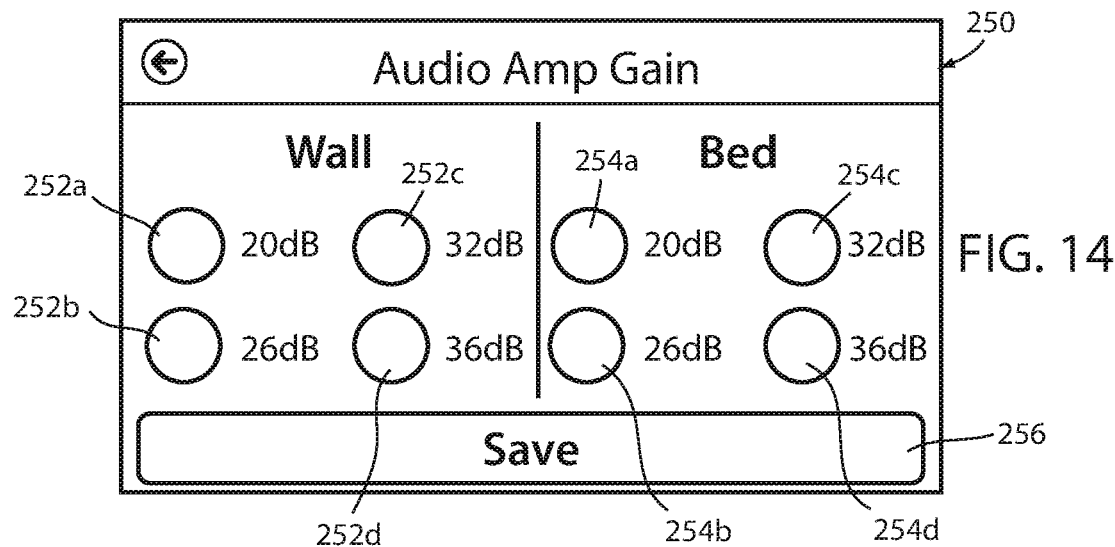
FIG. 14 is an illustrative audio gain screen displayable on the display of any of the patient support apparatuses disclosed herein or a display of any of the off-board electronic devices disclosed herein.

If a user selects audio amp gain option 202e of master configuration control screen 200 (FIG. 9), display 52 of control panel 54a displays an audio amp gain control screen 250, such as shown in FIG. 14. Audio amp gain control screen 250 includes a plurality of wall setting options 252a-d and a plurality of patient support apparatus 20, 20a setting options 254a-d. The wall settings 252a-d control the amount of amplification that headwall unit 144 applies to the audio signals sent between communications outlet 64 and patient support apparatus 20, 20a. The patient support apparatus settings 254a-d control the amount of amplification that patient support apparatus 20, 20a applies to the audio signals sent between patient support apparatus 20 and communications outlet 64 (or between patient support apparatus 20a and headwall unit 144, 144a. As can be seen in FIG. 14, the setting options includes selections for gains of 20 decibels (dB), 26 dB, 32 dB, and 36 dB.

In some embodiments, the gains shown in FIG. 14 refer to the amplification of the audio signals received from nurse call system 70, which are the voice signals received from the remotely positioned nurse (via a specific pin of communications outlet 64). In other embodiments, the gains shown in FIG. 14 refer to the amplification of the audio signals received from the television 72 (via a different pin of communications outlet 64). In still other embodiments, the gains shown in FIG. 14 refer to the amplification of both the audio signals received from nurse call system 70 as well as the audio signals received from television 72. In still other embodiments, patient support apparatuses 20, 20a may include settings allowing the user to separately control the gains for the television audio signals and the nurse call system audio signals received from communications outlet 64.

Figure 15:
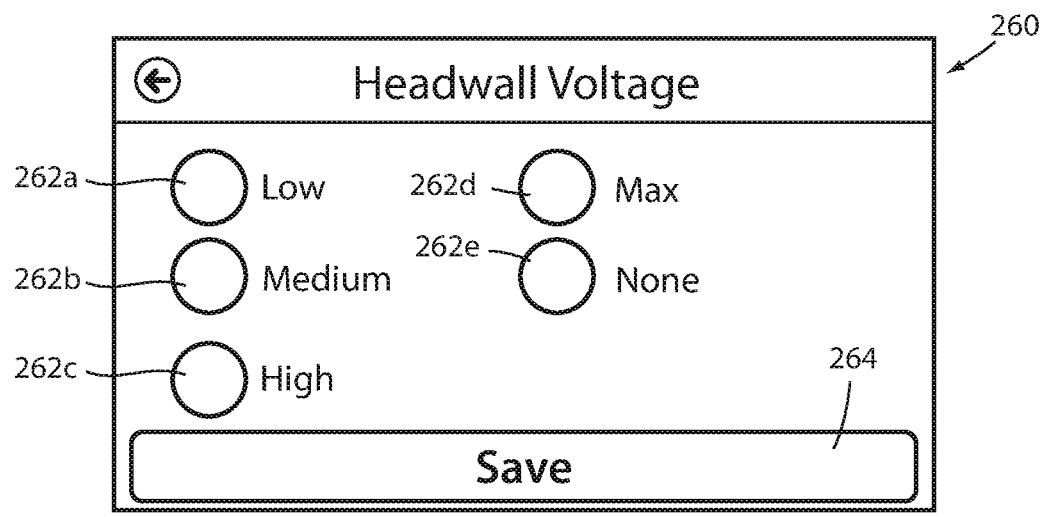
FIG. 15 is an illustrative headwall voltage screen displayable on the display of any of the patient support apparatuses disclosed herein or a display of any of the off-board electronic devices disclosed herein.

If a user selects headwall voltage option 202f of master configuration control screen 200 (FIG. 9), display 52 of control panel 54a displays a headwall voltage control screen 260, such as shown in FIG. 15. Headwall voltage control screen 260 includes a plurality of voltage options 262a-e. Voltage options 262a-e control how headwall unit 144, 144a or patient support apparatus 20, 20a interprets the voltages applied by the nurse call system 70 between pins 16 and 29 and between pins 19 and 28. These voltages are used by patient support apparatus 20 to control the operation of nurse answer light 114 and nurse call lights 116, respectively.

Different nurse call systems 70 apply different voltages between pins 16 and 29 when a remotely positioned nurse answers a patient's call from patient support apparatus 20, 20a. Similarly, different nurse call system 70 apply different voltages between pins 19 and 28 when a nurse call is placed. In order for patient support apparatus 20, 20a to know when to illuminate lights 114 and 116, it must be configured to recognize what voltages are applied by nurse call system 70 between these two pairs of pins when a nurse answers a call and when a patient places a call, and what voltages might otherwise be present on these pins but not indicative of either a nurse answer or a patient call. Headwall voltage control screen 260 allows a user to tell patient support apparatus 20 what voltage levels on these pins should be interpreted as indicating that a nurse answered a call and what voltage levels should be interpreted as the nurse call system acknowledging that a patient has placed a call to a nurse (and these, in turn, tell patient support apparatus 20, 20a when to illuminate lights 114 and 116). At whatever voltage level the user selects, patient support apparatus 20, 20a is configured to illuminate lights 114 and 116 if the voltage exceeds the selected voltage, but to ignore (i.e. not turn on lights 114 and 116) if voltage is present between these pins but it does not exceed the configured voltage.

If the user selects "low voltage" option 262a of screen 260, controller 112 (for patient support apparatuses 20) or controller 184 (for patient support apparatuses 20a) illuminates nurse answer light 114 if the voltage between pins 16 and 29 exceeds the voltage corresponding to the "low voltage" of option 262a, and controllers 112, 184 illuminate nurse call light 116 if the voltage between pins 19 and 28 exceeds the voltage corresponding to the "low voltage" of option 262a. If the user selects "medium voltage" option 262b of screen 260, controller 112 (for patient support apparatuses 20) or controller 184 (for patient support apparatuses 20a) does the same thing, but only if the voltage exceeds the "medium voltage" option 262b. That is, controller 112, 184 illuminate nurse answer light 114 if the voltage between pins 16 and 29 exceeds the voltage corresponding to the "medium voltage" of option 262b, and controllers 112, 184 illuminate nurse call light 116 if the voltage between pins 19 and 28 exceeds the voltage corresponding to the "medium voltage" of option 262b. If the user selects "high voltage" option 262c or "max voltage" option 262d of screen 260, controller 112, 184 illuminates lights 114 and 116 in the same manner, but only if the voltage between the aforementioned pins exceeds a high or maximum level. Finally, if the user selects the "none" option 262e of screen 260, controller 112, 184 illuminates lights 114 and 116 if any non-zero voltage is detected between the aforementioned pins.

Although the specific numerical voltage levels that correspond to the low, medium, high, and max options 262a-d of FIG. 15 may vary, in some embodiments, the "low" option refers to three volts, the "medium" option refers to ten volts, the "high" option refers to twenty-five volts, and the "max" option refers to thirty-two volts. Other voltage levels, of course, may be used. Further, in some embodiments, headwall voltage control screen 260 may be modified to allow a user to input a specific numeric value, instead of, or in addition to, choosing one of the predefined voltage options 262a-e.

Each of controls screens 210, 220, 230, 240, 250, and 260 includes a "save" option 214, 224, 234, 244, 256, and 264, respectively. When the user activates these save options, headwall communications controller 112 stores the configuration option(s) selected by the user in a memory onboard patient support apparatus 20, 20a. If patient support apparatus 20, 20a is in communication with communications outlet 64 via nurse call cable 66, headwall communications controller 112 uses these saved configuration settings when communicating with communications outlet 64. If patient support apparatus 20a is wirelessly communicating with communications outlet 64 via headwall unit 144, 144a, patient support apparatus 20a transmits the saved configuration settings to headwall unit 144, 144a, and headwall unit controller 184 saves these configuration settings in a memory onboard headwall unit 144, 144a. Headwall module controller 184 thereafter uses these saved settings when communicating with communications outlet 64.

Patient support apparatus 20a is configured, in some embodiments, to act as a communications interface for headwall units 144, 144a. That is, any changes to be made to the configuration of headwall units 144, 144a are implemented via patient support apparatus 20a. Such changes may be implemented by changing any of the selected options on control screens 210, 220, 230, 240, 250, and/or 260, which are then stored in the memory of patient support apparatus 20, 20a and also transmitted to whichever headwall unit 144, 144a the patient support apparatus 20a is in communication with (if any). Also, as previously noted, such configuration changes may be made using an electronic device 94 executing remote control application 140. Remote control application 140, in some embodiments, displays screens similar to, or the same as, screens 210, 220, 230, 240, 250, and/or 260 on the display of devices 94 and thereby allows the user to select the configuration options shown on these screens. When remote control application 140 displays such configuration options on the screen of an electronic device 94, it may also display a room number, a patient support apparatus 20, 20a identifier, and/or a headwall unit 144, 144a identifier that specifies which patient support apparatus 20, 20a and/or which headwall unit 144, 144a the configuration settings are to be applied to. The new settings are then sent by remote control application 140 to the patient support apparatus 20, 20a. Patient support apparatus 20a then shares the new settings with whichever headwall unit 144, 144a it is in communication with, if any.

In some embodiments, when headwall unit 144, 144a is first installed in a healthcare facility, it does not include any configuration settings stored in its memory. In such embodiments, headwall unit 144, 144a may be programmed to automatically request these configuration settings from the first patient support apparatus 20a it successfully establishes a communications link with. If the patient support apparatus 20a does not include any stored settings in its memory to transfer to headwall unit 144, 144a, it may be configured to display an error message on display 52 indicating to the user that headwall unit 144, 144a and/or patient support apparatus 20a need to be configured in order to communicate with room devices 72, 74, 78 and/or nurse call system 70.

Once a headwall unit 144, 144a receives a complete set of configuration settings from a patient support apparatus 20a, it does not thereafter request such configuration settings from a patient support apparatus 20a, even if a new patient support apparatus 20a is moved into communication with the headwall unit 144, 144a. Instead, it continues to use the configuration settings it received, regardless of which patient support apparatus 20a it is currently in communication with. In some embodiments, headwall units 144, 144a are configured to update their configuration settings only if a connected patient support apparatus 20a sends a command to change its configuration settings. In some embodiments, patient support apparatus 20a is configured to automatically send such a command to whichever headwall unit 144, 144a it is currently in communication with if the user enters any new configuration settings while the patient support apparatus 20a is communicating with the headwall unit 144, 144a. If patient support apparatus 20a is not currently communicatively linked to any headwall unit 144, 144a, it does not send such configuration data until it later links to a headwall unit 144, 144a and the user manually prompts patient support apparatus 20a to send the new configuration data.

Once a headwall unit 144, 144a is configured with a complete set of configuration settings, it is programmed in some embodiments to automatically send a copy of those configuration settings to whichever patient support apparatus 20a that links with headwall unit 144, 144a. (Headwall units 144, 144a are programmed, in some embodiments, to only link to a single, adjacent patient support apparatus 20a). The patient support apparatus 20a then displays those settings on display 52 (in response to a user navigating to one or more settings screens) and the user is free to edit them, if desired.

Although patient support apparatus 20a may contain its own set of configuration settings stored in its memory, it does not use those settings, in at least one embodiment, unless it links to a headwall unit 144, 144a that does not have any configuration settings stored thereon (in which case patient support apparatus 20a sends its configuration settings to the unconfigured headwall unit 144, 144a). The reason that patient support apparatus 20a does use any configuration settings it contains in its onboard memory is because it relies on headwall units 144, 144a to contain the correct set of configuration settings for the particular communications outlet 64 to which the headwall unit 144, 144a is associated. This allows the patient support apparatus 20a to be moved to different locations in the healthcare facility without having to change any settings on the patient support apparatus 20a. Instead, the patient support apparatus 20a simply uses the configuration settings that are stored in the headwall unit 144, 144a to which it is communicatively coupled.

In other words, every time a patient support apparatus 20a is moved to a different room, and/or some other location, having a different headwall unit 144, 144a that may contain different configuration data, the patient support apparatus 20a does not need to be manually changed in any manner in order for it to successfully communicate with the specific communications outlet 64 that that particular headwall unit 144, 144a is coupled to. Instead, because the headwall units 144, 144a are all configured for the specific communications outlet 64 to which they are coupled (and the room devices 72, 74, 78 and nurse call system 70 coupled thereto), the patient support apparatus 20a that communicates with that headwall unit 144, 144a does not need to change any of its communication protocols in order to correctly communicate with room devices 72, 74, 78 and/or nurse call system 70.

By retaining the configuration data for a particular set of room devices 72, 74, 78 and/or nurse call system 70 in a headwall unit 144, 144a positioned within a particular room, patient support apparatus 20a can, in some embodiments, be programmed to communicate with all headwall units 144, 144a in the same manner, regardless of whether the headwall units 144, 144a are coupled to different brands of nurse call systems and/or regardless of whether they are coupled to different brands or types of room devices 72, 74, and/or 78. This avoids the need for the patient support apparatuses 20a to be changed each time they are moved to a different room, or other location, having different room devices 72, 74, 78 and/or a different nurse call system 70 installed. Instead, patient support apparatus 20a communicates with the associated headwall unit 144, 144a in the same manner and allows the headwall unit 144, 144a to "convert" those communications to the proper format for conveying to headwall communications outlet 64.

In some embodiments, patient support apparatus 20a may be configured to not store its own set of configuration settings data, but instead transfer any changes or data that are input via any of the control screens of FIGS. 10-15 to the associated headwall unit 144, 144a without retaining such data in its own onboard memory. This includes any configuration settings that are set or edited via remote control application 140. Such remotely entered or edited configuration settings are passed to patient support apparatus 20a, which forwards them to its associated headwall unit 144, 144a without saving them.

In at least one alternative embodiment, patient support apparatus 20a is configured to communicate with headwall unit 144, 144a in a different manner depending upon how the headwall unit 144, 144a is configured. Specifically, in this alternative embodiment, if headwall unit 144, 144a has been configured to communicate with television 72 via the "traditional" option 212e of FIG. 10, patient support apparatus 20a is configured to send the same command to the headwall unit 144, 144a in response to the user activating any of controls 50l-50r. The selected command may be a command that utilizes little bandwidth, thereby leaving more bandwidth for other communications between headwall unit 144, 144a and patient support apparatus 20a. In still other embodiments, as mentioned above, patient support apparatus 20a may be configured to communicate with its associated headwall unit 144, 144a in the same manner, regardless of how the associated headwall unit 144, 144a is configured.

In summary, when an unconfigured headwall unit 144, 144a communicatively coupled to a patient support apparatus 20*a*, it requests a set of configuration data from the patient support apparatus 20*a* and stores it in its own memory. Headwall unit 144, 144*a* thereafter uses this stored configuration data when communicating with its associated communications outlet 64, and continues to use this configuration data unless it receives a command to change the configuration data from patient support apparatus 20*a* (which may originate from patient support apparatus 20 itself, or from remote control application 140). When a configured headwall unit 144, 144*a* establishes communication with a patient support apparatus 20*a*, the headwall unit 144, 144*a*, sends its configuration data to the patient support apparatus 20*a* so that the data can be displayed to the user and/or edited. However, unless the user manually changes the configuration data, the configured headwall unit 144, 144*a* will continue to use its configuration data for its communications with communication outlet 64.

For both patient support apparatuses 20, 20*a* and headwall units 144, 144*a*, the configuration data is used by configuration circuitry 132 to ensure proper communication with the associated communications outlet 64. When any changes are made to the configuration data, the configuration circuitry 132 automatically makes corresponding changes, as necessary, via software. Thus, there is no need for a user to manually change any dipswitches, or make any other physical changes, to the configuration circuitry 132 when the configuration data is changed. In this manner, both patient support apparatuses 20, 20*a* and headwall units 144, 144*a* can be configured using control panels on patient support apparatus 20, 20*a* and/or electronic devices 94 without having to take any physical actions other than selecting the desired settings on these control panels.

Patient support apparatus 20, 20*a* is configured to display its current configuration settings data on display 52 in response to a user navigating to an appropriate set of screens. This may be done via the screens shown in FIGS. 10-15. In other words, although FIGS. 10-15 show a plurality of options that are all illustrated in the drawings as being unselected, it will be understood that, patient support apparatus 20, 20*a* is configured to show which options were previously checked (if patient support apparatus 20, 20*a* was previously configured or previously used to configure a headwall unit 144, 144*a*). Thus, the control screens of FIGS. 10-15 are not only used to change configuration settings, but also to view the current configuration settings.

In some embodiments, patient support apparatus 20*a* is configured to display the configuration settings on the screens of FIGS. 10-15 in different manners, depending upon whether patient support apparatus 20*a* is currently communicating with a headwall unit 144, 144*a* or not. In such embodiments, if patient support apparatus 20*a* is currently in communication with a headwall unit 144, 144*a* and the user navigates to any of the screens of FIGS. 10-15, patient support apparatus 20*a* displays the configuration settings thereon that are stored in the memory of the headwall unit 144, 144*a* (if any) that it is currently in communication with (it displays this data after receiving it and/or requesting it from the headwall unit 144, 144*a*). Further, in such embodiments, if patient support apparatus 20*a* is currently not in communication with a headwall unit 144, 144*a* and the user navigates to any of the screens of FIGS. 10-15, patient support apparatus 20*a* displays the configuration settings (if any) that it has stored in its own onboard memory. Thus, in these embodiments, patient support apparatus 20*a* is configured to automatically always display the configuration settings of any headwall unit 144, 144*a* it is in communication with, and to only display any configuration settings stored on the patient support apparatus 20, 20*a* if it is not currently in communication with a headwall unit 144, 144*a*. In some of these embodiments, patient support apparatus 20*a* may include a control for allowing the user to see both the configuration settings of the headwall unit 144, 144*a* and the patient support apparatus 20*a* regardless of whether or not the patient support apparatus 20 is communicating with a headwall unit 144, 144*a* or not.

In some embodiments, headwall units 144, 144*a* are constructed to include any or all of the functionality of the wireless headwall units disclosed in commonly assigned U.S. patent application Ser. No. 14/819,844 filed Aug. 6, 2015, by inventors Krishna Bhimavarapu et al. and entitled PATIENT SUPPORT APPARATUSES WITH WIRELESS HEADWALL COMMUNICATION, the complete disclosure of which is incorporated herein by reference.

FIG. 16 illustrates a portable configuration tool 400 that may be used to configure any of the headwall units 144, 144*a* without the need for a patient support apparatus 20, 20*a*, as well as without the need for a local area network 80. That is, configuration tool 400 allows a user to directly communicate with a nearby headwall unit 144, 144*a* and change one or more configuration settings on the headwall unit 144, 144*a*. In addition, configuration tool 400 may also read the configuration settings on the nearby headwall unit 144, 144*a* and display them to the user, as well as perform tests on the headwall unit 144, 144*a* and/or gather diagnostic information from the headwall unit 144, 144*a*, as will be discussed in greater detail below. Configuration tool 400 thereby enables technicians to more easily install and configure headwall units 144, 144*a* throughout a healthcare facility. Further, by configuring each headwall unit 144, 144*a* with the necessary information for it to properly communicate with the healthcare facility's existing communication infrastructure, it is not necessary to make any configuration adjustments to any of the patient support apparatuses 20*a*. Instead, such adjustments can be made to the headwall units 144, 144*a*.

Configuration tool 400 is operated by a technician by coupling it to a portable computer 402 (FIG. 16). Such coupling may take on any of a variety of different forms, such as wired coupling or wireless coupling. In at least one embodiment, configuration tool 400 is coupled to portable computer 402 by a conventional Universal Serial Bus (USB) cable 406, such as is shown in FIG. 16. It will be understood that other types of cables may be used, such as, but not limited to, one or more types of network cables (e.g. CAT 5, CAT 5E, etc.), a Firewire cable, an RS-232 cable, an RS-485 cable, etc. It will also be understood that, in place of a wired cable 406, portable computer 402 may be coupled to configuration tool 400 via a wireless connection, such as, but not limited to, a Bluetooth connection, a ZigBee connection, or, in at least some cases, a WiFi connection.

Portable computer 402 may be any computer that is adapted to execute a configuration software application 404 (FIG. 19), such as, but not limited to, a conventional laptop, smart phone, and/or tablet computer. Configuration software application 404 is written, in at least some embodiments, to be compatible with a Microsoft Windows based operating system, or an Apple iOS operating system, or a Google Android operating system, or still another conventional operating system.

Configuration tool 400 is a handheld device that may be carried by an authorized individual to areas in front of a headwall unit 144, 144*a* that is to be configured, tested, or read. Configuration tool 400 is adapted to receive instructions from the portable computer 402 when it operates configuration software application 404. Such instructions cause configuration tool 400 to perform one or more of the following actions: establish IR and RF communication links with a nearby headwall unit 144, 144a (e.g. one that is within the relatively small IR range of the headwall unit 144, 144a (e.g. about 5 to 10 feet)); read the configurations settings (if any) stored in the headwall unit 144, 144a and report them to portable computer 402 for display thereon; send new configuration settings to headwall unit 144, 144a with instructions to install those configuration settings; send test commands to headwall unit 144, 144a with instructions to perform the various commands; and/or read diagnostic data from the headwall unit 144, 144a and report it to portable computer 402 for display thereon.

Figure 18:
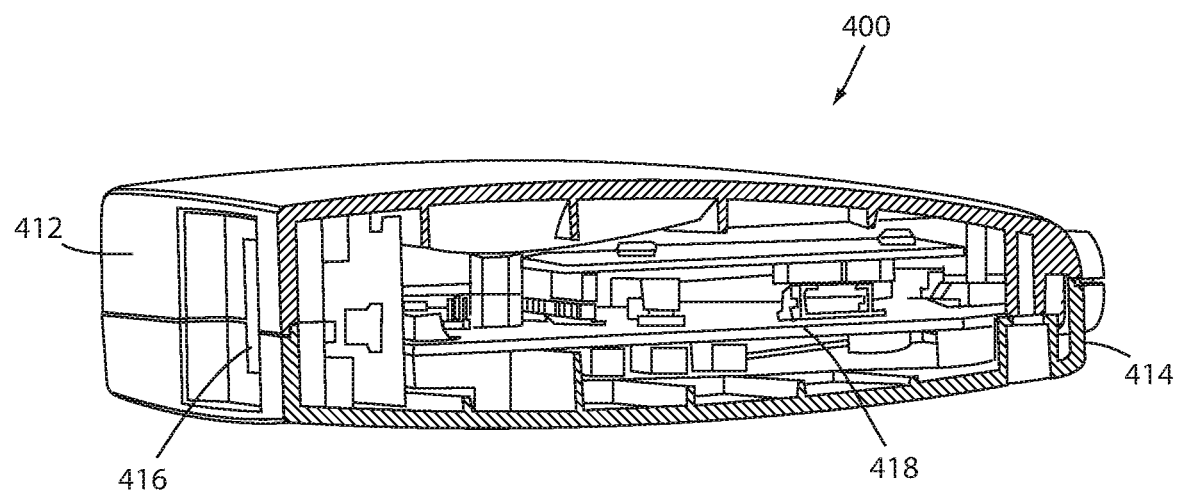
FIG. 18 is a sectional view of the configuration tool of FIG. 17 taken along the plane labeled line XVIII-XVIII in FIG. 17.

As shown more clearly in FIGS. 17 and 18, configuration tool 400 includes a housing 410 having a front end 412 and a back end 414. Front end 412 includes an IR opening 416 that is provided in order to allow an IR transceiver built into configuration tool 400 (as discussed below) to emit and detect infrared light. Back end 414 includes an opening for cable 406. As shown more clearly in FIG. 18, configuration tool 400 includes an internal circuit board 418 on which a controller 420 (FIG. 19) and other associated circuitry is mounted.

Controller 420, like the other controllers 108, 110, 112 etc. discussed herein, may take on a variety of different forms. In at least one embodiment, controller 420 is a conventional microcontroller. In other embodiments, controller 420 may use a variety of other types of circuits—either alone or in combination with one or more microcontrollers—such as, but not limited to, any one or more microprocessors, field programmable gate arrays, systems on a chip, volatile or nonvolatile memory, discrete circuitry, and/or other hardware, software, or firmware that is capable of carrying out the functions described herein, as would be known to one of ordinary skill in the art. Such components can be physically configured in any suitable manner, such as by mounting them to one or more circuit boards, or arranging them in other manners, whether combined into a single unit or distributed across multiple units. The instructions followed by controller 420 when carrying out the functions of tool 400 described herein, as well as the data necessary for carrying out these functions, are stored in a corresponding memory 422 (FIG. 19) within tool 400 that is accessible to controller 420. Memory 422 may non-volatile flash memory or another suitable type of memory.

Figure 19:
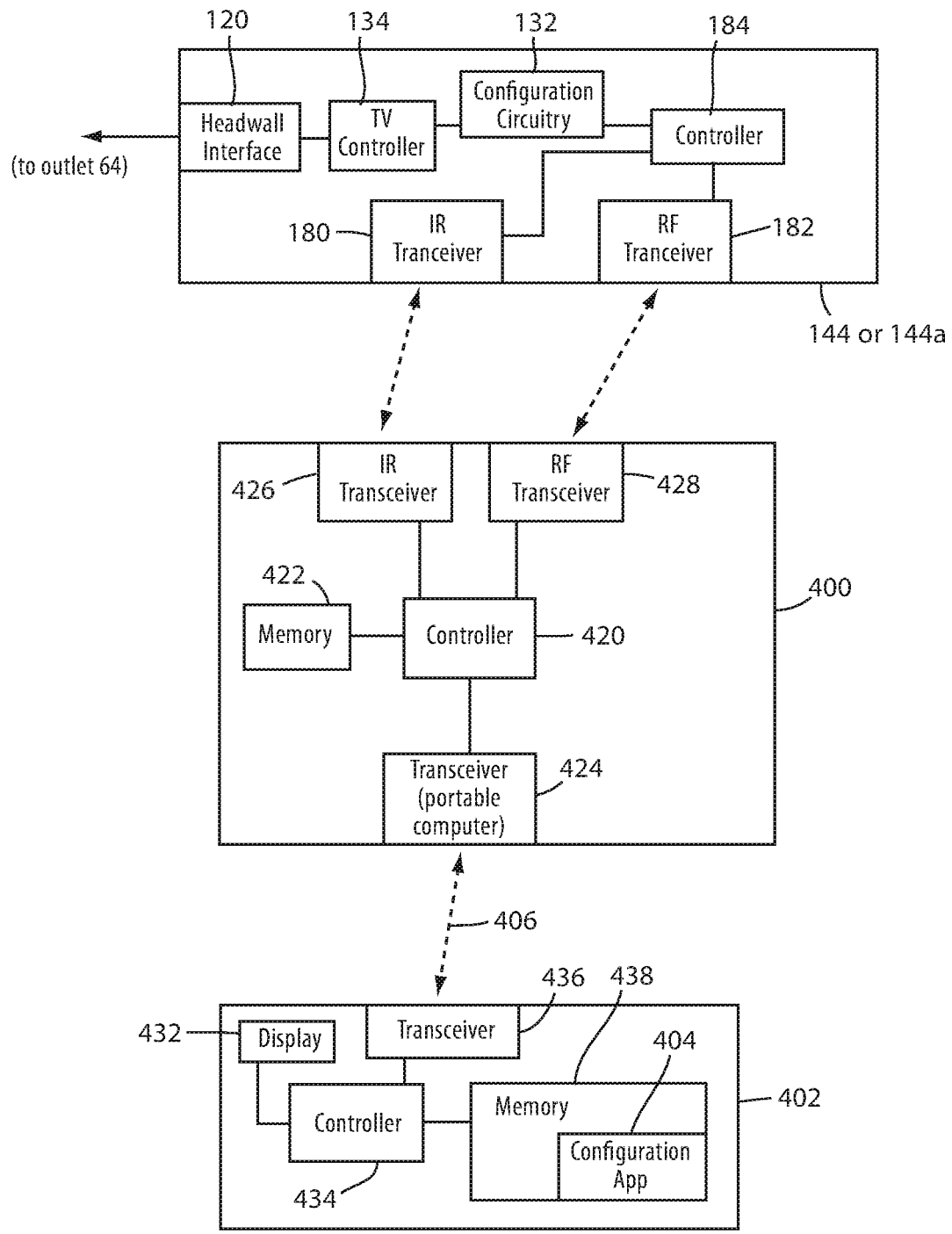
FIG. 19 is a block diagram of the configuration tool of FIG. 16.

As shown more clearly in FIG. 19, in addition to controller 420, portable configuration tool 400 also includes a transceiver 424, an infrared (IR) transceiver 426, and a radio frequency (RF) transceiver 428. Tool 400 may also include additional structures not shown in FIG. 19 such as, but not limited to, one or more indicators and/or additional circuitry for carrying out additional functions. Transceiver 424 is used to communicate with portable computer 402 and is, in at least some embodiments, a conventional USB transceiver. IR transceiver 426 is adapted to use infrared communications to communicate with IR transceiver 180 of a nearby headwall unit 144, 144a. RF transceiver 428 is used to communicate with the RF transceiver 182 of the same headwall unit 144, 144a that IR transceiver 426 is in communication with. In some embodiments, RF transceiver 182 is a Bluetooth transceiver.

As is also shown in FIG. 19, portable computer 402 includes a controller 434, a transceiver 436, a memory 438, and a display 432. Portable computer 402, as noted, may be a conventional computer and therefore may include a number of additional components, such as, but not including, a keyboard, a mouse, one or more coprocessors, additional ports (e.g. a network port, additional USB ports, an HDMI port, headphone and/or microphone jack, etc.), and any other components that are typically found on conventional portable computers. When computer 402 is implemented as a smart phone, it may include a touch screen, a SIM card, and/or other components conventionally found in smart phones.

Controller 434 may be a conventional microcontroller (or multiple microcontrollers) that, in at least one embodiment, executes a conventional operating system and one or more software applications that are stored in memory 438. Memory 438 may comprise one or more types of conventional non-volatile memory such as, but not limited to, flash memory, a hard drive, a disk, etc. Display 432 may be a conventional computer display and/or screen. Transceiver 436, in at least one embodiment, is a conventional USB transceiver that enables portable computer 402 to communicate with an external device, such as configuration tool 400, using a conventional USB cable 406.

Figure 20:
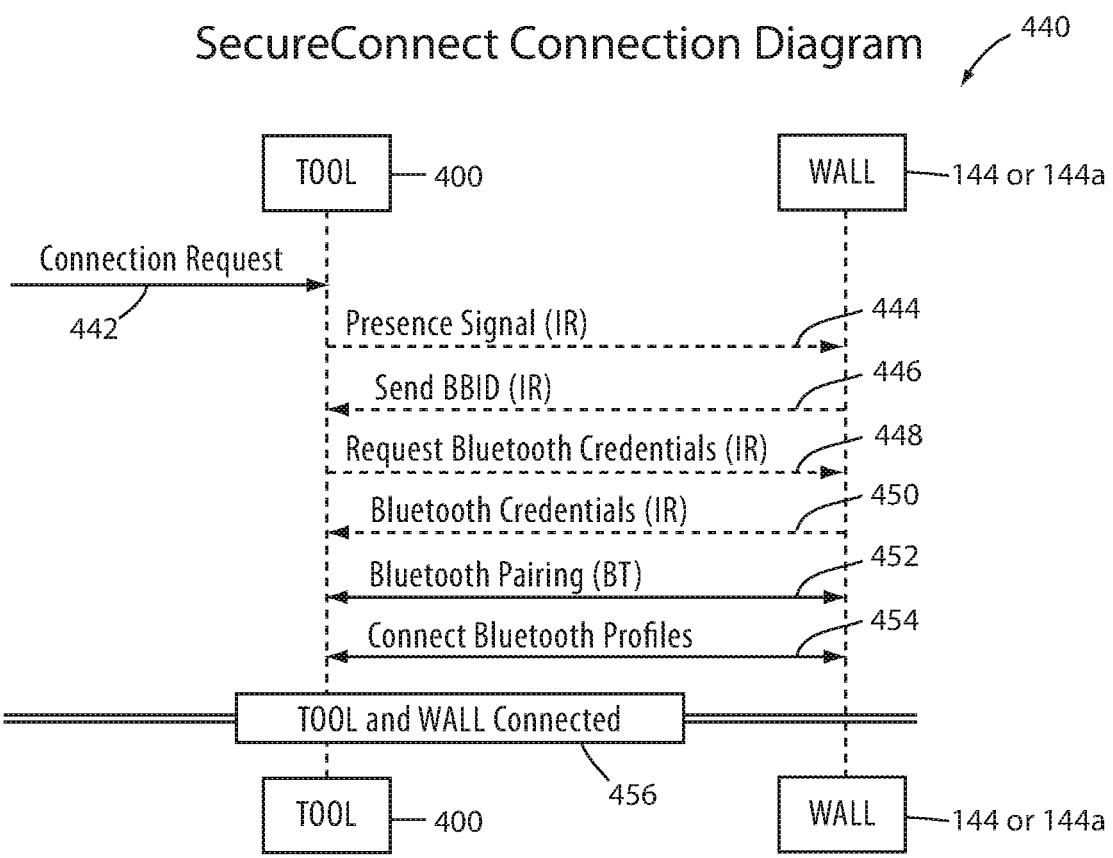
FIG. 20 is a diagram of a pairing process between the configuration tool and the headwall unit.

FIG. 20 illustrates a connection algorithm 440 executed by configuration tool 400 when establishing communications between itself and a nearby headwall unit 144, 144a. Although connection algorithm 440 is described as applying to the communication connection between configuration tool 400 and a nearby headwall unit 144, 144a, it will be understood that algorithm 440 can also and/or alternatively be used by one or more patient support apparatuses 20a to establish a wireless communication connection with a nearby headwall unit 144, 144a.

Algorithm 440 begins at an initial step 442 when controller 420 receives a request to establish a connection between tool 400 and headwall unit 144, 144a. This connection request typically comes from portable computer 402 in response to a user manipulating one or more controls on portable computer 402. The result of such control manipulation is the generation of a command sent over cable 406 to controller 420 of configuration tool 400. The command instructs controller 420 to set up a communication connection with a nearby headwall unit 144, 144a. As will be discussed in greater detail below, this connection request may be implemented by a user pressing on, or otherwise selecting, a "connect to new device" option displayed on the display 432 of portable computer 402 (see FIGS. 21-22). In some embodiments, as will be discussed in greater detail below, controller 420 is configured to automatically implement a connection request without receiving a command from portable computer 402. In such embodiments, controller 420 implements the connection request automatically in response to a connection being established between portable computer 402 and configuration tool 400.

After connection request is received at step 442, controller 420 proceeds to step 444 where it sends out an IR presence signal using IR transceiver 426. The IR presence signal is emitted through IR opening 416 and will be detected by a nearby headwall unit 144, 144a if the IR opening 416 is facing in the general direction of the headwall unit 144, 144a. Thus, the user of configuration tool 400 should point configuration tool 400 generally toward the headwall unit 144, 144a that he or she wishes to test, configure, and/or read. The IR presence signal informs the controller 184 of headwall unit 144, 144a that a compatible device (e.g. tool 400 or patient support apparatus 20a) is within a vicinity of the headwall unit 144, 144a. The IR presence signal also serves to request a unique identifier from headwall unit 144, 144a that distinguishes that particular headwall unit 144, 144a from all of the other headwall units 144, 144a that may be in that particular healthcare facility.

In response to the IR presence signal, controller 184 of headwall unit 144, 144a sends a response signal at step 446 to configuration tool 400 using its IR transceiver 180 (FIG. 20). The response signal is detected by IR transceiver 426 of configuration tool 400. The response signal includes the unique identifier of that particular headwall unit, sometimes referred to as a Bed Bay Identification (BBID) number. Controller 420 of configuration tool 400 uses the unique identifier as an address for subsequent RF communications between tool 400 and that particular headwall unit 144, 144a. This is done in order to ensure that configuration tool 400 doesn't pair its RF communications with a different headwall unit 144, 144a, which would otherwise be a possibility given the greater range and less directionality of RF communications versus IR communications. In other words, when configuration tool 400 eventually pairs with headwall unit 400 via Bluetooth communications (see, e.g. step 452 of FIG. 20), it will address the RF Bluetooth communications to the particular headwall unit 144, 144a having the unique identifier it received at step 446. In this manner, if another headwall unit 144, 144a that is within RF range of configuration tool 400 receives the Bluetooth RF messages sent from configuration tool 400, it will not respond to them because the RF messages are not addressed to that particular headwall unit 144, 144a. Instead, only the headwall unit 144, 144a with the address corresponding to the unique identifier received at step 446 will respond.

At step 448 (FIG. 20), configuration tool 400 responds to the receipt of the headwall unit 144, 144a's unique identifier by sending a request for Bluetooth credentials to that headwall unit 144, 144a. This request is sent via IR transceiver 426 and, like all IR transmissions from tool 400, is detected by IR transceiver 180 of headwall unit 144, 144a. In some embodiments, it may also include, and/or otherwise utilize, the unique ID received at step 446 as an address so that other headwall unit 144, 144a that might be within communication range do not act upon the Bluetooth credentials request.

At step 452 (FIG. 20), configuration tool 400 and headwall unit 144, 144a establish Bluetooth pairing. This pairing is accomplished using the unique identifier of the headwall unit 144, 144a that was received by the configuration tool 400 at step 446, as well as a unique identifier corresponding to configuration tool 400 that is transferred to headwall unit 144, 144a. The unique identifier of configuration tool 400 is sent to headwall unit 144, 144a at any suitable point during algorithm 440. In some embodiments, this is done with the initial signal sent at step 444, while in other embodiments, it may alternatively or also be done with any of the subsequent IR messages that tool 400 transmits to headwall unit 144, 144. The transfer of this unique configuration tool ID is done in order to allow headwall unit 144, 144a to uniquely address its RF communications to that particular configuration tool 400, rather than another configuration tool 400 that could possibly be within RF range of the headwall unit 144. Using the unique IDs of both headwall unit 144, 144a and configuration tool 400, these two devices are able to pair with each other without requiring the user to manually enter any information into tool 400 and/or manually take any other steps other than—in some cases, as noted previously— pointing tool 400 at the headwall unit 144, 144a and selecting the "connect to new device" option (see FIGS. 21 and 22). The pairing process between tool 400 and the headwall unit 144, 144a is therefore handled automatically in response to an instruction to carry out that pairing process with no additional action required other than having tool 400 pointed generally at the headwall unit 144, 144a of interest.

After the Bluetooth pairing takes place at step 452, one or more Bluetooth profiles are exchanged at step 454. These profiles are the same Bluetooth profiles 174 that are exchanged between headwall unit 144, 144a and patient support apparatus 20 that were previously discussed (see FIG. 8B). After these profiles 174 have been exchanged, algorithm 440 has successfully connected the configuration tool 400 to the nearby headwall unit 144, 144a. As will be discussed in greater detail below, the headwall unit 144, 144a may include one or more lights or other indicia that are controlled by controller 184 in a manner that provides visual feedback to the user of configuration tool 400 that the particular headwall unit 144, 144a has been successfully paired with configuration tool 400. Further, configuration tool 400 may send to portable computer 402 a message indicating it has successfully paired with headwall unit 144, 144a, and this message may be displayed by portable computer 402 on display 432 so that the user receives visual notification from configuration tool 400 of the pairing as well. The message may include the unique identifier of the headwall unit 144, 144a. In some embodiments, configuration tool 400 may include its own visual indicators (e.g. lights) to notify the user that is has successfully paired with a headwall unit 144, 144a, but in other embodiments, configuration tool 400 relies on the audio/visual indicators of portable computer 402 to convey to the user a notification that it has successfully paired with a headwall unit 144, 144a.

At step 456 of algorithm 440 (FIG. 20), the configuration tool 400 and headwall unit 144, 144a are successfully paired. Subsequent communications involve two components: (a) heartbeat messages exchanged between configuration tool 400 and headwall unit 144, 144a; and (b) communications of any user-commands from configuration tool 400 to headwall unit 144, 144a (and the appropriate responses to those commands from headwall unit 144, 144a). In other words, apart from the heartbeat communications, the content of the messages exchanged between configuration tool 400 and headwall unit 144, 144a will depend upon what the user desires to do with configuration tool 400. As noted previously, he or she may use tool 400 to change one or more configuration settings of headwall unit 144, 144a; to read one or more of the existing configuration settings of headwall unit 144, 144a; to test one or more features of headwall unit 144, 144a; and/or to gather diagnostic data from headwall unit 144, 144a.

The heartbeat messages exchanged between configuration tool 400 and headwall unit 144, 144a are the same as heartbeat messages that are exchanged between headwall unit 144, 144a and a nearby patient support apparatus 20a when that patient support apparatus 20a is paired with that particular headwall unit 144, 144a. In other words, although not described above, patient support apparatus 20a is configured, in at least some embodiments, to exchange heartbeat messages with whatever headwall unit 144, 144a it is paired with until such pairing terminates. The heartbeat messages exchanged between headwall unit 144, 144a and whatever device it is paired with (e.g. patient support apparatus 20a or configuration tool 400) may take on a variety of different forms. In some embodiments, the heartbeats alternate between IR and RF communications. In at least one embodiment, the heartbeat messages are implemented in any of the same manners as the heartbeat messages described in commonly assigned U.S. Pat. No. 10,679,489 issued to Bodurka et al. and entitled HOSPITAL HEADWALL COMMUNI- CATION SYSTEM, the complete disclosure of which is incorporated herein by reference. Other types of heartbeat messaging may alternatively or additionally be utilized.

In addition to the heartbeat messages, configuration tool 400 is configured to send additional commands to headwall unit 144, 144*a* based upon the inputs received from the user (and communicated to configuration tool 400 via portable computer 402 and cable 406). In at least one embodiment, controller 420 is configured to send such additional commands both using IR transceiver 426 and RF transceiver 428. In other embodiments, controller 420 is configured to use only a single one of the transceivers 426 and 428 unless a message is not properly acknowledged (in which case the message may be resent using the same transceiver 426 or 428, and/or resent using the other transceiver 426, 428). When sending the commands using both transceiver 426, 428, the commands are treated as redundant commands such that headwall unit 144, 144*a* only needs to receive the commands from one of its transceivers 180, 182 in order to take the appropriate action in response thereto.

FIGS. 21-26 illustrate several different screens that are shown on display 432 of portable computer 402 when it is executing configuration application 404 and configuration tool 400 is coupled thereto (via cable 406). It will be understood that these screens are merely illustrative of the types of screens that may be displayed thereon, and that substantial variations from these screens may be implemented. Such variations include, but are not limited to, the display of additional screens or fewer screens, the addition of extra information not shown on these screens, the removal of information shown on these screens, and/or a combination of any of the foregoing.

Home screen 460 (FIG. 21) is displayed on display 432 when software application 404 is first executed, as well as when the user is not using configuration tool 400 to perform one of the functional options shown thereon. These functional options include a connect-to-device function 462, a configure function 464, a test function 466, a get-device-info function 468, and a record module function 470. In addition to these functions, home screen 460 includes a status area 472 and a message area 474. Status area 472 provides an indication to the user of the current status of tool 400 with respect to both its connection to portable computer 402 and its connection to a headwall unit 144, 144*a*. Message area 474 provides messages to the user in response to the functions being performed and/or the current status of tool 400. In the example shown in FIG. 21, home screen 460 includes a message in message area 474 indicating that tool 400 is not connected to portable computer 402. This occurs when a cable 406 has not yet been coupled between portable computer 402 and tool 400.

Figure 21:
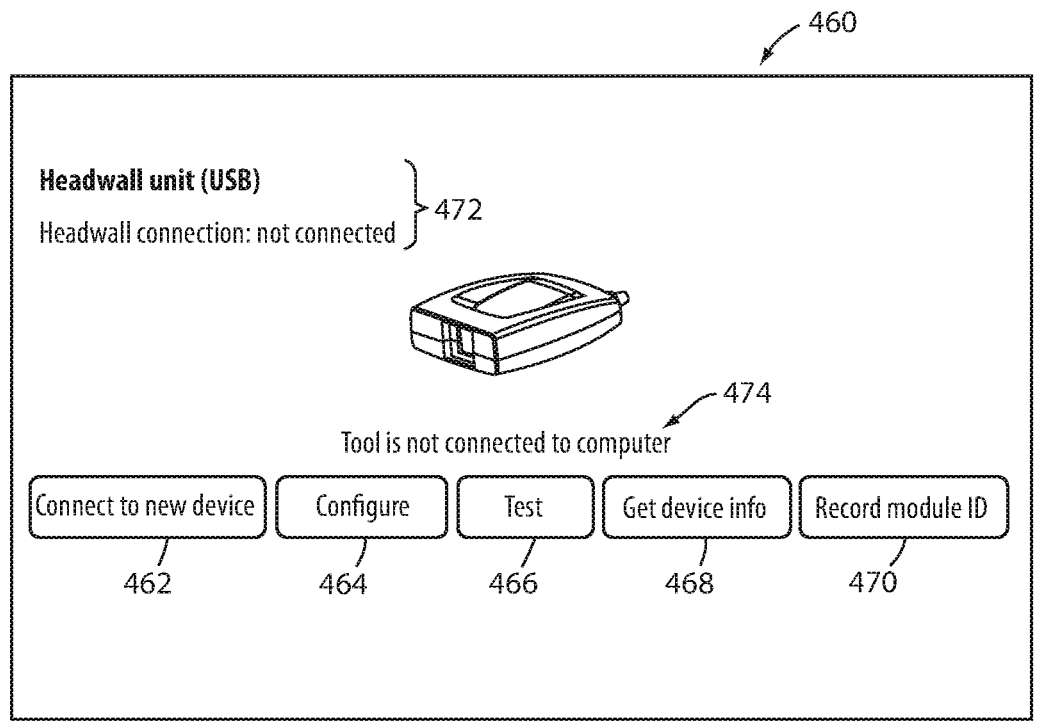
FIG. 21 is an example of a home screen displayed by a software application executed by the portable computer of FIG. 16 when the portable computer is not connected to the configuration tool.
Figure 22:
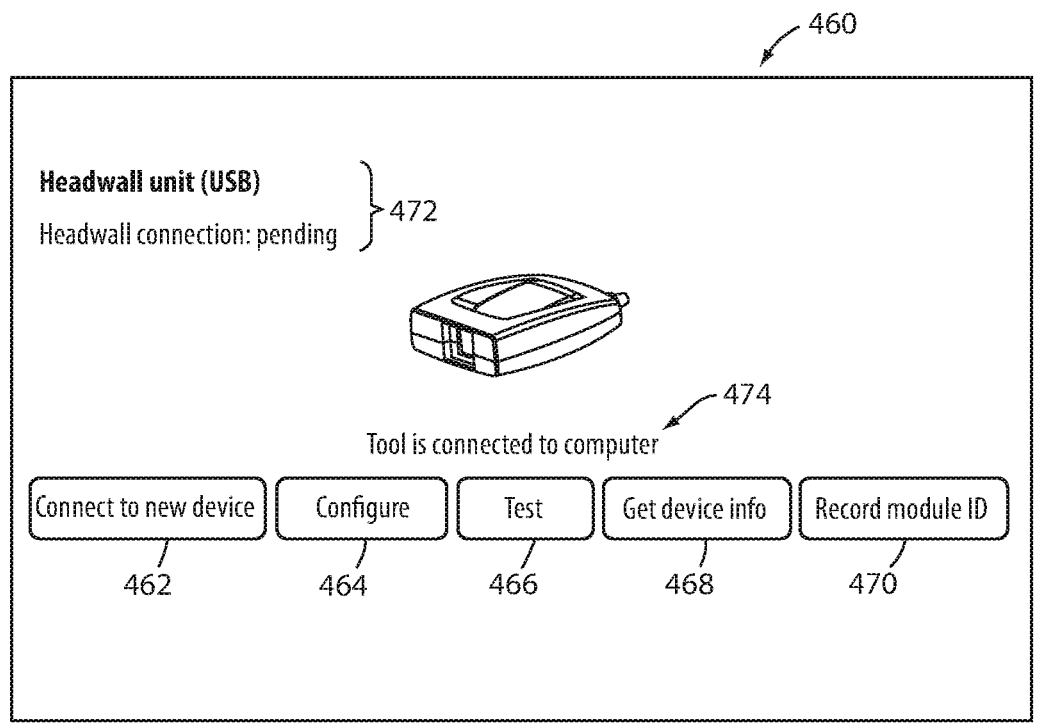
FIG. 22 is an example of the home screen of FIG. 21 that is displayed when the portable computer is connected to the configuration tool.

Home screen 460 may also display other information from what is shown in FIG. 21. One example of this is shown in FIG. 22, which shows different information displayed both in status area 472 and message area 474. The content of home screen 460 of FIG. 22 may be displayed when configuration tool 400 is successfully coupled to portable computer 402 (e.g. via cable 406) and configuration tool 400 is in the process of pairing with a particular headwall unit 144, 144*a*. The successful coupling of configuration tool 400 with portable computer 402 is reflected in the message displayed in message area 474 (e.g. "Tool is connected to the computer."). The fact that the tool 400 is attempting to pair with a headwall unit 144, 144*a* is reflected in the status area 472 (e.g. "headwall connection: pending"). Other manners of conveying these messages and/or statuses may, of course, be utilized.

In some embodiments, one or more of the functions 462-470 may be grayed out on the display 432 when tool 400 is not yet coupled to a headwall unit 144, 144*a*. This may be done to indicate to the user that such functions are not available until tool 400 is paired with a headwall unit 144, 144*a*. Alternatively, other means of conveying that one or more of these functions is not operable may be utilized. The message ("pending") displayed in status area 474 is displayed while controller 420 of tool 400 is executing steps 442-454 of algorithm 440. Once the pairing is complete and controller 420 reaches step 456, controller 420 sends a message to controller 434 of portable computer 402 instructing it to display an updated indication in status area 472, such as, but not limited to, "Headwall connection: connected."

In some embodiments, configuration tool 400 is constructed to automatically begin steps 444-456 of algorithm 440 in response to the user coupling tool 400 to portable computer 402 (and the user starting the execution of configuration application 404 on portable computer 402). In this manner, the user doesn't have to perform any manual steps to begin the pairing process other than coupling tool 400 to computer 402 and opening the application 404. In other embodiments, tool 400 may delay its attempt to couple to a headwall unit 144, 144*a* until the user selects the connect function 462. The selection of connect function 462, as well as any of the other functions 464-470, may be carried out in different ways, such as by the user moving the computer mouse until the mouse cursor is positioned over the desired function and the user clicks on the mouse, or such as by the user tapping on display 432 in the area where the desired function is displayed (if the display 432 is a touch screen display), or in still other manners.

In those embodiments where tool 400 is configured to automatically attempt to pair to a headwall unit 144, 144*a* upon the successful coupling of tool 400 to a portable computer 402 that is executing software application 404, the user does not need to activate the connect function 462 to initially connect to a headwall unit 144, 144*a*. Instead, he or she will only use the connect function 462 after he or she is done working with the initially paired headwall unit 144, 144*a* and wants to switch to pairing with a different headwall unit 144, 144*a*. When he or she activates the connect function 462, portable computer 402 sends a connection request instruction to controller 420 (step 442 of algorithm 440; FIG. 20), and controller 420 responds by re-executing steps 444-456 of algorithm 440 with whatever headwall unit 144, 144*a* tool 400 happens to be generally pointed toward at that particular moment. Thus, if a user wishes to switch to pairing with a different headwall unit 144, 144*a* than the one tool 400 is currently paired with, he or she should move tool 400 so that it is generally aimed at the different headwall unit 144, 144*a* before selecting the connect function 462. That is, the IR opening 416 of tool 400 should be pointed in the general direction of the different headwall unit 144, 144*a*.

Once tool 400 is successfully paired with a particular headwall unit 144, 144*a*, the user may command tool 400 to perform any of the functions 462-470 shown on home screen 460. The connect function 462 has been previously described. The configure function 464 is used to configure the communication settings of headwall unit 144, 144*a* so that they properly match the particular nurse call system 70 that is installed in that particular healthcare facility, as well as the particular communication protocol used by the television 72 in that particular room and/or the particular communication protocols used by the room light 74 and/or reading light 78 in that particular room (or bay of that room).

The test function 466 is used to instruct headwall unit 144, 144a to perform any of the functions that it normally performs while it is paired with a patient support apparatus 20a, thereby enabling the user to test if headwall unit 144, 144a is properly configured without requiring a patient support apparatus 20a to be coupled to headwall unit 144, 144a. The get-device-info function 468 is used to read what configuration settings and other information is currently onboard headwall unit 144, 144a. The record module ID function 470 is used to automatically populate a spreadsheet, or other data structure, stored onboard portable computer 402 with the unique ID of the particular headwall unit 144, 144a that is received at step 446. This automatic population of a spreadsheet is done so that the user of tool 400 can more easily pair the unique identifiers of each headwall unit 144, 144a with their particular locations within the healthcare facility, thereby enabling the headwall units 144, 144a to be used to provide location information to patient support apparatuses 20a.

Figure 23:
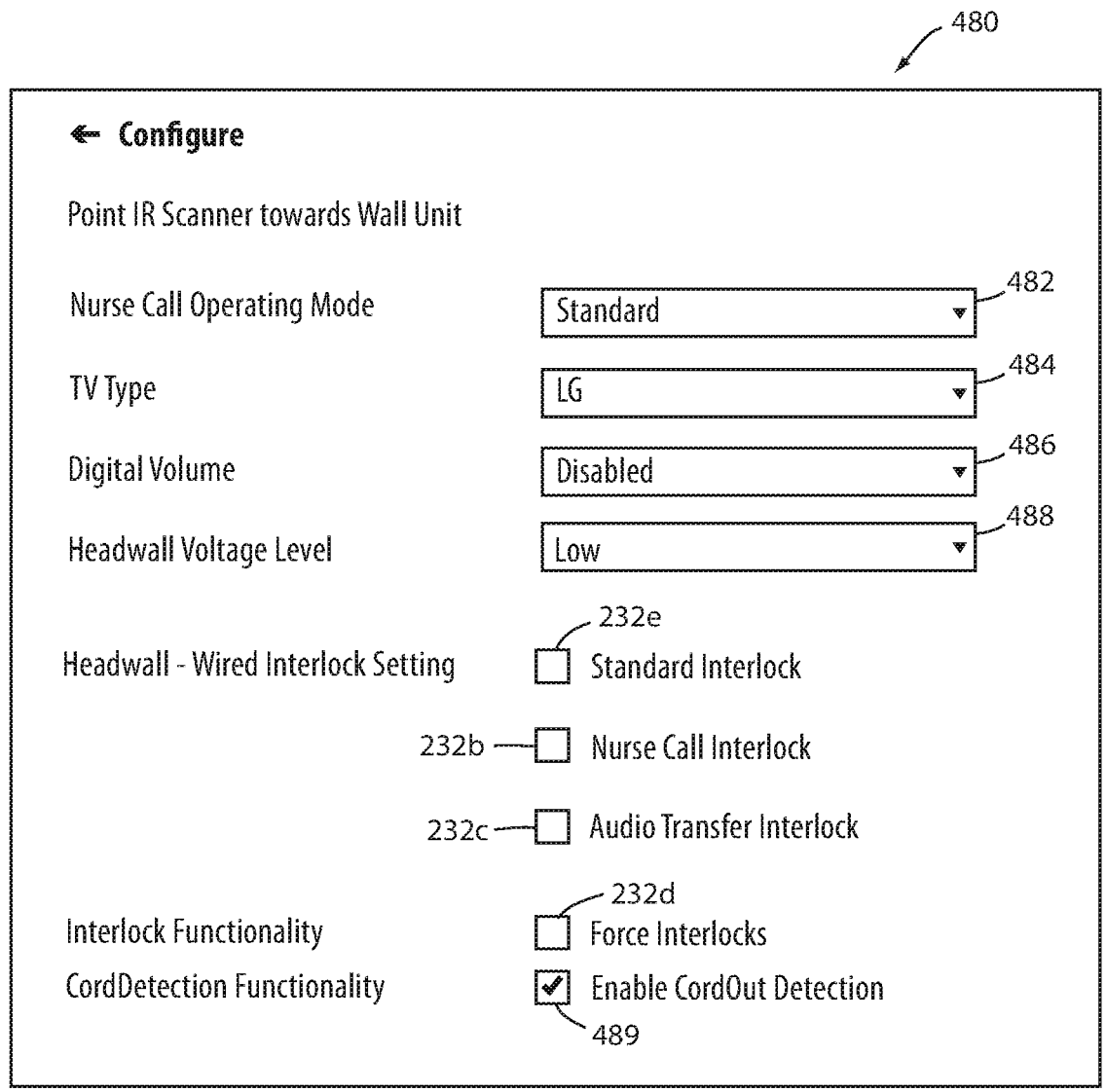
FIG. 23 is an example of a screen displayed by the software application executed by the portable computer of FIG. 16 after the user selects the "configure" function of FIG. 22.

Turning first to configure function 464 (FIGS. 21-22), if the user selects configure function 464, software application 404 is programmed to display a configuration screen, such as screen 480 of FIG. 23, on display 432 of portable computer 402. Configure screen 480 includes many, if not all, of the same configuration settings shown in FIGS. 10-15. These settings are shown in order to allow the user to change the settings on the paired headwall unit 144, 144a to those desired by the user. In other words, while the screens of FIGS. 10-15 are displayed on a patient support apparatus 20, 20a and used to control the configuration settings stored on patient support apparatus 20, 20a and/or on the paired headwall unit 144, 144a, the configure screen 480 is displayed on the screen 432 of the portable computer and allows the user to control the configuration settings of the paired headwall unit 144, 144a. Thus, configure screen 480 allows the user to make changes to headwall unit 144, 144a without utilizing a patient support apparatus 20 or 20a. In this manner, headwall units 144 and/or 144a may be easily configured without a patient support apparatus 20 or 20a being positioned nearby.

Configure screen 480 includes a nurse call operating mode field 482. Field 482 includes a plurality of different selections corresponding to different types of nurse call systems. In at least one embodiment, field 482 includes the same three options 222a-c shown in FIG. 11 and described above. Thus, field 482, when selected, will display a standard option 222a, a Hill-Rom option 222b, and a parallel option 222c. As explained previously, each of the options 222a-c corresponds to different manners in which nurse call systems communicate with patient support apparatus 20, 20a, and vice versa. More specifically, for a first type of nurse call system, a first set of pins in headwall interface 120 are electrically shorted together in response to a patient exit from patient support apparatus 20, 20a; for a second type of nurse call system, a second set of pins of headwall interface 120 are electrically shorted in response to a patient exit from patient support apparatus 20, 20a; and for a third type of nurse call system, both the first and second sets of pins are electrically shorted in response to a patient exit from the patient support apparatus 20, 20a.

Field 482 thus enables a user to tell headwall unit 144, 144a what type of nurse call system it is connected to via headwall interface 120 and outlet 64. More specifically, it instructs headwall unit which pins of headwall interface 120 are to be shorted when a patient support apparatus 20, 20a to which it is subsequently paired sends a message to headwall unit 144, 144a informing it that a patient exit has been detected by the exit detection system built into the patient support apparatus 20, 20a. Thus, by using tool 400 to instruct headwall unit 144, 144a how to react to an exit detection message from a paired patient support apparatus, it is not necessary for the patient support apparatus to be configured to a particular nurse call system, nor is it necessary for a user to utilize the patient support apparatus to configure headwall unit 144, 144a. Instead, the patient support apparatus can simply send a standardized exit detection message to headwall unit 144, 144a that is the same regardless of which healthcare facility the patient support apparatus is installed in (and/or what room it is in), and the headwall unit 144, 144a will know how to transfer that message to the installed nurse call system in the proper format so that the nurse call system is informed of the patient exit. In other words, headwall unit 144, 144a can be easily configured by tool 400 to correctly translate messages from patient support apparatus 20, 20a to the nurse call system 70 and/or room devices 72, 74, or 78, as well as to translate any messages from the nurse call system 70 or room devices 72, 74, or 78 back to the patient support apparatus 20, 20a.

After a user selects the desired nurse call system in field 482, software application 404 instructs controller 434 of portable computer 402 to send the selection to configuration tool 400 via transceiver 436 and cable 406. In response thereto, controller 420 of tool 400 sends a message to headwall unit 144, 144a (using transceivers 426 and/or 428) informing it of the selection. Controller 184 of headwall unit 144, 144a responds to this by changing the configuration setting of configuration circuitry 132 to match the desired selection (if the desired selection is not already implemented in configuration circuitry 132). In some embodiments, an acknowledgement may be sent back to tool 400 by controller 184 using either or both of transceivers 180, 182.

Changes to other settings of configuration circuitry 132 of headwall unit 144, 144a may be made using tool 400 and configure screen 480. Specifically, screen 480 includes a TV type field 484, a digital volume field 486, a headwall voltage level field 488, a plurality of interlock options 232a-c, e, and a cord out detection option 489. TV type field 484, when selected, displays a plurality of options for configuring headwall unit 144, 144a to communicate properly with different types of televisions 72. In at least one embodiment, TV type field 484 includes the same options 212a-g shown in FIG. 10 and described above. Digital volume field 486 allows a user to enable or disable the digital volume in the same manner that selecting or deselecting option 232d of FIG. 12 does, as was previously described. Headwall voltage field 488 includes, in at least one embodiment, the same options 262a-e shown in FIG. 15 and described above. Interlock options 232a-c and 232e are the same as interlock options 232a-c and 232e of FIG. 12, which were described above.

The cord out detection option 489 allows the user to configure headwall unit 144, 144a either in a manner in which a cord out alert is communicated to the nurse call system 70, or no cord out alert is communicated to the nurse call system 70. When the cord out alert is enabled, headwall unit 144, 144a is configured to send a message to the nurse call system via headwall interface 120 and communication outlet 64 whenever a patient support apparatus 20, 20a becomes unintentionally disconnected from the headwall unit 144, 144a. For patient support apparatuses 20, 20a that communication with headwall unit 144, 144a wirelessly, this disconnection occurs when the wireless communication between the headwall unit 144, 144a and the patient support apparatus 20, 20a terminates, such as when the patient support apparatus 20, 20a is moved out of the room and/or an error occurs with the communication. For patient support apparatuses 20, 20a that communicate with headwall unit 144, 144a via a cable (in some embodiments, headwall unit 144, 144a may be configured to accept a cable that is coupled at its opposite end to a patient support apparatus 20, 20a), the cord out alert is sent by headwall unit 144, 144a to the nurse call system when this cable is disconnected from headwall unit 144, 144a and/or from patient support apparatus 20, 20a. When the cord out alert is disabled, a user is free to move the patient support apparatus 20, 20a out of the room (whether by physically disconnecting the cable from headwall unit 144, 144a or by terminating the wireless link between the patient support apparatus 20, 20a and the headwall unit) without having the headwall unit send an alert to the nurse call system. Cord out option 489 thus enables a user of tool 400 to configure the headwall unit 144, 144a to either issue cord out alerts to the nurse call system or to not issue cord out alerts to the nurse call system 70.

All of the options shown on the configure screen 480, including those options that are grouped together within fields 482, 484, 486, or 488, are transmitted from portable computer to configuration tool 400 over cable 406 after the user has selected the desired options. In response to receiving these options, controller 420 of tool 400 transmits the selected option to headwall unit 144, 144a. Controller 184 then implements the selected options in configuration circuitry 132, TV controller 134, and/or elsewhere within headwall unit 144, 144a.

Figure 24:
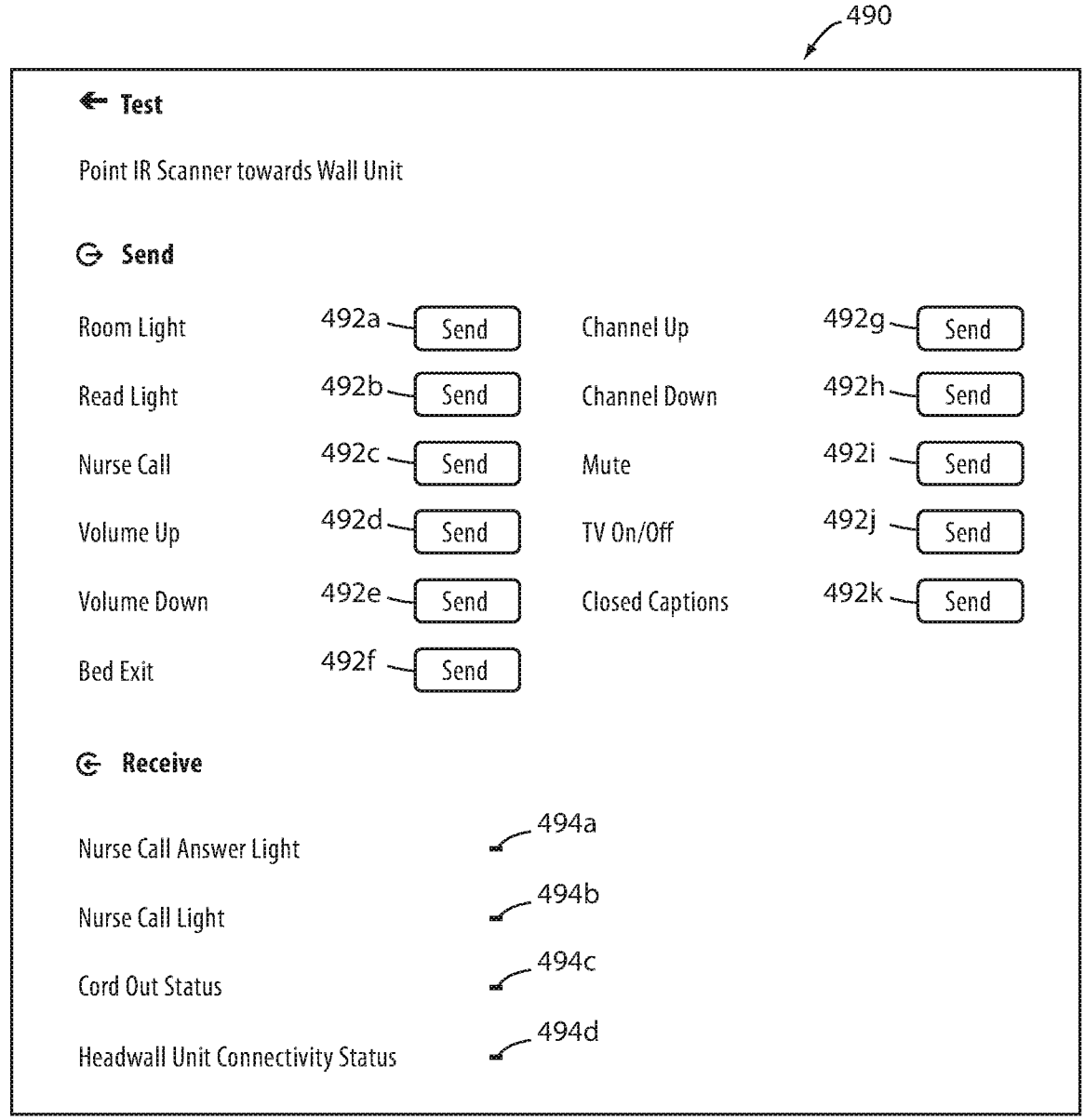
FIG. 24 is an example of a screen displayed by the software application executed by the portable computer of FIG. 16 after the user selects the "test" function of FIG. 22.

FIG. 24 shows an example of a test screen 490 that is displayed by software application 404 on the display 432 of portable computer 402 when the user selects the test function 466 on home screen 460. Test screen 490 includes a plurality of test options 492a-k that enable a user of configuration tool 400 to test the functionality of headwall unit 144, 144a. That is, for each option 492 that the user selects, software application 404 is configured to send a test message to configuration tool 400 via cable 406 (and transceivers 436 and 424). In response to the test message, controller 420 of configuration tool 400 is configured to send one or more messages to headwall unit 144, 144a that mimic the messages that a paired patient support apparatus 20, 20a would send to headwall unit 144, 144a if the function or situation being tested had actually occurred on the patient support apparatus 20, 20a. In other words, test options 492a-k allow a user of configuration tool 400 to test how headwall unit 144, 144a reacts to signals it will receive from a patient support apparatus 20, 20a when the patient support apparatus 20, 20a is paired with the headwall unit in the future. It is therefore unnecessary to have an actual patient support apparatus 20, 20a positioned in the room and paired with the headwall unit 144, 144a in order to see how the headwall unit 144, 144a reacts to the messages it will receive from a patient support apparatus.

Thus, for example, if a user presses on the room light test option 492a, controller 420 of configuration tool 400 sends a message to headwall unit 144, 144a instructing it to toggle (i.e. turn on if currently off, or turn off if currently on) the connected room light 74. This is done by controller 184 of headwall unit 144, 144a sending the appropriate signal to the appropriate pin(s) of headwall interface 120, which are in electrical communication with communication outlet 64 (which is in turn in communication with room light 74). Thus, when a user selects the room light option 492a, if headwall unit 144, 144a is properly configured and coupled to the communications infrastructure of the healthcare facility, the room light in which the headwall unit 144, 144a is positioned should either turn on or off in response thereto. If this does not happen, the user is informed that something is wrong with the connection between headwall unit 144, 144a and the room light 74.

The message that configuration tool 400 sends to headwall unit 144, 144a instructing it to toggle the room light 74 on/off in response to the activation of room light test option 492a is the same message that a paired patient support apparatus 20, 20a sends to headwall unit 144, 144a when a user of the patient support apparatus 20, 20a presses on control 50s (or 50t, depending on which one of these controls correspond to room light 74 and which one correspond to reading light 78). Headwall unit 144, 144a reacts in the same manner to both messages. Thus, as explained earlier, in those embodiments where pin 2 (FIG. 32) is used to control a reading light 78, when test option 492a is activated, controller 420 sends a message to headwall unit controller 184, and controller 184 reacts to the message by changing a voltage and/or an open or closed state of an electrical circuit between pins 2 and 27 of headwall interface 120.

Similar operations are carried out for all of the other test options 492b-k of FIG. 24. Selecting reading light option 492b causes configuration tool 400 to send an instruction to headwall unit 144, 144a instructing it to toggle on/off the reading light 78, wherein the instruction is the same instruction headwall unit 144, 144a would receive from patient support apparatus 20, 20a were a user of the patient support apparatus 20 to activate control 50t (or 50s, depending upon how these two controls correlate to the room and reading lights 74 and 78, respectively).

Selecting nurse call option 492c causes configuration tool 400 to send an instruction to headwall unit 144, 144a instructing it to send a message to the nurse call system 70 indicating that a patient wishes to speak with a remotely positioned nurse. This nurse call message is the same message that patient support apparatus 20, 20a sends to headwall unit 144, 144a when the patient activates control 50g (see FIG. 3). After headwall unit 144, 144a sends a message to the nurse call system informing it of the patient's request to speak with a nurse, it sends a message back to configuration tool 400 (or patient support apparatus 20, 20a if a patient support apparatus is paired with it) instructing the patient support apparatus to illuminate its nurse call light 116. When configuration tool 400 receives this nurse call light message, it sends a message to portable computer 402 instructing software application 404 to display a message, icon, or graphic at location 494a on screen 490 that indicates that headwall unit 144, 144a has sent the nurse call light message. This lets the user of configuration tool 400 know that headwall unit 144, 144a has reacted to the activation of nurse call test option 492c properly.

Configuration tool 400 is also configured to display at location 494b a message, icon, or graphic when a remotely positioned nurse responds to the call placed by the patient. Thus, after headwall unit 144, 144a sends a nurse call message to the nurse call system 70, it monitors the voltage on one or more of the pins of headwall interface 120 that correspond to the nurse call answer light 114. As was previously noted, the pins that correspond to the nurse call answer light 114 are often pins 16 and 29 (FIG. 32). The nurse call system changes a voltage between these two pins when a nurse answers the call. Headwall unit 144, 144a is configured to send a message to patient support apparatus 20, 20a, and/or configuration tool 400 when this voltage change is detected. When patient support apparatus 20, 20a receives this message, it illuminates nurse call answer light 114. When configuration tool 400 receives this message, it sends a message to portable computer 402 and software application 404 instructs controller 434 to display a graphic, icon, or other indicator at area 494b, thereby informing the user that the nurse has answered the call and headwall unit 144, 144a has properly detected the answer.

Selecting volume up option 492d of screen 490 (FIG. 24) causes configuration tool 400 to send an instruction to headwall unit 144, 144a instructing it to turn up the volume of television 72. This instruction is the same instruction headwall unit 144, 144a would receive from patient support apparatus 20, 20a were a user of the patient support apparatus 20 to activate control 50l. If headwall unit 144, 144a is configured to properly communicate with television 72, the result will be that headwall unit 144, 144a controls the voltage on the correct pin(s) of headwall interface 120 such that the television 72 increases its volume. A user of configuration tool 400 can therefore test to see if headwall unit 144, 144a is properly configured to increase the television's volume by turning on the television 72, selecting volume up option 492d, and then listening to the television to see if its volume increases.

Similar actions are taken by headwall unit 144, 144a in response to TV test options 492e, 492g, 492h, 492i, 492j, and 492k (FIG. 24). That is, test option 492e causes controller 420 to send the same command to headwall unit 144, 144a that a patient support apparatus 20, 20a sends when a user presses on control 50m (FIG. 3). Test option 492g causes controller 420 to send the same command to headwall unit 144, 144a that a patient support apparatus 20, 20a sends when a user presses on control 50n. Test option 492h causes controller 420 to send the same command to headwall unit 144, 144a that a patient support apparatus 20, 20a sends when a user presses on control 50o. Test option 492i causes controller 420 to send the same command to headwall unit 144, 144a that a patient support apparatus 20, 20a sends when a user presses on control 50p. Test option 492j causes controller 420 to send the same command to headwall unit 144, 144a that a patient support apparatus 20, 20a sends when a user presses on control 50q. And test option 492k causes controller 420 to send the same command to headwall unit 144, 144a that a patient support apparatus 20, 20a sends when a user presses on control 50r.

Bed exit test option 492f (FIG. 24), when activated, causes controller 420 to send the same command to headwall unit 144, 144a that a patient support apparatus 20, 20a sends when its exit detection system is armed and a patient exits from patient support apparatus 20, 20a.

Location 494c of screen 490 provides an indication to the user of configuration tool 400 of whether or not the cord out alert has been activated or not on headwall unit 144, 144a. As was stated earlier, a code out state occurs when the patient support apparatus 20, 20a disconnects from headwall unit 144, 144a, and/or when headwall unit 144, 144a is decoupled from communications outlet 64. Headwall unit 144, 144a can be configured to either issue an alert when such a state is detected, or to not issue an alert when such a state is detected. Location 494c provides an indication to the user of the current configuration of headwall unit 144, 144a with respect to whether or not it is currently configured to issue a cord out alert or not.

Location 494d of screen 490 (FIG. 24) provides an indication of the current communication status between headwall unit 144, 144a and configuration tool 400. If unit 144, 144a is properly paired with configuration tool 400, a "connected" message, or the like, will be displayed in location 494d. If pairing has been terminated or not yet established, a "disconnected" message, or the like, is displayed in location 494d. Other types of messages such as "pending," "terminating," etc. may also be displayed here.

Figure 25:
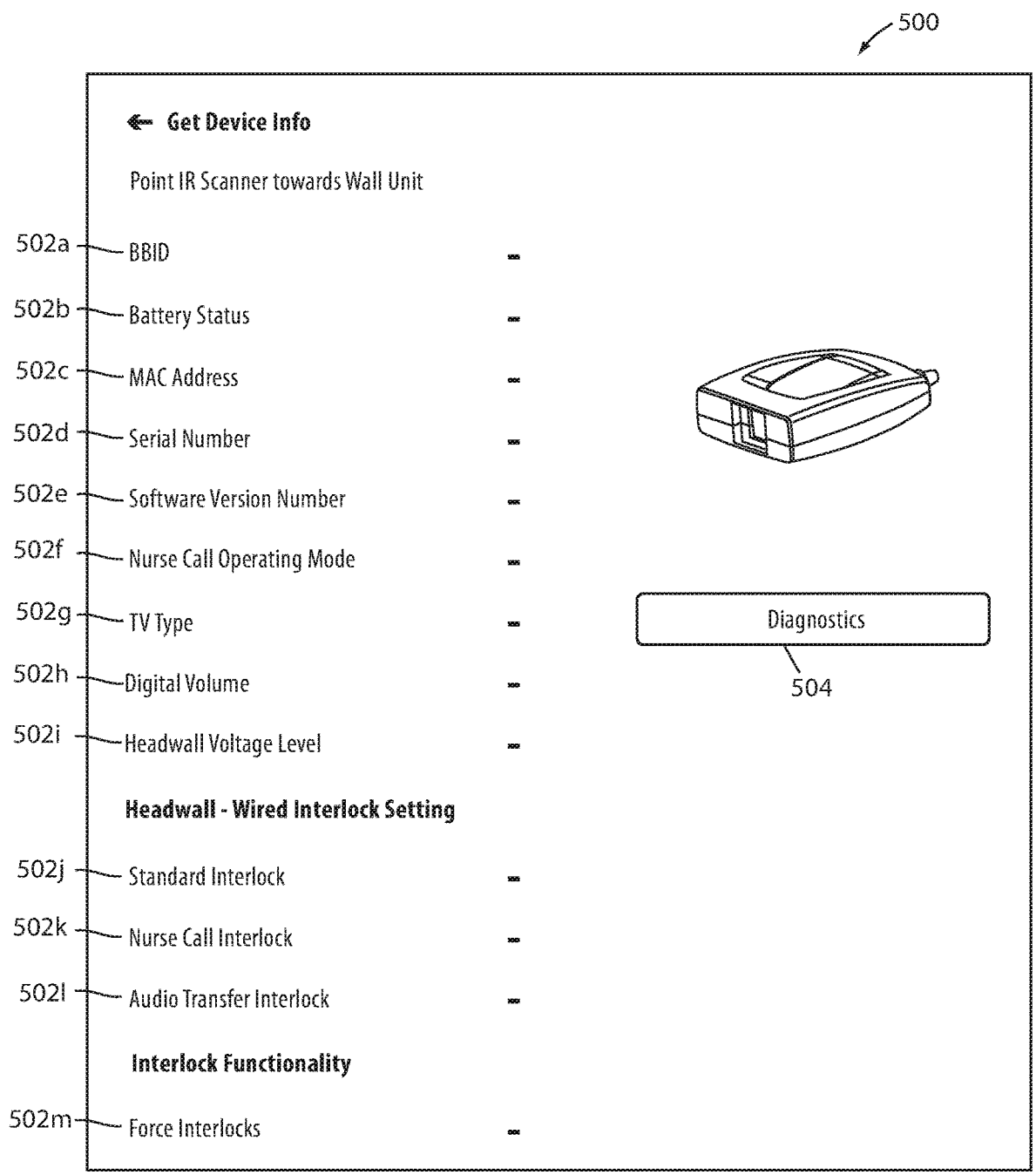
FIG. 25 is an example of a screen displayed by the software application executed by the portable computer of FIG. 16 after the user selects the "get device info" function of FIG. 22.
Figure 26:
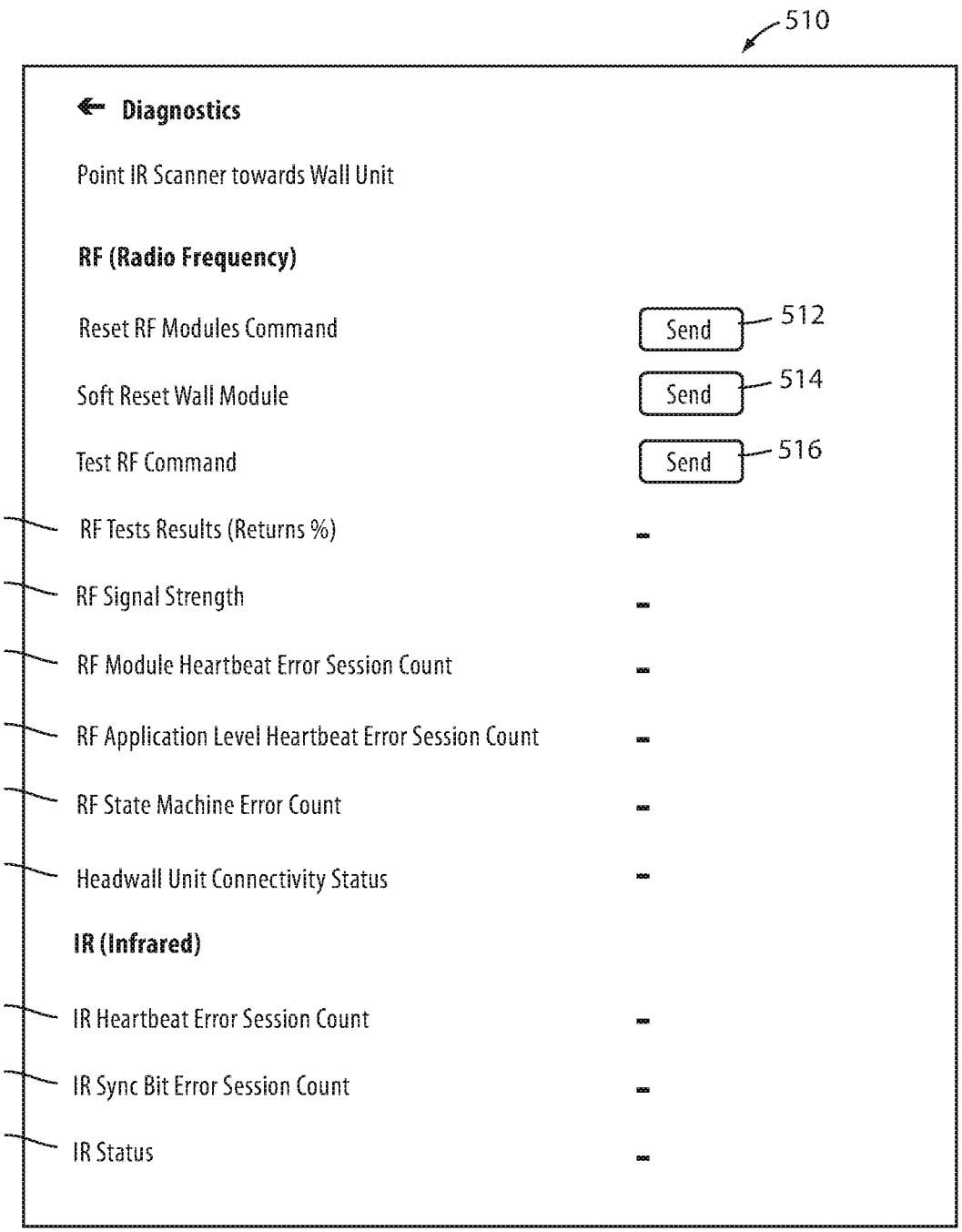
FIG. 26 is an example of a screen displayed by the software application executed by the portable computer of FIG. 16 after the user selects the "diagnostics" function of FIG. 25.

FIG. 25 shows an example of a device information screen 500 that is displayed by software application 404 on the display 432 of portable computer 402 when the user selects the get device info function 468 on home screen 460. Device info screen 500 includes a plurality of status indicators 502a-m that display the current state of the paired headwall unit 144, 144a. Device info screen 500 therefore provides the results from configuration tool 400 sending a read request to headwall unit 144, 144a asking it to provide its current configurations for each of the states that correspond to status indicators 502a-m. Thus, when a user selects the get device info function 468, application software 404 sends a request message to tool 400 via cable 406. Controller 420 of tool 400 responds to this request message by forwarding a request message to headwall unit 144, 144a via transceivers 426 and/or 428. Controller 184 of headwall unit 144, 144a responds to this request by reading all of its current states and sending them back to configuration tool 400 via transceivers 180 and/or 182. In response to the receipt of these configuration states, controller 420 of tool 400 sends the received configuration state data to software application 404 via transceiver 424. Software application 404 instructs controller 434 of portable computer 402 to display this data on information screen 500.

Status indicator 502a (FIG. 25) indicates the unique identifier of the headwall unit 144, 144a that tool 400 is currently paired with. Status indicator 502b indicates the status of a battery onboard headwall unit 144, 144a. In some embodiments, this status may refer to a charge level of the battery, while in other embodiments, it may refer to other or additional information (e.g. the age or health of the battery). MAC address indicator 502c indicates the Media Access Control address of the particular headwall unit 144, 144a that tool 400 is currently paired with. Serial number status indicator 502d indicates the serial number of the headwall unit 144, 144a that tool 400 is currently paired with. Software version indicator 502e indicates the current version of the software installed on the headwall unit 144, 144a that tool is currently paired with and that controller 184 executes.

Nurse call operating mode indicator 502f indicates the current configuration of headwall unit 144, 144a for communicating with nurse call system 70. More specifically, this indicator 502f indicates which one of the various options available in field 482 (see FIG. 23) have been selected for the paired headwall unit 144, 144a. As was discussed previously, these options may include, but are not necessarily limited to, "standard," "Hill-Rom," and "parallel."

TV type indicator 502g (FIG. 25) indicates which type of television 72 headwall unit 144, 144a is currently configured to communicate with. Examples of these various types are shown in FIG. 10. Digital volume indicator 502h indicates whether headwall unit 144, 144a has been configured to implement the digital volume function. The digital volume function was previously described with respect to option 232d of FIG. 12 and field 486 of FIG. 23.

Headwall voltage indicator 502i (FIG. 25) indicates what voltage level headwall unit 144, 144a is currently configured with. This is the voltage that may be configured via field 488 of FIG. 23, and examples of these voltages are described above with respect to screen 260 and FIG. 15.

Interlock indicators 502j-m (FIG. 25) indicate what type of interlock setting headwall unit 144, 144a is currently configured with. These interlock settings may be configured via options 232a-c and 232e of FIG. 23, and examples of these interlock settings are described above with respect to screen 230 and FIG. 12.

Information screen 500 also include a diagnostics function 504. When a user activates the diagnostic function 504, software application 404 is configured to display a diagnostics screen on display 432, such as the diagnostics screen 510 of FIG. 26. Diagnostics screen 510 includes an RF module reset option 512, a soft reset option 514, an RF test command option 516, and a plurality of data indicators 518a-i. When a user activates the RF module rest option 512, controller 420 of configuration tool 400 sends a command to the paired headwall unit 144, 144a instructing it to reset its Bluetooth module (which includes Bluetooth transceiver 182 and its associated circuitry). When a user activates the soft reset option 514, controller 420 of configuration tool 400 sends a command to the paired headwall unit 144, 144a instructing it to go through a power cycle (e.g. turn its power off and then turn the power on again). When a user activates the RF test command 516, controller 420 of configuration tool 400 sends a command to the paired headwall unit 144, 144a instructing it to go through a pairing and unpairing process a set number of time (for example seven, although other numbers may be used). During those pairings and unpairings, configuration tool 400 keeps track of the number of times the pairings were successful and unsuccessful and reports this via data indicator 518a. The number reported at indicator 518a is a percentage indicating how many times headwall unit 144, 144a and tool 400 were able to successfully pair during the test pairings activated by RF test command 516.

Data indicator 518b indicates the current signal strength of the RF transmissions from RF transceiver 182 as detected by configuration tool 400. Data indicator 518c indicates the number of any errors in the heartbeats between RF transceiver 182 and RF transceiver 428, as detected by the hardware onboard headwall unit 144, 144a that is associated with RF transceiver 182. Data indicator 518d indicates the number of any errors in the heartbeats between RF transceiver 182 and RF transceiver 428, as detected by the software executed by controller 184 of headwall unit 144, 144a. Data indicator 518e indicates the number of state machine errors in headwall unit 144, 144a, as detected by controller 184. Data indicator 518f is the same as status indicator 494d (FIG. 24).

Data indicator 518g indicates the number of any errors in the heartbeats between IR transceiver 180 and IR transceiver 426, as detected by the hardware onboard headwall unit 144, 144a that is associated with IR transceiver 180. Data indicator 518h indicates the number of any errors in the synchronization signals that are transmitted between IR transceivers 180 and 426. Finally, data indicator 518i indicates the status (e.g. connected, disconnected, pairing, etc.) of the IR communication link between IR transceiver 180 and IR transceiver 426.

Figure 27:
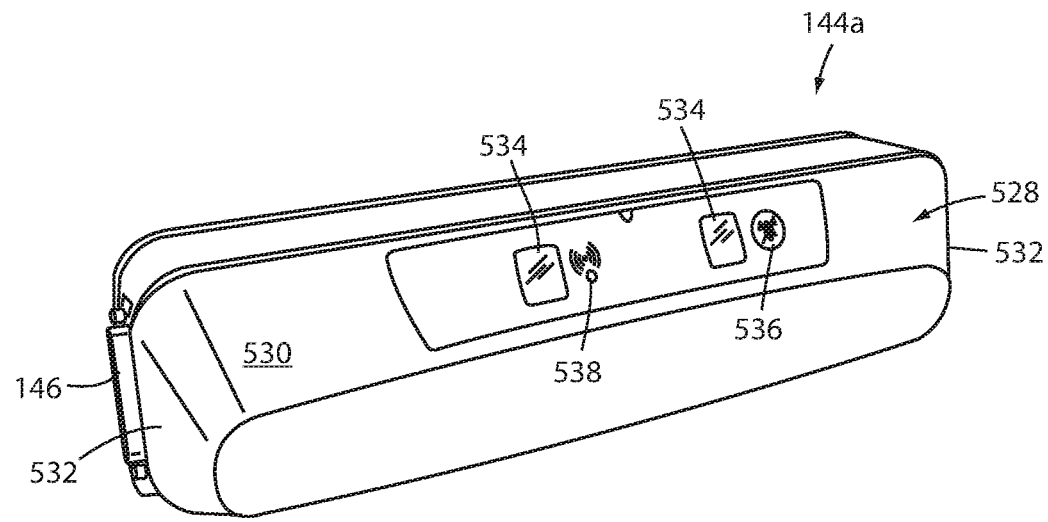
FIG. 27 is an enlarged perspective view of an embodiment of the headwall unit shown in FIGS. 7 and 16.
Figure 28:
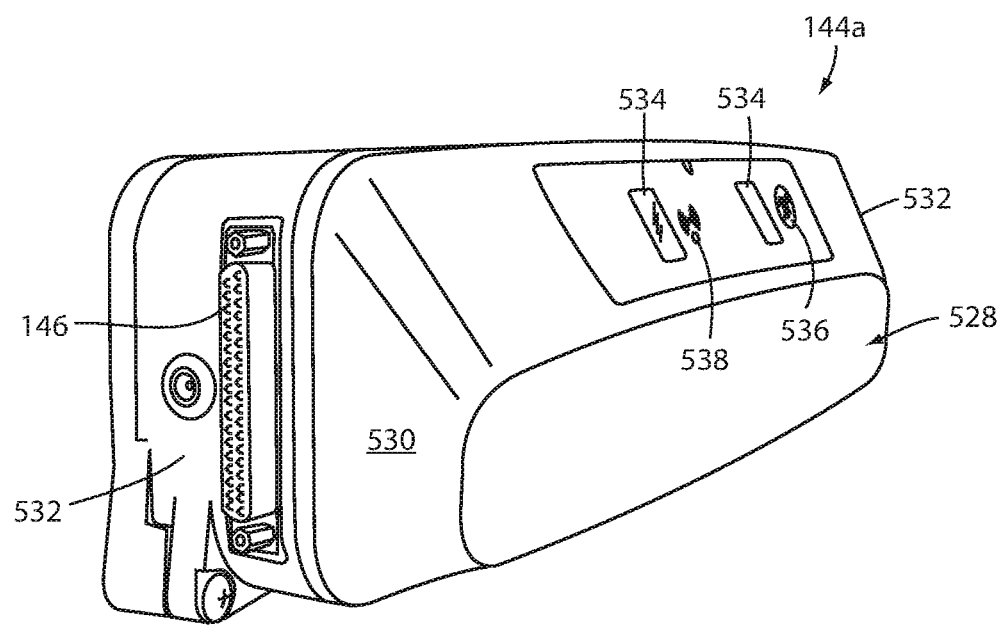
FIG. 28 is perspective view of the headwall unit of FIG. 27 taken from a different angle.

FIG. 27 illustrates in greater detail one manner in which headwall unit 144a may be implemented. As shown therein, headwall unit 144a includes a main housing 528 having a front face 530 and a pair of sides 532. One of the sides 532 includes a connector 146 adapted to couple to one end of a connector cable 162 (see FIG. 7). The other end of the connector cable is adapted to couple to the communication outlet 64 of a conventional nurse call system. The connector cable 162 therefore allows headwall unit 144a to be mounted to headwall 62 at a location that is offset from communications outlet 64. In some embodiments, connector 146 includes thirty-seven pins and/or thirty-seven sockets adapted to receive thirty-seven pins/sockets from connector cable 162. As was previously mentioned, such thirty-seven pin connections are one of the most common types of connections found on existing headwalls of medical facilities for making connections to the nurse call system 70 and room devices 72, 74, and 78. Connector 146 and its associated connector cable 162 are therefore configured to mate with one of the most common type of communication outlets 64 used in medical facilities. Such 37 pin connectors, however, are not the only type of connectors, and it will be understood that headwall unit 144a can utilize different types of connectors 146 that are adapted to electrically couple to different types of communication outlets 64.

Front face 530 of headwall unit 144a includes a pair of IR openings 534 in housing 528 that are adapted to allow infrared waves to pass to and from IR transceiver 180. In some embodiments, headwall unit 144a may include multiple IR transceivers 180 that are positioned in different locations on headwall unit 144a so that controller 184 can select the one to use based on the relative signal strengths of the IR signals it receives from the adjacent patient support apparatus 20, 20a or configuration tool 400. Front face 530 also includes a cord out cancel button 536 and a status indicator 538. The cord out cancel button 536 is pressed by a user when headwall unit 144a is configured to (as discussed above), and actually is, issuing a cord out alert and the user desires to cancel the cord out alert. The cancellation of the alert involves changing the electrical characteristic on one or more of the pins of headwall interface 120.

Figure 29:
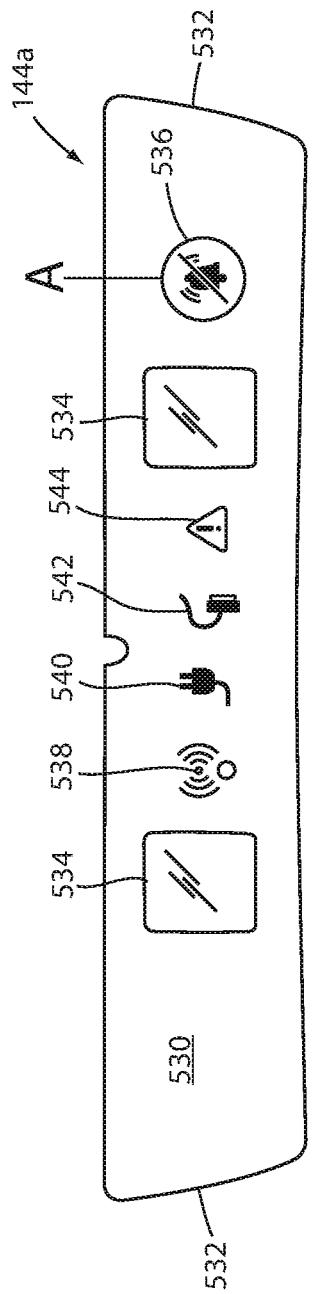
FIG. 29 is a table identifying the meaning of different indications that are presented by the headwall unit of FIG. 27.

Status indicator 538 is illuminated in different manners to indicate the connection status of headwall unit 144a to a nearby device, wherein the nearby device is either a patient support apparatus 20, 20a or a configuration tool 400. FIG. 29 illustrates the different manners in which status indicator 538 may be illuminated to convey different status information. As shown therein, when indicator 538 is indicated with steady and constant illumination, it indicates that headwall unit 144a is properly paired with a nearby patient support apparatus 20, 20a (or configuration tool 400). When status indicator 538 is illuminated in a pulsed manner, it indicates that headwall unit 144a is in the process of connecting (e.g. pairing) to a nearby patient support apparatus 20, 20a (or configuration tool 400). When status indicator 538 flashes, along with a nurse call cable icon 542, it indicates that there is a connection error between headwall unit 144a and the nearby patient support apparatus 20, 20a (or configuration tool 400). The difference between flashing and pulsing is that flashing involves turning the light on/off in a pattern that is the same as, or closely resembles, a square wave, while pulsing involves controlling the intensity of the emitted light in a pattern that generally follows a sine wave with a frequency less than that of the pulsing. In some embodiments, the differences between the flashing and the pulsing are the same as the differences between the flashing and pulsing of lights disclosed in commonly assigned PCT patent application PCT/US2020/038462 filed Jun. 18, 2020, by inventors Kurosh Nahavandi et al., the complete disclosure of which is incorporated herein by reference.

As is also illustrated in FIG. 29, front face 530 of headwall unit 144a also includes three icons that are selectively illuminated: a power cord icon 540, a nurse call cable icon 542, and a caution icon 544. Controller 184 of headwall unit 144a pulses power cord icon 540 when headwall unit 144a is not plugged into an electrical outlet. Controller 184 flashes power cord icon 540 when the battery onboard headwall unit 144a is low. Controller 184 pulses the nurse call cable icon 542 when the nurse call connector cable 162

(see FIG. 7) is unplugged from connector 146 of headwall unit 144*a* or it is unplugged from communication outlet 64, or both. In other words, controller 184 pulses icon 542 when headwall unit 144*a* is not communicatively coupled to communication outlet 64.

Controller 184 illuminates caution icon 544 in a steady and continuous manner when headwall unit 144*a* has not yet been configured (either by a configuration tool 400 or by a patient support apparatus 20, 20*a*). Controller 184 flashes caution icon 544 when one or more errors are detected by controller 184. Further, controller 184 flashes both caution icon 544 and the power cord icon 540 when a battery error is detected. Still other types of data and/or icons may be included on the front face of headwall unit 144*a* that communicate other types of information to the user about the status of headwall unit 144*a*.

As was mentioned previously, when a user selects the record module ID function 470 from home screen 460, software application 404 is configured to read the unique identifier of the currently paired headwall unit 144*a* (received at step 446 of algorithm 440) and add it to a conventional spreadsheet stored in the memory of portable computer 402. Software application 404 does this for each headwall unit 144*a* that the user activates the record ID function 470 with. The result is a single spreadsheet containing all of the unique identifiers of the headwall units 144, 144*a* that the user paired configuration tool 400 with. This spreadsheet can then be subsequently edited by the user to add additional information, such as, for example, the location of each headwall unit 144, 144*a*. The addition of the location information for each headwall unit 144, 144*a* to the spreadsheet creates a single file that ties together the location of each headwall unit 144, 144*a* with their unique ID. This file can then be used by a server (e.g. patient support apparatus server 84), or other electronic entity, to correlate signals received from a patient support apparatus 20, 20*a* to a location of that patient support apparatus 20, 20*a*. In other words, when a patient support apparatus 20 reads the unique identifier from an adjacent headwall unit 144, 144*a* to which it is currently paired, it can then send that information to a server, the server can consult the file containing the spreadsheet information, and use that information to determine the current location of the patient support apparatus 20, 20*a*. The record ID function 470 therefore helps facilitate the mapping process that maps the identify of each unique headwall unit 144, 144*a* to a particular location within the healthcare facility.

It will be understood that, in some embodiments, software application 404 may be part of a larger software suite, such as, but not limited to, the service tool software application 136 disclosed in commonly assigned, U.S. patent application Ser. No. 17/241,842 filed Apr. 27, 2021, by inventors Frank Lee et al. and entitled WIRELESS SERVICE TECHNOLOGY FOR PATIENT SUPPORT APPARATUSES, the complete disclosure of which is hereby incorporated herein by reference. When so incorporated into a larger software suite, a user may use the software suite to not only update and configure headwall units 144, 144*a*, but also to install software updates on patient support apparatus 20 as well. In some such embodiments, the software suite may be configured, after installing a software update on patient support apparatus 20, to leave a copy of the software update in a memory onboard the patient support apparatus 20. The copy may be utilized in the future by the patient support apparatus 20 should the software update need to be re-installed, such as if a component of patient support apparatus 20 needs to be replaced. Patient support apparatus 20 may therefore be configured, in some embodiments, to not only install new software, but to also store a copy of the newly installed software in a separate file that can be used for re-installation purposes, should the installation later need to be duplicated.

It will be understood by those skilled in the art that the use of the term "transceiver" throughout this specification is not intended to be limited to devices in which a transmitter and receiver are necessarily within the same housing, or share some circuitry. Instead, the term "transceiver" is used broadly herein to refer to both structures in which circuitry is shared between the transmitter and receiver, and transmitter-receivers in which the transmitter and receiver do not share circuitry and/or a common housing. Thus, the term "transceiver" refers to any device having a transmitter component and a receiver component, regardless of whether the two components are a common entity, separate entities, or have some overlap in their structures.

Various additional alterations and changes beyond those already mentioned herein can be made to the above-described embodiments. This disclosure is presented for illustrative purposes and should not be interpreted as an exhaustive description of all embodiments or to limit the scope of the claims to the specific elements illustrated or described in connection with these embodiments. For example, and without limitation, any individual element(s) of the described embodiments may be replaced by alternative elements that provide substantially similar functionality or otherwise provide adequate operation. This includes, for example, presently known alternative elements, such as those that might be currently known to one skilled in the art, and alternative elements that may be developed in the future, such as those that one skilled in the art might, upon development, recognize as an alternative. Any reference to claim elements in the singular, for example, using the articles "a," "an," "the" or "said," is not to be construed as limiting the element to the singular.

What is claimed is:

1. A portable handheld configuration tool for configuring a headwall unit attached to a headwall of a healthcare facility, wherein the headwall unit is adapted to be electrically coupled to an outlet on the headwall that is in electrical communication with a room device positioned within a room in which the headwall unit is located, the portable handheld configuration tool comprising:
 a housing;
 a transceiver for communicating with a portable computer;
 a first infrared transceiver adapted to communicate with a second infrared transceiver incorporated into the headwall unit;
 a first radio frequency (RF) transceiver adapted to communicate with a second radio frequency (RF) transceiver incorporated into the headwall unit; and
 a controller adapted to perform the following:
 (a) receive an identifier from the headwall unit via at least one of the first infrared transceiver or the first radio frequency transceiver, wherein the identifier uniquely identifies the headwall unit;
 (b) establish a communication link between the first RF transceiver and the second RF transceiver;
 (c) receive a configuration setting from the headwall unit via at least one of the first infrared transceiver or the first radio frequency transceiver; and
 (d) transmit the configuration setting to the portable computer via the transceiver, wherein the configuration setting includes at least one of the following: (1) voltage data specifying a voltage level the headwall unit applies to a pin of the outlet in order to control a television; (2) first sequence data specifying a first sequence of voltage levels the headwall unit applies to the pin to cause the television to change channels; (3) a second sequence of voltage levels the headwall unit applies to the pin to cause the television to change volume; (4) an identification of pins for communicating with a nurse call system; (5) electrical data indicating how to control a room light; or (6) electrical data indicating how to control a reading light.

2. The portable handheld configuration tool of claim 1 wherein the transceiver is a wired Universal Serial Bus (USB) transceiver and the controller is adapted to receive electrical power from the portable computer.

3. The portable handheld configuration tool of claim 1 wherein the first RF transceiver is a Bluetooth transceiver; the portable computer is one of a laptop or a smart phone; and the outlet is also in electrical communication with a nurse call system installed in the healthcare facility.

4. The portable handheld configuration tool of claim 1 wherein the controller is further adapted to receive a new configuration setting from the portable computer, transmit the new configuration setting to the headwall unit, and to instruct the headwall unit to replace the configuration setting with the new configuration setting.

5. The portable handheld configuration tool of claim 2 wherein the controller is further adapted to receive a test command from the portable computer and to transmit a test message to the headwall unit in response to receiving the test command, the test message instructing the headwall unit to take a particular action.

6. A portable handheld configuration tool for configuring a headwall unit attached to a headwall of a healthcare facility, wherein the headwall unit is adapted to be electrically coupled to an outlet on the headwall that is in electrical communication with a room device positioned within a room in which the headwall unit is located, the portable handheld configuration tool comprising:
  a housing;
  a transceiver for communicating with a portable computer;
  a first infrared transceiver adapted to communicate with a second infrared transceiver incorporated into the headwall unit;
  a first radio frequency (RF) transceiver adapted to communicate with a second radio frequency (RF) transceiver incorporated into the headwall unit; and
  a controller adapted to perform the following:
  (a) receive an identifier from the headwall unit via at least one of the first infrared transceiver or the first radio frequency transceiver, wherein the identifier uniquely identifies the headwall unit;
  (b) establish a communication link between the first RF transceiver and the second RF transceiver;
  (c) receive a configuration setting from the portable computer via the transceiver; and
  (d) transmit the configuration setting to the headwall unit via at least one of the first infrared transceiver or the first RF transceiver; wherein the configuration setting includes at least one of the following: (1) voltage data specifying a voltage level the headwall unit is to apply to a pin of the outlet in order to control a television; (2) first sequence data specifying a first sequence of voltage levels the headwall unit is to apply to the pin to cause the television to change channels; (3) a second sequence of voltage levels the headwall unit is to apply to the pin to cause the television to change volume; (4) an identification of pins for communicating with a nurse call system; (5) electrical data indicating how to control a room light; or (6) electrical data indicating how to control a reading light.

7. The portable handheld configuration tool of claim 6 wherein the transceiver is a wired Universal Serial Bus (USB) transceiver and the controller is adapted to receive electrical power from the portable computer.

8. The portable handheld configuration tool of claim 7 wherein the first RF transceiver is a Bluetooth transceiver; the portable computer is one of a laptop or a smart phone; and the outlet is also in electrical communication with a nurse call system installed in the healthcare facility.

9. The portable handheld configuration tool of claim 7 wherein the controller is further adapted to receive a test command from the portable computer and to transmit a test message to the headwall unit in response to receiving the test command, the test message instructing the headwall unit to take at least one of the following actions:
  (a) to transmit a command to a television to change a channel of the television, wherein the television is the room device;
  (b) to transmit a command to a room light to turn on, wherein the room light is the room device; or
  (c) to transmit a command to a nurse call system indicating that a patient has exited from a patient support apparatus, wherein the outlet is also in electrical communication with the nurse call system.

10. A portable handheld configuration tool for configuring a headwall unit attached to a headwall of a healthcare facility, wherein the headwall unit is adapted to be electrically coupled to an outlet on the headwall that is in electrical communication with a room device positioned within a room in which the headwall unit is located, the portable handheld configuration tool comprising:
  a housing;
  a transceiver for communicating with a portable computer;
  a first infrared transceiver adapted to communicate with a second infrared transceiver incorporated into the headwall unit;
  a first radio frequency (RF) transceiver adapted to communicate with a second radio frequency (RF) transceiver incorporated into the headwall unit; and
  a controller adapted to perform the following:
  (a) receive an identifier from the headwall unit via at least one of the first infrared transceiver or the first radio frequency transceiver, wherein the identifier uniquely identifies the headwall unit;
  (b) establish a communication link between the first RF transceiver and the second RF transceiver;
  (c) receive a configuration setting from the portable computer via the transceiver;
  (d) transmit the configuration setting to the headwall unit via at least one of the first infrared transceiver or the first RF transceiver;
  (e) monitor a first set of heartbeat messages exchanged between the first infrared transceiver and the second infrared transceiver;
  (f) monitor a second set of heartbeat messages exchanged between the first RF transceiver and the second RF transceiver;
  (g) transmit first and second error data regarding the first and second sets of heartbeat messages, respectively, to the portable computer via the transceiver;
  (h) receive a new configuration setting from the portable computer;

(i) transmit the new configuration setting to the headwall unit; and (j) instruct the headwall unit to replace the configuration setting with the new configuration setting.

11. A portable handheld configuration tool for configuring a headwall unit attached to a headwall of a healthcare facility, wherein the headwall unit is adapted to be electrically coupled to an outlet on the headwall that is in electrical communication with a room device positioned within a room in which the headwall unit is located, the portable handheld configuration tool comprising:

a housing;

a transceiver for communicating with a portable computer;

a first infrared transceiver adapted to communicate with a second infrared transceiver incorporated into the headwall unit;

a first radio frequency (RF) transceiver adapted to communicate with a second radio frequency (RF) transceiver incorporated into the headwall unit; and a controller adapted to perform the following:

(a) receive an identifier from the headwall unit via at least one of the first infrared transceiver or the first radio frequency transceiver, wherein the identifier uniquely identifies the headwall unit;

(b) establish a communication link between the first RF transceiver and the second RF transceiver;

(c) receive a test command from the portable computer via the transceiver;

(d) transmit a test message to the headwall unit via at least one of the first infrared transceiver or the first RF transceiver in response to receiving the test command, the test message instructing the headwall unit to take a particular action;

(e) monitor a first set of heartbeat messages exchanged between the first infrared transceiver and the second infrared transceiver;

(f) monitor a second set of heartbeat messages exchanged between the first RF transceiver and the second RF transceiver; and (g) transmit first and second error data regarding the first and second sets of heartbeat messages, respectively, to the portable computer via the transceiver.

12. The portable handheld configuration tool of claim 11 wherein the room device is one of a television or a room light, and the particular action is one of transmitting a command to the television to change a channel of the television or transmitting a command to the room light to turn on.

13. The portable handheld configuration tool of claim 11 wherein the outlet is also in electrical communication with a nurse call system installed in the healthcare facility, and the particular action is to transmit a command to the nurse call system indicating that a patient has exited from a patient support apparatus.

14. The portable handheld configuration tool of claim 11 wherein the controller is further adapted to receive a configuration setting from the portable computer via the transceiver, and to transmit the configuration setting to the headwall unit via at least one of the first infrared transceiver or the first RF transceiver; and wherein the transceiver is a wired Universal Serial Bus (USB) transceiver, the controller is adapted to receive electrical power from the portable computer, and the first RF transceiver is a Bluetooth transceiver.

15. The portable handheld configuration tool of claim 11 wherein the headwall unit is further adapted to use the second infrared transceiver to communicate with a third infrared transceiver positioned onboard a patient support apparatus, and to use the second RF transceiver to communicate with a third RF transceiver positioned onboard the patient support apparatus, and wherein the controller is further adapted to read a stored configuration setting stored in the headwall unit and to transmit the stored configuration setting to the portable computer via the transceiver.

* * * * *